United States Patent
Noguchi et al.

(10) Patent No.: US 12,235,261 B2
(45) Date of Patent: Feb. 25, 2025

(54) METHOD FOR MEASURING CELLULAR UPTAKE OF MOLECULES

(71) Applicant: Chugai Seiyaku Kabushiki Kaisha, Tokyo (JP)

(72) Inventors: Yuki Noguchi, Shizuoka (JP); Takeru Nambu, Shizuoka (JP); Kazuhisa Ozeki, Shizuoka (JP); Noriaki Ohminato, Shizuoka (JP); Toshito Nakagawa, Shizuoka (JP); Sotaro Naoi, Shizuoka (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 837 days.

(21) Appl. No.: 16/756,415

(22) PCT Filed: Oct. 19, 2018

(86) PCT No.: PCT/JP2018/039005
§ 371 (c)(1),
(2) Date: Apr. 15, 2020

(87) PCT Pub. No.: WO2019/078357
PCT Pub. Date: Apr. 25, 2019

(65) Prior Publication Data
US 2021/0190764 A1 Jun. 24, 2021

(30) Foreign Application Priority Data
Oct. 20, 2017 (JP) ................................. 2017-203994

(51) Int. Cl.
*G01N 33/50* (2006.01)
*G01N 33/49* (2006.01)
*G01N 33/569* (2006.01)
*G01N 33/58* (2006.01)

(52) U.S. Cl.
CPC ..... *G01N 33/5035* (2013.01); *G01N 33/4915* (2013.01); *G01N 33/5067* (2013.01); *G01N 33/56966* (2013.01); *G01N 33/582* (2013.01); *G01N 2333/70589* (2013.01); *G01N 2333/70596* (2013.01); *G01N 2333/7155* (2013.01)

(58) Field of Classification Search
CPC .......... G01N 33/56966; G01N 33/582; G01N 33/57484; G01N 33/5035; G01N 2333/70589; G01N 2333/70596; G01N 2333/7155; G01N 33/48
See application file for complete search history.

(56) References Cited

U.S. PATENT DOCUMENTS

| | | | |
|---|---|---|---|
| 6,608,213 | B1 | 8/2003 | Sato et al. |
| 2011/0318304 | A1 | 12/2011 | Lackmann et al. |
| 2015/0056182 | A1 | 2/2015 | Igawa et al. |
| 2018/0147242 | A1 | 5/2018 | Miyajima et al. |

FOREIGN PATENT DOCUMENTS

| | | | |
|---|---|---|---|
| CA | 2831770 | A1 | 10/2012 |
| JP | 2001289851 | A | 10/2001 |
| JP | 2011144125 | A | 7/2011 |
| JP | 2013537403 | A | 10/2013 |
| WO | WO-2009037839 | A1 | 3/2009 |
| WO | WO2011122011 | A2 | 10/2011 |
| WO | WO-2012132067 | A1 | 10/2012 |
| WO | WO-2013081143 | A1 | 6/2013 |
| WO | WO-2014113510 | A1 | 7/2014 |
| WO | WO-2016098357 | A1 | 6/2016 |
| WO | WO-2016117346 | A1 | 7/2016 |
| WO | WO-2016148216 | A1 | 9/2016 |

OTHER PUBLICATIONS

U.S. Appl. No. 18/559,876, filed Nov. 2023, Noguchi et al., G01N 33/5035, 435/7.1.*
Poisson et al. Liver Sinusoidal endothelial cells: Physiology and role in liver diseases. Journal of Hepatology 2017. 66: 212-227 (Jul. 2016).*
Tan et al. Cellular Updake of rFVIIIFc in liver is primarily contributed by sinusoidal endothelial cells. Blood 120 (21): Abstract No. 2219 (Nov. 16, 2012).*
Swystun et al. The scavenger receptor stabilin-2 (STAB-2) mediates clearance of human von Willebrand factor and factor VIII by liver sinusoidal endothelial cells. Journal of Thrombosis and Haemostasis 13 (Suppl 2) p. 252: Abstract No. OR409 (Jun. 2015).*
Becton Dickinson. The Cell Sort. FLOWJO: Cytometry pp. 1-6 Product Description (printed 2023).*
Arend, W. P. and Sturge, J. C., "Composition and Biologic Properties of Soluble IgG-Anti-IgG Immune Complexes: Effects of Variations in the Specificity of Rabbit Antibodies to Different Structural Components of Human IgG," J Immunol., 123(1):447-454 (1979).
Benacerraf, B., et al., "The Clearance of Antigen Antibody Complexes From the Blood by the Reticulo-Endothelial System," J Immunol., 82(2):131-137 (1959).
Bijsterbosch, M. K., et al., "In vivo fate of phosphorothioate antisense oligodeoxynucleotides: predominant uptake by scavenger receptors on endothelial liver cells," Nucleic Acids Research, 25(16):3290-3296 (1997).
Bruhns, P., et al., "Specificity and affinity of human Fcγ receptors and their polymorphic variants for human IgG subclasses," Blood, 113(16):3716-3725 (2009).

(Continued)

*Primary Examiner* — Gailene Gabel
(74) *Attorney, Agent, or Firm* — Nixon & Vanderhye P.C.

(57) ABSTRACT

The present invention provides a method for measuring a cellular uptake amount of a molecule, comprising (i) adding the molecule to an organ-derived cell population to perform incubation, (ii) sorting the organ-derived cell population based on the expression levels of CD31 and CD45, and (iii) after steps (i) and (ii), measuring the amount of the molecule incorporated into the cell population sorted in the step (ii), wherein the molecule is incorporated into cells via a cell surface receptor.

13 Claims, 11 Drawing Sheets

Specification includes a Sequence Listing.

(56) References Cited

OTHER PUBLICATIONS

Deleve, L. D., "Liver sinusoidal endothelial cells and liver regeneration," J Clin Invest., 123(5):1861-1866 (2013).
Filali, E. E., et al., "Human Liver Endothelial Cells, But Not Macrovascular or Microvascular Endothelial Cells, Engraft in the Mouse Liver," Cell Transplantation, 22(10):1801-1811 (2013).
Finbloom, D. S. and Plotz, P. H., "Studies of Reticuloendothelial Function in the Mouse with Model Immune Complexes," J Immunol., 123(4):1594-1599 (1979).
Ganesan, L. P., et al., "FcγRIIb on liver sinusoidal endothelial clears small immune complexes," J Immunol., 189(10):4981-4988 (2012).
Graham, M. J., et al., "Hepatic distribution of a phosphorothioate oligodeoxynucleotide within rodents following intravenous administration," Biochem Pharmacol., 62(3):297-306 (2001).
Igawa, T., et al., "Sweeping antibody as a novel therapeutic antibody modality capable of eliminating soluble antigens from circulation," Immunol Rev., 270(1):132-151 (2016).
International Search Report dated Jan. 22, 2019 in International Application No. PCT/JP2018/039005.
Iwayanagi, Y., et al., "Inhibitory FcγRIIb-Mediated Soluble Antigen Clearance from Plasma by a pH-Dependent Antigen-Binding Antibody and Its Enhancement by Fc Engineering," J Immunol., 195(7):3198-3205 (2015).
Kurlander, R. J., et al., "The Blockade of Fc Receptor-Mediated Clearance of Immune Complexes In Vivo by a Monoclonal Antibody (2.4G2) Directed Against Fc Receptors on Murine Leukocytes," J Immunol., 133(2):855-862 (1984).
Løvdal, T., et al., "Fc receptor mediated endocytosis of small soluble immunoglobulin G immune complexes in Kupffer and endothelial cells from rat liver," J Cell Sci., 113(18):3255-3266 (2000).
Luu, K. T., et al., "A Model-Based Approach to Predicting the Human Pharmacokinetics of a Monoclonal Antibody Exhibiting Target-Mediated Drug Disposition," J Pharmacol Exp Ther., 341(3):702-708 (2012).
March, S., et al., "Microenvironmental Regulation of the Sinusoidal Endothelial Cell Phenotype In Vitro," Hepatology, 50(3):920-928 (2009).
Marks, K. M. and Nolan, G. P., "Chemical labeling strategies for cell biology," Nature Methods, 3(8):591-596 (2006).
Martin-Armas, M., et al., "Toll-like receptor 9 (TLR9) is present in murine liver sinusoidal endothelial cells (LSECs) and mediates the effect of CpG-oligonucleotides," J Hepatol., 44(5):939-946 (2006).
Mellman, I., et al., "Internalization and Rapid Recycling of Macrophage Fc Receptors Tagged with Monovalent Antireceptor Antibody: Possible Role of a Prelysosomal Compartment," J Cell Biol., 98(4):1163-1169 (1984).
Miller, C. M., et al., "Stabilin-1 and Stabilin-2 are specific receptors for the cellular internalization of phosphorothioate-modified antisense oligonucleotides (ASOs) in the liver," Nucleic Acids Res., 44(6):2782-2794 (2016).
Mousavi, S. A., et al., "Receptor-Mediated Endocytosis of Immune Complexes in Rat Liver Sinusoidal Endothelial Cells Is Mediated by FcγRIIb2," Hepatology, 46(3):871-884 (2007).
Oitate, M., et al., "Prediction of Human Pharmacokinetics of Therapeutic Monoclonal Antibodies from Simple Allometry of Monkey Data," Drug Metab. Pharmacokinet., 26(4):423-430 (2011).
Pfeiffer, E., et al., "Isolation, characterization, and cultivation of human hepatocytes and non-parenchymal liver cells," Exp Biol Med., 240(5):645-656 (2015).
Poisson, J., et al., "Liver sinusoidal endothelial cells: Physiology and role in liver diseases," J Hepatol., 66(1):212-227 (2017).
Qiao, S.-W., et al., "Dependence of antibody-mediated presentation of antigen on FcRn," PNAS, 105(27):9337-9342 (2008).
Rojas, J. R., et al., "Formation, Distribution, and Elimination of Infliximab and Anti-Infliximab Immune Complexes in Cynomolgus Monkeys," J Pharmacol Exp Ther., 313(2): 578-585 (2005).
Schwab, I. and Nimmerjahn, F., "Intravenous immunoglobulin therapy: how does IgG modulate the immune system?" Nat Rev Immunol., 13(3):176-189 (2013).
Singh, A. P., et al., "Quantitative Prediction of Human Pharmacokinetics for mAbs Exhibiting Target-Mediated Disposition," AAPS J., 17(2):389-399 (2015).
Takai, T., "Roles of Fc Receptors in Autoimmunity," Nat Rev Immunol., 2(8):580-592 (2002).
Weflen, A. W., et al., "Multivalent immune complexes divert FcRn to lysosomes by exclusion from recycling sorting tubules," Mol Biol Cell, 24(15):2398-2405 (2013).
Daenen, L. G. M., et al., "Chemotherapy Enhances Metastasis Formation via VEGFR-1-Expressing Endothelial Cells," Cancer Res., 71(22):6976-6985 (2011).
Extended European Search Report dated Aug. 11, 2021 in European Application No. 18868009.4, 12 pages.
Fagiani, E., et al., "An immature B cell population from peripheral blood serves as surrogate marker for monitoring tumor angiogenesis and anti-angiogenic therapy in mouse models," Angiogenesis, 18:327-345 (2015).
Jaramillo, C. A. C., et al., "Toward in vitro-to-in vivo translation of monoclonal antibody pharmacokinetics: Application of a neonatal Fc receptor-mediated transcytosis assay to understand the interplaying clearance mechanisms," mAbs, 9(5):781-791 (2017).
Nonaka, H., et al., "Development of Murine Hepatic Sinusoidal Endothelial Cells Characterized by the Expression of Hyaluronan Receptors," Developmental Dynamics, 236:2258-2267 (2007).

\* cited by examiner

METHOD FOR MEASURING CELLULAR UPTAKE OF MOLECULES

CROSS-REFERENCE TO RELATED APPLICATIONS

This application is a U.S. National Phase of PCT Application No. PCT/JP2018/039005, filed Oct. 19, 2018, which claims the benefit of Japanese Patent Application No. 2017-203994, filed Oct. 20, 2017, each of which is incorporated herein by reference in its entirety.

REFERENCE TO SEQUENCE LISTING SUBMITTED ELECTRONICALLY

The content of the electronically submitted sequence listing (Name: 6663_0133 Sequence_Listing.txt; Size: 508 kilobytes; and Date of Creation: Apr. 13, 2020) filed with the application is incorporated herein by reference in its entirety.

TECHNICAL FIELD

The present invention relates to a method for measuring uptake of a molecule incorporated into cells via a cell surface receptor, such as an antigen-antibody complex (immune complex), an antibody, and a nucleic acid, in vitro, a composition for uptake assays of the molecule, and the like.

BACKGROUND ART

A complex consisting of an antibody and an antigen, called immune complex, is an antibody bound to a foreign substance present in a living body. Immunoconjugates are eliminated from bodies by reticuloendothelial system, resulting in removal of foreign substances from bodies (Non Patent Literature 1). An antibody includes Fab and Fc regions, wherein the Fc region is recognized by an Fc receptor present on a cell surface (Non Patent Literature 15). Among Fc receptors, Fc gamma receptor (FcγR) is a receptor that recognizes the Fc region of IgG antibody. FcγR is divided into four subtypes: FcγRI, II, III, and IV. FcγRIIB, a member of FcγRII, has been reported to be a receptor that repressively acts on immunity ("γ" may be represented as "g", "II" may be represented as "2", and "B" may be represented as "b") (Non Patent Literature 2, Non Patent Literature 3). FcγRIIB is also known to be a receptor that is profoundly involved in elimination of immune complexes from blood (Non Patent Literatures 4 to 7). In recent years, antibodies have been actively researched and developed for pharmaceutical agents. For example, there have been attempts to produce antibodies having amino acid sequences modified to facilitate the formation of immune complexes or binding to FcγR, and administer the produced antibodies to animals to remove soluble proteins in plasma (Non Patent Literature 8, Non Patent Literature 9, Patent Literatures 1 to 4).

FcγRIIB has been reported to be expressed on mainly liver sinusoidal endothelial cells; LSECs. In mice, three fourths of FcγRIIB has been reported to be highly expressed in the liver, 90% of which is expressed in LSECs (Non Patent Literature 10). It is also reported that when immune complexes were administered to mice to assess the percentage transfer of the immune complexes to the liver, lung, spleen, kidney, and blood, the multimer-forming immune complex had a high percentage transfer to the liver compared with the monomer- or dimer-forming immune complex (Non Patent Literature 5). Moreover, it is revealed that when immune complexes were administered to FcγRIIB knockout and wild-type mice, the FcγRIIB knockout mice had the greatly lowered elimination rate of the immune complexes compared with the wild-type mice (Non Patent Literature 10). It is further reported that hepatic nonparenchymal cells taken from transgenic mice expressing human FcγRIIB were used to assess uptake of the immune complex consisting of IgE and an anti-IgE antibody, which demonstrated the uptake of the immune complex into CD146+ CD45low LSECs (Patent Literature 3). These results suggest that immune complexes in mice are incorporated into LSECs via FcγRIIB to result in elimination.

It is also reported in rats that immune complexes are eliminated via FcγRIIB on LSECs (Non Patent Literatures 7 and 11).

It is reported in monkeys that when biodistribution of immune complexes was assessed with gamma-ray imaging 24 hours after administration of a radiolabeled antibody, high-concentration signals were observed in the liver in the administration of immune complex-forming antibodies, as compared with the administration of the control antibody that forms no immune complex in which the signals were detected in blood-rich organs such as heart (Non Patent Literature 12). Immunostaining further indicated that the immune complexes were also accumulated in vascular endothelium and Kupffer cells (Non Patent Literature 12). It is also reported that an antibody capable of more lowering the concentration of soluble antigens in the blood is obtained by increasing affinity of the antibody to FcγRIIB (Patent Literatures 4 and 5).

On the other hand, in monkeys, expression sites of FcγRIIB and cells primarily affecting elimination of immune complexes have not been identified, and the uptake mechanism and uptake rate of immune complexes are also unknown.

In humans, markers expressed on LSECs are identified, and FcγRIIB is demonstrated to be expressed on LSECs (Non Patent Literatures 13 and 14); however, the elimination mechanism and kinetics of immune complexes have not been verified in vitro and in humans.

As cell-based assessment systems of immune complex uptake, a method using cultured cells forcedly expressing antibody receptors and a method using primary cells taken from organs are known. With regard to the former, for example, uptake assessment of antibodies in cells such as macrophage cell line J774 (Non Patent Literature 21) and uptake assessment of immune complexes in MDCK cells (Patent Literature 5) are reported. Immune complex uptake assessment using hepatic nonparenchymal cells including LSECs taken from transgenic mice expressing human FcγRIIB is also reported (Patent Literature 3). However, these assessment methods are unlikely to correlate with in vivo immune complex elimination because overexpression of a certain protein in these assessment methods is greatly different from an environment within a living body. Moreover, it is reported that cellular activity changes over time in the latter use of primary cells (Non Patent Literature 22), and thus the latter may incorrectly reflect in vivo immune complex uptake.

As noted above, although immune complex pharmacokinetics have been assessed in vivo in mice, rats, and monkeys, in vitro assessment systems using cells involved in elimination of immune complexes, such as LSECs, have not been established. There are no reports that monkey or human cells have been used to quantitatively assess expression of FcγRIIB and cellular uptake of immune complexes.

It is suggested that nucleic acid-based pharmaceutical products are also mainly eliminated in hepatic nonparenchymal cells in a manner similar to immune complexes. It is reported that a $^3$H-labeled nucleic acid was intravenously administered to rats, and 40.5% accumulated in the liver, 60.4% of which accumulated in nonparenchymal cells (Non Patent Literature 26). Another report also demonstrated that accumulation in nonparenchymal cells was twice as much as that in parenchymal cells in mouse and rat (Non Patent Literature 27). Moreover, it is reported that FITC-labeled nucleic acids are incorporated into mouse LSECs in vitro (Non Patent Literature 25). Recently, it has been revealed that nucleic acids are incorporated by receptors, named Stabilin-1 and Stabilin-2 (Non Patent Literature 24).

CITATION LIST

Patent Literature

Patent Literature 1: WO 2012/132067 A1
Patent Literature 2: WO 2013/081143 A1
Patent Literature 3: WO 2014/113510 A1
Patent Literature 4: WO 2016/117346 A1
Patent Literature 5: WO 2016/098357 A1

Non Patent Literature

Non Patent Literature 1: Benacerraf, B., M. Sebestyen, and N. S. Cooper, The clearance of antigen antibody complexes from the blood by the reticuloendothelial system. J Immunol, 1959. 82(2): p. 131-7.
Non Patent Literature 2: Takai, T., Roles of Fc receptors in autoimmunity. Nat Rev Immunol, 2002. 2(8): p. 580-92.
Non Patent Literature 3: Schwab, I. and F. Nimmerjahn, Intravenous immunoglobulin therapy: how does IgG modulate the immune system? Nat Rev Immunol, 2013. 13(3): p. 176-89.
Non Patent Literature 4: Arend, W. P. and J. C. Sturge, Composition and biologic properties of soluble IgG-anti-IgG immune complexes: effects of variations in the specificity of rabbit antibodies to different structural components of human IgG. J Immunol, 1979. 123(1): p. 447-54.
Non Patent Literature 5: Finbloom, D. S. and P. H. Plotz, Studies of reticuloendothelial function in the mouse with model immune complexes. I. Serum clearance and tissue uptake in normal C3H mice. J Immunol, 1979. 123(4): p. 1594-9.
Non Patent Literature 6: Kurlander, R. J., D. M. Ellison, and J. Hall, The blockade of Fc receptor-mediated clearance of immune complexes in vivo by a monoclonal antibody (2.4G2) directed against Fc receptors on murine leukocytes. J Immunol, 1984. 133(2): p. 855-62.
Non Patent Literature 7: Mousavi, S. A., et al., Receptor-mediated endocytosis of immune complexes in rat liver sinusoidal endothelial cells is mediated by FcgammaRIIb2. Hepatology, 2007. 46(3): p. 871-84.
Non Patent Literature 8: Iwayanagi, Y., et al., Inhibitory FcgammaRIIb-Mediated Soluble Antigen Clearance from Plasma by a pH-Dependent Antigen-Binding Antibody and Its Enhancement by Fc Engineering. J Immunol, 2015. 195(7): p. 3198-205.
Non Patent Literature 9: Igawa, T., K. Haraya, and K. Hattori, Sweeping antibody as a novel therapeutic antibody modality capable of eliminating soluble antigens from circulation. Immunol Rev, 2016. 270(1): p. 132-51.
Non Patent Literature 10: Ganesan, L. P., et al., FcgammaRIIb on liver sinusoidal endothelium clears small immune complexes. J Immunol, 2012. 189(10): p. 4981-8.
Non Patent Literature 11: Lovdal, T., et al., Fc receptor mediated endocytosis of small soluble immunoglobulin G immune complexes in Kupffer and endothelial cells from rat liver. J Cell Sci, 2000. 113 (Pt 18): p. 3255-66.
Non Patent Literature 12: Rojas, J. R., et al., Formation, distribution, and elimination of infliximab and anti-infliximab immune complexes in cynomolgus monkeys. J Pharmacol Exp Ther, 2005. 313(2): p. 578-85.
Non Patent Literature 13: March, S., et al., Microenvironmental regulation of the sinusoidal endothelial cell phenotype in vitro. Hepatology, 2009. 50(3): p. 920-8.
Non Patent Literature 14: Filali, E. E., et al., Human liver endothelial cells, but not macrovascular or microvascular endothelial cells, engraft in the mouse liver. Cell Transplant, 2013. 22(10): p. 1801-11.
Non Patent Literature 15: Bruhns, P., et al., Specificity and affinity of human Fcgamma receptors and their polymorphic variants for human IgG subclasses. Blood, 2009. 113(16): p. 3716-25.
Non Patent Literature 16: Qiao, S. W., et al., Dependence of antibody-mediated presentation of antigen on FcRn. Proc Natl Acad Sci USA, 2008. 105(27): p. 9337-42.
Non Patent Literature 17: Weflen, A. W., et al., Multivalent immune complexes divert FcRn to lysosomes by exclusion from recycling sorting tubules. Mol Biol Cell, 2013. 24(15): p. 2398-405.
Non Patent Literature 18: Oitate, M., et al., Prediction of human pharmacokinetics of therapeutic monoclonal antibodies from simple allometry of monkey data. Drug Metab Pharmacokinet, 2011. 26(4): p. 423-30.
Non Patent Literature 19: Singh, A. P., et al., Quantitative prediction of human pharmacokinetics for mAbs exhibiting target-mediated disposition. Aaps j, 2015. 17(2): p. 389-99.
Non Patent Literature 20: Luu, K. T., et al., A model-based approach to predicting the human pharmacokinetics of a monoclonal antibody exhibiting target-mediated drug disposition. J Pharmacol Exp Ther, 2012. 341(3): p. 702-8.
Non Patent Literature 21: Mellman, I., H. Plutner, and P. Ukkonen, Internalization and rapid recycling of macrophage Fc receptors tagged with monovalent antireceptor antibody: possible role of a prelysosomal compartment. J Cell Biol, 1984.98(4): p. 1163-9.
Non Patent Literature 22: Pfeiffer, E., et al., Featured Article: Isolation, characterization, and cultivation of human hepatocytes and non-parenchymal liver cells. Exp Biol Med (Maywood), 2015. 240(5): p. 645-56.
Non Patent Literature 23: David Male, Jonathan Brostoff, David B Roth, and Ivan Roitt (translation supervised by Kiyoshi Takatsu, Hiroshi Kiyono, and Kensuke Miyake), Immunology, original 7$^{th}$ Edition, Nankodo, 2009 [in Japanese] Non Patent Literature 24: Miller CM., et al., Stabilin-1 and Stabilin-2 are specific receptors for the cellular internalization of phosphorothioate-modified antisense oligonucleotides (ASOs) in the liver. Nucleic Acids Res., 2016. 44(6): p. 2782-94.
Non Patent Literature 25: Martin-Armas M., et al., Toll-like receptor 9 (TLR9) is present in murine liver sinusoidal endothelial cells (LSECs) and mediates the effect of CpG-oligonucleotides. J Hepatol., 2006. 44(5):939-46.
Non Patent Literature 26: Nucleic Acids Res. 1997 Aug. 15; 25(16):3290-6

Non Patent Literature 27: Biochem Pharmacol. 2001 Aug. 1; 62(3):297-306
Non Patent Literature 28: Deleve, L. D., J Clin Invest. 2013 123(5):1861-6
Non Patent Literature 29: J Hepatol. 2017 January; 66(1): 212-227

SUMMARY OF INVENTION

Technical Problem

As mentioned above, although there are no in vitro cell quantitative assessment systems that mimic an environment within a living body, such assessment systems, unlike animal experiments, have advantages of feasibility of more detailed analyses of mechanisms, kinetics assessments of cellular uptake or the like, and screening of many candidate substances, and may serve as a tool useful for life science research and drug discovery research as well as cellular uptake analysis of immune complexes.

For FcγRIIB, affinity of its recombinant protein to the Fc region of antibodies has been measured with Biacore (GE Healthcare) or similar substances (Non Patent Literature 15). That is because the binding of immune complexes to cells and cellular uptake of immune complexes are mediated by FcγRIIB, and thus the affinity to FcγRIIB can be important for immune complex elimination from plasma. However, affinity measurement with Biacore as mentioned above is difficult when antibodies that non-specifically adsorb or are highly electrically charged are used. The measurements in buffers with recombinant proteins are also unlikely to correctly reflect affinity in plasma in vivo. It is also suggested that in addition to binding to FcγRIIB, binding to other receptors is involved in immune complex uptake. For example, it is reported that neonatal Fc receptor (FcRn) is also involved in immune complex elimination (Non Patent Literatures 16 and 17).

Pharmacokinetic analysis, which describes drug action in a living body using a mathematical model, is useful for saving of experimental animals and increasing efficiency of clinical trials. It is possible to predict clinical change in drug concentration from nonclinical change in drug concentration by scaling parameters obtained in nonhuman animals to human using mathematical models based on an empirical rule (see, e.g., Non Patent Literature 18). Mathematical models based on the mechanism describing drug elimination via receptors includes, for example, Target-mediated drug disposition model (see, e.g., Non Patent Literatures 19 and 20). These models describe binding of a receptor to a drug and cellular uptake via the receptor. It is known that the amino acid sequence of FcγRIIB has species difference. As mentioned above, it is suggested that binding to receptors other than FcγRIIB is involved in immune complex uptake. Thus, to quantitatively predict pharmacokinetics of immune complex-forming drugs in humans, scaling the change in drug concentration obtained from nonhuman animals to that in humans based on an empirical rule is inadequate. Thus, it is required to calculate parameters suitable for individual animal species. To achieve this calculation, quantitative kinetics and assessment of receptor expression levels using a cell system are required.

Moreover, screening a large number of drug candidate substances only in animal experiments has problems of requiring a large amount of labor and many experimental animals such as monkey. Also, in animal experiments, it is impossible to quantify expression of FcγRIIB and binding and uptake of immune complexes in cells such as LSECs.

Also, as mentioned above, use of cultured cells forcedly expressing antibody receptors and use of primary cells taken from organs, known as cell-based assessment systems may incorrectly reflect in vivo immune complex uptake.

For these reasons, there is a need to develop cell-based in vitro assessment systems that mimic in vivo immune complex elimination and can quantify FcγRIIB expression and binding and uptake of an antibody or antigen.

Solution to Problem

There is a report that hepatic nonparenchymal cells taken from a transgenic mouse expressing human FcγRIIB were used to examine uptake of immune complexes into $CD146^+$ $CD45^{low}$ LSECs (Patent Literature 3). However, as mentioned above, molecules involved in immune complex uptake are not limited to FcγRIIB, and thus it is extremely difficult to establish an in vitro assessment system that reflects human or monkey biophenomena in mouse cells. Even if immune complex uptake can be observed in assessment systems forcedly expressing FcγRIIB, immune complex uptake cannot necessarily be assessed as in nontransgenic cells.

The present inventors have conducted diligent studies and finally have found that human and monkey hepatic nonparenchymal cells can be separated into a plurality of $CD31^+$ $CD45^+$ cell populations, using the expression levels of cell surface markers CD31 and CD45 as an index, and that one of all the populations is an FcγRIIB-expressing cell population. CD31 and CD45 are known to be a LSEC marker in human (Non Patent Literatures 28 and 29), but it is not known at all that FcγRIIB is specifically expressed in some of $CD31^+$ $CD45^+$ cell populations. Also, CD31 and CD45 are not known to be a LSEC marker in monkey. The present inventors have successfully established an assessment system to measure an uptake amount of immune complexes in this FcγRIIB-expressing cell population. The present inventors have further successfully established an assessment system to measure an uptake amount of nucleic acids in the cell population, an assessment system to measure an uptake amount of antibody itself via FcγRIIB into the cell population, and an assessment system to measure an uptake amount of antibodies bound to membrane-type receptors expressed in the cell population. The present inventors have further conducted studies, leading to completion of the present invention.

More specifically, the present invention provides the following inventions:

[1] A method for measuring a cellular uptake amount of a molecule, comprising the steps of:
(i) adding the molecule to an organ-derived cell population to perform incubation,
(ii) sorting the organ-derived cell population based on expression levels of CD31 and CD45, and
(iii) after steps (i) and (ii), measuring the amount of the molecule incorporated into the cell population, wherein the molecule is incorporated into cells via a cell surface receptor.

[2] The method according to [1], wherein the method comprises step (ii) subsequent to step (i), and the organ-derived cell population incubated with the added molecule is sorted based on the expression levels of CD31 and CD45.

[3] The method according to [1], wherein the method comprises step (ii) prior to step (i), and the molecule is added to the organ-derived cell population sorted based on the expression levels of CD31 and CD45 to perform incubation.

[4] The method according to any of [1] to [3], wherein the molecule is an immune complex or an antibody, and the receptor is an Fc receptor.

[5] The method according to any of [1] to [3], wherein the molecule is an anti-IL-6R antibody, and the receptor is IL-6R.

[6] The method according to any of [1] to [3], wherein the molecule is a nucleic acid, and the receptor is Stabilin.

[7] The method according to any of [1] to [6], wherein the organ-derived cell population is a hepatic nonparenchymal cell population.

[8] The method according to [7], wherein the hepatic nonparenchymal cell population is a human hepatic nonparenchymal cell population, and a CD31high CD45low cell population is sorted in step (ii).

[9] The method according to [8], wherein the CD31high CD45low cell population is one of two CD31+CD45+ cell populations distinguishable from each other based on the cell density in the scatter diagram in which the expression levels of CD31 and CD45 obtained by measuring expressions of CD31 and CD45 by flow cytometry are plotted on the X-axis and Y-axis respectively, and the CD31high CD45low cell population has a high expression level of CD31 compared with the other CD31+CD45+ cell population when the expression levels of CD31 are compared at the highest cell density in each cell population.

[10] The method according to [8], wherein the CD31high CD45low cell population is a cell population having a fluorescence intensity of CD31 ranging from 400 to 7000 and a fluorescence intensity of CD45 ranging from 100 to 4000 in the detection of CD31 and CD45 expressions by flow cytometry.

[11] The method according to [7], wherein the hepatic nonparenchymal cell population is a monkey hepatic nonparenchymal cell population, and the CD31 intermediate CD45intermediate cell population is sorted in step (ii).

[12] The method according to [11], wherein the CD31 intermediate CD45intermediate cell population is one of three CD31+CD45+ cell populations distinguishable from one another based on the cell density in the scatter diagram in which the expression levels of CD31 and CD45 obtained by measuring expressions of CD31 and CD45 by flow cytometry are plotted on the X-axis and Y-axis respectively, and the CD31 intermediate CD45intermediate cell population has the second highest expression level of CD31 among the three cell populations when the expression levels of CD31 are compared at the highest cell density in each cell population.

[13] The method according to [11], wherein the CD31 intermediate CD45intermediate cell population is a cell population having a fluorescence intensity of CD31 ranging from 500 to 3000 and a fluorescence intensity of CD45 ranging from 4000 to 20000 in the detection of CD31 and CD45 expressions by flow cytometry.

[14] A composition for an uptake assay of a molecule, wherein the composition comprises an isolated organ-derived cell population that expresses CD31 and CD45, and the molecule is incorporated into cells via a cell surface receptor.

[15] The composition according to [14], wherein the assay is performed using the method according to any of [1] to [13].

[16] The composition according to [14] or [15], wherein the cell population is partially purified.

[17] A method for producing the composition according to any of [14] to [16], comprising the steps of:
(i) preparing organ-derived cells from an organ removed from a living body, and
(ii) sorting the organ-derived cells based on expression levels of CD31 and CD45.

[18] A method for predicting an in vivo elimination clearance of a molecule, comprising the steps of:
(i) measuring a cellular uptake amount of the molecule using the method according to any of [1] to [13], and
(ii) predicting the in vivo elimination clearance of the molecule upon administration to a living body, based on the uptake amount measured in the step (i),
wherein the molecule is incorporated into cells via a cell surface receptor.

[19] A method for screening for a molecule, comprising the steps of:
(i) providing two or more different molecules that bind to an identical receptor,
(ii) measuring a cellular uptake amount of each of the molecules provided in the step (i) using the method according to any of [1] to [13], and
(iii) mutually comparing the cellular uptake amounts of the molecules measured in the step (ii) to select the molecule that has the highest uptake amount,
wherein the molecule is incorporated into cells via a cell surface receptor.

[20] The method according to any of [1] to [7], wherein the organ-derived cell population is a human hepatic nonparenchymal cell population, and the cell population indicated by P2 in FIG. 8 is sorted in the step (ii).

[21] The method according to any of [1] to [7], wherein the organ-derived cell population is a monkey hepatic nonparenchymal cell population, and the cell population indicated by P2 in FIG. 2 is sorted in the step (ii).

[22] The composition according to any of [14] to [16], wherein the organ-derived cell population is a human hepatic nonparenchymal cell population and consists of the cell population indicated by P2 in FIG. 8.

[23] The composition according to any of [14] to [16], wherein the organ-derived cell population is a monkey hepatic nonparenchymal cell population and consists of the cell population indicated by P2 in FIG. 2.

The present invention also includes inventions of the following aspects:

[a1] A method for measuring a cellular uptake amount of an immune complex, comprising the steps of
(i) adding the immune complex to an organ-derived cell population to perform incubation,
(ii) sorting the organ-derived cell population based on the expression levels of CD31 and CD45, and
(iii) after steps (i) and (ii), measuring the amount of the immune complex incorporated into the cell population.

[a2] The method according to [a1], wherein the method comprises step (ii) subsequent to step (i), and the organ-derived cell population incubated with the added immune complex is sorted based on the expression levels of CD31 and CD45.

[a3] The method according to [a1], wherein the method comprises step (ii) prior to step (i), and the immune complex is added to the organ-derived cell population sorted based on the expression levels of CD31 and CD45 to perform incubation.

[a4] The method according to any of [a1] to [a3], wherein the immune complex is incorporated into cells via FcγRIIB.

[a5] The method according to any of [a1] to [a4], wherein the organ-derived cell population is a hepatic nonparenchymal cell population.

[a6] The method according to [a5], wherein the hepatic nonparenchymal cell population is a human hepatic nonparenchymal cell population, and a CD31high CD45low cell population is sorted in step (ii).

[a7] The method according to [a6], wherein the CD31high CD45low cell population is one of two CD31+CD45+ cell populations distinguishable from each other based on the cell density in the scatter diagram in which the expression levels of CD31 and CD45 obtained by measuring expressions of CD31 and CD45 by flow cytometry are plotted on the X-axis and Y-axis respectively, and the CD31high CD45low cell population has a high expression level of CD31 compared with the other CD31+CD45+ cell population when the expression level of CD31 is compared at the highest cell density in each cell population.

[a8] The method according to [a6], wherein the CD31high CD45low cell population is a cell population having a fluorescence intensity of CD31 ranging from 400 to 7000 and a fluorescence intensity of CD45 ranging from 100 to 4000 in the detection of CD31 and CD45 expressions by flow cytometry.

[a9] The method according to [a5], wherein the hepatic nonparenchymal cell population is a monkey hepatic nonparenchymal cell population, and the CD31 intermediate CD45intermediate cell population is sorted in step (ii).

[a10] The method according to [a9], wherein the CD31 intermediate CD45intermediate cell population is one of three CD31+CD45+ cell populations distinguishable from one another based on the cell density in the scatter diagram in which the expression levels of CD31 and CD45 obtained by measuring expressions of CD31 and CD45 by flow cytometry are plotted on the X-axis and Y-axis respectively, and the CD31 intermediate CD45intermediate cell population has the second highest expression level of CD31 among the three cell populations when the expression level of CD31 is compared at the highest cell density in each cell population.

[a11] The method according to [a9], wherein the CD3intermediate CD45intermediate cell population is a cell population having a fluorescence intensity of CD31 ranging from 500 to 3000 and a fluorescence intensity of CD45 ranging from 4000 to 20000 in the detection of CD31 and CD45 expressions by flow cytometry.

[a12] A composition for an uptake assay of an immune complex, wherein the composition comprises an isolated organ-derived cell population that expresses CD31 and CD45.

[a13] The composition according to [a12], wherein the assay is performed using the method according to any of [a1] to [a11].

[a14] The composition according to [a12] or [a13], wherein the cell population is a partially purified cell population.

[a15] A method for producing the composition according to any of [a12] to [a14], comprising the steps of (i) preparing organ-derived cells from an organ removed from a living body, and
(ii) sorting the organ-derived cells based on the expression levels of CD31 and CD45.

[a16] A method for predicting an in vivo reduction rate of an antigen in a blood upon administration of an antibody, comprising the steps of
(i) forming an immune complex from the antigen and the antibody,
(ii) measuring a cellular uptake amount of the immune complex formed in the step (i) using the method according to any of [a1] to [a11], and
(iii) predicting the in vivo reduction rate of the antigen in the blood upon administration of the antibody to a living body, based on the uptake amount measured in the step (ii).

[a17] A method for screening for an antibody having an antigen clearance function, comprising the steps of
(i) providing two or more different antibodies that bind to an identical antigen,
(ii) providing an immune complex containing the antigen and each of the two or more antibodies provided in the step (i),
(iii) measuring a cellular uptake amount of each of the immune complexes provided in the step (ii) using the method according to any of [a1] to [a11], and
(iv) mutually comparing the cellular uptake amounts of the immune complexes measured in the step (iii) to select the immune complex that has the highest uptake amount.

[a18] The method according to any of [a1] to [a5], wherein the organ-derived cell population is a human hepatic nonparenchymal cell population, and the cell population indicated by P2 in FIG. 8 is sorted in the step (ii).

[a19] The method according to any of [a1] to [a5], wherein the organ-derived cell population is a monkey hepatic nonparenchymal cell population, and the cell population indicated by P2 in FIG. 2 is sorted in the step (ii).

[a20] The composition according to [a12], wherein the organ-derived cell population is a human hepatic nonparenchymal cell population and consists of the cell population indicated by P2 in FIG. 8.

[a21] The composition according to [a12], wherein the organ-derived cell population is a monkey hepatic nonparenchymal cell population and consists of the cell population indicated by P2 in FIG. 2.

The present invention also includes inventions of the following aspects:

[b1] A method for measuring a cellular uptake amount of an antibody, comprising the steps of:
(i) adding the antibody to an organ-derived cell population to perform incubation,
(ii) sorting the organ-derived cell population based on the expression levels of CD31 and CD45, and
(iii) after steps (i) and (ii), measuring the amount of the antibody incorporated into the cell population,
wherein the antibody binds to a soluble antigen.

[b2] The method according to [b1], wherein the method comprises step (ii) subsequent to step (i), and the organ-derived cell population incubated with the added antibody is sorted based on the expression levels of CD31 and CD45.

[b3] The method according to [b1], wherein the method comprises step (ii) prior to step (i), and the antibody is added to the organ-derived cell population sorted based on the expression levels of CD31 and CD45 to perform incubation.

[b4] The method according to any of [b1] to [b3], wherein the antibody is incorporated into cells via an Fc receptor.

[b5] The method according to any of [b1] to [b4], wherein the organ-derived cell population is a hepatic nonparenchymal cell population.

[b6] The method according to [b5], wherein the hepatic nonparenchymal cell population is a human hepatic nonparenchymal cell population, and a CD31 high CD45low cell population is sorted in step (ii).

[b7] The method according to [b6], wherein the CD31 high CD45low cell population is one of two CD31+ CD45+ cell populations distinguishable from each other based on the cell density in the scatter diagram in which the expression levels of CD31 and CD45 obtained by measuring expressions of CD31 and CD45 by flow cytometry are plotted on the X-axis and Y-axis respectively, and the CD31high CD45low cell population has a high expression level of CD31 compared with the other CD31+CD45+ cell population when the expression level of CD31 is compared at the highest cell density in each cell population.

[b8] The method according to [b6], wherein the CD31high CD45low cell population is a cell population having a fluorescence intensity of CD31 ranging from 400 to 7000 and a fluorescence intensity of CD45 ranging from 100 to 4000 in the detection of CD31 and CD45 expressions by flow cytometry.

[b9] The method according to [b5], wherein the hepatic nonparenchymal cell population is a monkey hepatic nonparenchymal cell population, and the CD31 intermediate CD45intermediate cell population is sorted in step (ii).

[b10] The method according to [b9], wherein the CD3intermediate CD45intermediate cell population is one of three CD31+CD45+ cell populations distinguishable from one another based on the cell density in the scatter diagram in which the expression levels of CD31 and CD45 obtained by measuring expressions of CD31 and CD45 by flow cytometry are plotted on the X-axis and Y-axis respectively, and the CD31 intermediate CD45intermediate cell population has the second highest expression level of CD31 among the three cell populations when the expression level of CD31 is compared at the highest cell density in each cell population.

[b11] The method according to [b9], wherein the CD31intermediate CD45intermediate cell population is a cell population having a fluorescence intensity of CD31 ranging from 500 to 3000 and a fluorescence intensity of CD45 ranging from 4000 to 20000 in the detection of CD31 and CD45 expressions by flow cytometry.

[b12] A composition for an uptake assay of an antibody, wherein the composition comprises an isolated organ-derived cell population that expresses CD31 and CD45, and the antibody binds to a soluble antigen.

[b13] The composition according to [b12], wherein the assay is performed using the method according to any of [b1] to [b11].

[b14] The composition according to [b12] or [b13], wherein the cell population is a partially purified cell population.

[b15] A method for producing the composition according to any of [b12] to [b14], comprising the steps of
(i) preparing organ-derived cells from an organ removed from a living body, and
(ii) sorting the organ-derived cells based on the expression levels of CD31 and CD45.

[b16] A method for predicting an in vivo elimination clearance of an antibody, comprising the steps of
(i) measuring a cellular uptake amount of the antibody of interest using the method according to any of [b1] to [b11], and
(ii) predicting the in vivo elimination clearance of the antibody upon administration of the antibody to a living body, based on the uptake amount measured in the step (i),
wherein the antibody binds to a soluble antigen.

[b17] A method for screening for an antibody, comprising the steps of:
(i) providing two or more different antibodies that bind to an identical soluble antigen,
(ii) measuring a cellular uptake amount of each of the antibodies provided in the step (i) using the method according to any of [b1] to [b11], and
(iii) mutually comparing the intracellular uptake amounts of the antibodies measured in the step (ii) to select the antibody that has the highest uptake amount.

[b18] The method according to any of [b1] to [b5], wherein the organ-derived cell population is a human hepatic nonparenchymal cell population, and the cell population indicated by P2 in FIG. 8 is sorted in the step (ii).

[b19] The method according to any of [b1] to [b5], wherein the organ-derived cell population is a monkey hepatic nonparenchymal cell population, and the cell population indicated by P2 in FIG. 2 is sorted in the step (ii).

[b20] The composition according to [b12], wherein the organ-derived cell population is a human hepatic nonparenchymal cell population and consists of the cell population indicated by P2 in FIG. 8.

[b21] The composition according to [b12], wherein the organ-derived cell population is a monkey hepatic nonparenchymal cell population and consists of the cell population indicated by P2 in FIG. 2.

The present invention also includes inventions of the following aspects:

[c1] A method for measuring a cellular uptake amount of an antibody, comprising the steps of:
(i) adding the antibody to an organ-derived cell population to perform incubation,
(ii) sorting the organ-derived cell population based on the expression levels of CD31 and CD45, and
(iii) after steps (i) and (ii), measuring the amount of the antibody incorporated into the cell population,
wherein the antibody binds to a membrane-type receptor.

[c2] The method according to [c1], wherein the method comprises step (ii) subsequent to step (i), and the organ-derived cell population incubated with the added antibody is sorted based on the expression levels of CD31 and CD45.

[c3] The method according to [c1], wherein the method comprises step (ii) prior to step (i), and the antibody is added to the organ-derived cell population sorted based on the expression levels of CD31 and CD45 to perform incubation.

[c4] The method according to any of [c1] to [c3], wherein the antibody is incorporated into cells via the membrane-type receptor.

[c5] The method according to any of [c1] to [c4], wherein the antibody is an anti-IL-6R antibody, and the membrane-type receptor is IL-6R.

[c6] The method according to any of [c1] to [c5], wherein the organ-derived cell population is a hepatic nonparenchymal cell population.

[c7] The method according to [c6], wherein the hepatic nonparenchymal cell population is a human hepatic nonparenchymal cell population, and a CD31 high CD45low cell population is sorted in step (ii).

[c8] The method according to [c7], wherein the CD3high CD45low cell population is one of two CD31+CD45+ cell populations distinguishable from each other based on the cell density in the scatter diagram in which the expression levels of CD31 and CD45 obtained by measuring expressions of CD31 and CD45 by flow cytometry are plotted on the X-axis and Y-axis respectively, and the CD31high CD45low cell population has a high expression level of CD31 compared with the other CD31+CD45+ cell population when the expression level of CD31 is compared at the highest cell density in each cell population.

[c9] The method according to [c7], wherein the CD31high CD45low cell population is a cell population having a fluorescence intensity of CD31 ranging from 400 to 7000 and a fluorescence intensity of CD45 ranging from 100 to 4000 in the detection of CD31 and CD45 expressions by flow cytometry.

[c10] The method according to [c6], wherein the hepatic nonparenchymal cell population is a monkey hepatic nonparenchymal cell population, and the CD31intermediate CD45intermediate cell population is sorted in step (ii).

[c11] The method according to [c10], wherein the CD31intermediate CD45intermediate cell population is one of three CD31+CD45+ cell populations distinguishable from one another based on the cell density in the scatter diagram in which the expression levels of CD31 and CD45 obtained by measuring expressions of CD31 and CD45 by flow cytometry are plotted on the X-axis and Y-axis respectively, and the CD31 intermediate CD45intermediate cell population has the second highest expression level of CD31 among the three cell populations when the expression level of CD31 is compared at the highest cell density in each cell population.

[c12] The method according to [c10], wherein the CD31intermediate CD45intermediate cell population is a cell population having a fluorescence intensity of CD31 ranging from 500 to 3000 and a fluorescence intensity of CD45 ranging from 4000 to 20000 in the detection of CD31 and CD45 expressions by flow cytometry.

[c13] A composition for an uptake assay of an antibody, wherein the composition comprises an isolated organ-derived cell population that expresses CD31 and CD45, and the antibody binds to a membrane-type receptor.

[c14] The composition according to [c13], wherein the assay is performed using the method according to any of [c1] to [c12].

[c15] The composition according to [c13] or [c14], wherein the cell population is a partially purified cell population.

[c16] A method for producing the composition according to any of [c13] to [c15], comprising the steps of:
(i) preparing organ-derived cells from an organ removed from a living body, and
(ii) sorting the organ-derived cells based on the expression levels of CD31 and CD45.

[c17] A method for predicting an in vivo elimination clearance of an antibody, comprising the steps of:
(i) measuring a cellular uptake amount of the antibody using the method according to any of [c1] to [c12], and
(ii) predicting the in vivo elimination clearance of the antibody upon administration of the antibody to a living body, based on the uptake amount measured in the step (i),
wherein the antibody binds to a membrane-type receptor.

[c18] A method for screening for an antibody, comprising the steps of:
(i) providing two or more different antibodies that bind to an identical antigen,
(ii) measuring a cellular uptake amount of each of the antibodies provided in the step (i) using the method according to any of [c1] to [c12], and
(iii) mutually comparing the cellular uptake amounts of the antibodies measured in the step (ii) to select the antibody that has the highest uptake amount,
wherein the antibody binds to a membrane-type receptor.

[c19] The method according to any of [c1] to [c6], wherein the organ-derived cell population is a human hepatic nonparenchymal cell population, and the cell population indicated by P2 in FIG. 8 is sorted in the step (ii).

[c20] The method according to any of [c1] to [c6], wherein the organ-derived cell population is a monkey hepatic nonparenchymal cell population, and the cell population indicated by P2 in FIG. 2 is sorted in the step (ii).

[c21] The composition according to [c13], wherein the organ-derived cell population is a human hepatic nonparenchymal cell population and consists of the cell population indicated by P2 in FIG. 8.

[c22] The composition according to [c13], wherein the organ-derived cell population is a monkey hepatic nonparenchymal cell population and consists of the cell population indicated by P2 in FIG. 2.

The present invention also includes inventions of aspects according to an in vitro assessment system that relates to nucleic acid uptake. As in vitro assessment systems of cellular uptake of nucleic acids, a method using cultured cells forcedly expressing receptors and a method using primary cells taken from organs as well as the assessment systems of immune complex uptake are known. As the former, for example, nucleic acid uptake assessment systems that uses HEK-293 cells forcedly expressing Stabilin-1 and Stabilin-2 known as a nucleic acid receptor are known (Non Patent Literature 24). However, these methods are unlikely to correlate with in vivo nucleic acid uptake because overexpression of a certain protein will make a situation greatly different from an environment within a living body. The latter which is use of primary cells taken from organs include assessment of the isolated rat (Non Patent Literature 25) and mouse (Non Patent Literature 24) LSECs. However, this assessment has problems of change of cellular activity over time.

It is also unknown whether nucleic acid uptake in monkeys or humans is reflected in systems using rat and mouse cells.

To solve these problems, the present inventors have conducted diligent studies and successfully established a system that can assess in vivo nucleic acid uptake by establishing an assessment system using organ-derived cells in a similar way to the assessment system that quantitatively measures immune complex uptake as mentioned above.

More specifically, the present invention includes inventions of the following aspects:

[A1] A method for measuring a cellular uptake amount of a nucleic acid, comprising the steps of:
(i) adding the nucleic acid to an organ-derived cell population to perform incubation,
(ii) sorting the organ-derived cell population that expresses Stabilin (nucleic acid uptake receptor), and
(iii) after steps (i) and (ii), measuring the amount of the nucleic acid incorporated into the cell population.

[A2] The method according to [A1], wherein the method comprises step (ii) subsequent to step (i), and the organ-derived cell population incubated with the added nucleic acid is sorted for a cell population expressing Stabilin.

[A3] The method according to [A1], wherein the method comprises step (ii) prior to step (i), and the nucleic acid is added to the sorted organ-derived cell population expressing Stabilin to perform incubation.

[A4] The method according to any of [A1] to [A3], wherein the cell population sorted in the step (ii) expresses CD31 and CD45.

[A5] The method according to any of [A1] to [A4], wherein the organ-derived cell population is a hepatic nonparenchymal cell population.

[A6] A composition for an uptake assay of a nucleic acid, wherein the composition comprises an isolated organ-derived cell population that expresses Stabilin.

[A7] The composition according to [A6], wherein the assay is performed using the method according to any of [A1] to [A5].

[A8] The composition according to [A6] or [A7], wherein the cell population is a partially purified cell population.

[A9] A method for producing the composition according to any of [A6] to [A8], comprising the steps of:
(i) preparing organ-derived cells from an organ removed from a living body, and
(ii) sorting the organ-derived cell population expressing Stabilin.

[A10] A method for screening for a nucleic acid, comprising the steps of:
(i) providing two or more nucleic acids that have an identical nucleotide sequence and each have a different chemical modification,
(ii) measuring a cellular uptake amount of each of the two or more nucleic acids provided in the step (i) using the method according to any of [A1] to [A5], and
(iii) mutually comparing the cellular uptake amounts of the nucleic acids measured in the step (ii) to select the nucleic acid that has the desired uptake amount.

[A11] The method according to any of [A1] to [A5], wherein the organ-derived cell population is a human hepatic nonparenchymal cell population, and the cell population indicated by P1 or P2 in FIG. 8 is sorted in the step (ii).

[A12] The method according to any of [A1] to [A5], wherein the organ-derived cell population is a monkey hepatic nonparenchymal cell population, and the cell population indicated by any of P1, P2, and P3 in FIG. 2 is sorted in the step (ii).

[A13] The composition according to [A6], wherein the organ-derived cell population is a human hepatic nonparenchymal cell population and consists of the cell population indicated by P2 in FIG. 8.

[A14] The composition according to [A6], wherein the organ-derived cell population is a monkey hepatic nonparenchymal cell population and consists of the cell population indicated by any of P1, P2, and P3 in FIG. 2.

Advantageous Effects of Invention

The method for measuring a cellular uptake amount of a molecule incorporated into cells via a cell surface receptor of the present invention correctly reflects in vivo cellular uptake of the molecule and can precisely predict an in vivo kinetics of the molecule compared with conventional measurement methods.

The method for measuring a cellular uptake amount of an immune complex of the present invention also correctly reflects in vivo cellular uptake of the immune complex compared with conventional measurement methods. The results obtained from the present invention highly correlate with in vivo reduction rates of antigens in the plasma. Therefore, the present invention efficiently selects antibodies capable of efficiently eliminating immune complexes in vivo, and also contributes to saving of animal experiments such as using monkey. Moreover, data obtained from the measurement method of the present invention contributes to establishment of pharmacokinetics models that can predict in vivo change in antibody and antigen concentrations.

The method for measuring a cellular uptake amount of nucleic acids of the present invention can efficiently screen for nucleic acid-based pharmaceutical products that have improved cellular uptake in the research and development of the nucleic acid-based pharmaceutical products.

DESCRIPTION OF EMBODIMENTS

Figure 1:
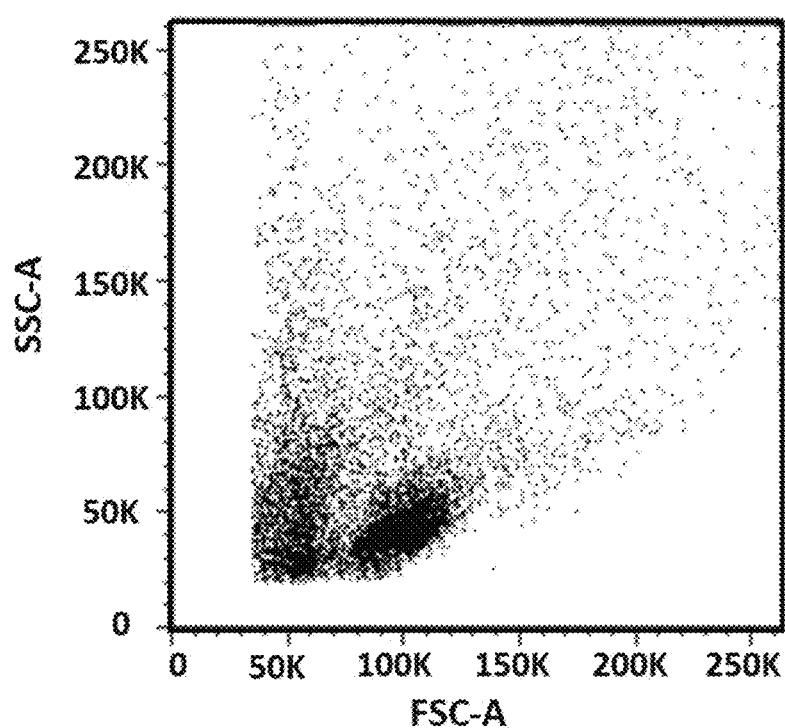
FIG. 1 is a scatter diagram showing the cell distribution analyzed based on forward-scattered light (FSC) and side-scattered light (SSC) detected in a flow cytometer which monkey hepatic nonparenchymal cells were flowed through, as described in Example 3. In the measurement in FACS Canto II, data was acquired and plotted from 20000 cells without debris.

I. Cellular Uptake of a Molecule Incorporated into Cells Via a Cell Surface Receptor I-1. Method for Measuring a Cellular Uptake Amount of a Molecule Incorporated into Cells Via a Cell Surface Receptor The first aspect of the present invention relates to a method for measuring a cellular uptake amount of a molecule incorporated into cells via a cell surface receptor (hereinafter also referred to as Measurement Method I of the present invention).

In the present invention, the "molecule incorporated into cells via a cell surface receptor" refers to a molecule that binds to a receptor present on the surface of cells included in an organ-derived cell population mentioned later to be incorporated into the cells via the receptor. The molecule incorporated into the cells may be a single molecule or a complex consisting of two or more molecules. The "molecule incorporated into cells via a cell surface receptor" may be a structure or substance consisting of a great number of molecules. Examples of the molecule include, but are not limited to, an antibody-antigen complex (immune complex), which is a molecule described in the Examples, a nucleic acid, an antibody that binds to a soluble antigen, and an antibody that binds to a membrane-type receptor, as well as DDS formulations such as a peptide compound, toxin, virus, nanoparticle, or microparticle.

The measurement method of the present invention can assess the cellular uptake amounts of these molecules and can predict in vivo kinetics of these molecules in a manner similar to that described in the Examples of the present application.

In the present invention, the "immune complex" refers to a complex that comprises an antibody and an antigen and is formed by binding of at least one antibody to at least one antigen. In one aspect, an immune complex consisting of an antibody and an antigen can be used interchangeably with an antigen-antibody conjugate.

In the present specification, the "antibody" refers to a natural immunoglobulin or an immunoglobulin produced through partial or total synthesis. The antibody may be isolated from a natural resource (e.g., plasma or serum containing naturally occurring antibodies) or the culture supernatant of antibody-producing hybridoma cells or may be partially or totally synthesized by use of a technique such as gene recombination. Preferred examples of the antibody include isotypes of immunoglobulins (i.e., IgG, IgA, IgD, IgE, and IgM) and subclasses of these isotypes. Nine subclasses, i.e., IgG1, IgG2, IgG3, IgG4, IgA1, IgA2, IgD, IgE, and IgM, are known as human immunoglobulins. In a preferred aspect, an antibody making up an immune complex in the Measurement Method I of the present invention is IgG.

The antibody may be a polyclonal or monoclonal antibody. In the present invention, a genetically recombinant antibody, for example, a chimeric or humanized antibody, which is artificially altered for the purpose of, for example, reducing hetero-antigenicity can be used. The antibody may also be a bispecific antibody.

The antibody may be a fragment of an antibody as long as the fragment comprises an "antigen-binding domain" and an "Fc receptor-binding domain". The "antigen-binding domain" of an antibody may be a domain that binds to an antigen of interest, for example, a variable region of a heavy or light chain of an antibody. The "Fc receptor-binding domain" of an antibody may be a domain that binds to an Fc receptor, for example, a constant (Fc) region of an antibody. Examples of the Fc receptor include FcγR and FcRn. FcγR may be preferably FcγRII, and more preferably FcγRIIB.

Methods for producing these antibodies are known to those skilled in the art (see, e.g., WO 2013/081143).

In the present specification, the "antigen" is not limited to a particular structure as long as the antigen comprises an epitope bound by an antigen-binding domain. In another sense, the antigen may be an inorganic or organic substance. Examples of the antigen can include the following molecules: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic factor, av/b3 integrin, Axl, b2M, B7-1, B7-2, B7-H, B-lymphocyte-stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3(C3), C3a, C4, C5, C5a, C10, CA125, CAD-8, calcitonin, cAMP, carcinoembryonic antigen (CEA), cancer-associated antigen, cathepsin A, cathepsin B, cathepsin C/DPPI, cathepsin D, cathepsin E, cathepsin H, cathepsin L, cathepsin 0, cathepsin S, cathepsin V, cathepsin X/Z/P, CBL, CCI, CCK2, CCL, CCL, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast-activating protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle-stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha 1, GFR-alpha 2, GFR-alpha 3, GITR, glucagon, Glut4, glycoprotein IIb/IIIa (GPIIb/IIIa), GM-CSF, gp130, gp72, GRO, growth hormone-releasing factor, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high-molecular-weight melanoma-associated antigen (HMW-MAA), HIV gp120, HIV IIIB gp 120 V3 loop, HLA, HLA-DR, HM1.24, HMFG PEM, HRG, Hrk, human heart myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF-binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor 1, integrin alpha 2, integrin alpha 3, integrin alpha 4, integrin alpha 4/beta 1, integrin alpha 4/beta 7, integrin alpha 5 (alpha V), integrin alpha 5/beta 1, integrin alpha 5/beta 3, integrin alpha 6, integrin beta 1, integrin beta 2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bpI, LBP, LDGF, LECT2, lefty, Lewis-Y antigen, Lewis-Y-related antigen, LFA-1, LFA-3, Lfo, LIF, LIGHT, lipoprotein, LIX, LKN, Lptn, L-selectin, LT-a, LT-b, LTB4, LTBP-1, lung surfactant, luteinizing hormone, lymphotoxin beta receptor, Mac-1, MAdCAM, MAG, MAP2, MARC, MCAM, MCAM, MCK-2, MCP, M-CSF, MDC, Mer, metalloproteases, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, mullerian-inhibiting factor, Mug, MuSK, NAIP, NAP, NCAD, N-cadherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), PGF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, rheumatoid factor, RLIP76, RPA2, RSK, S100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T cell receptor (e.g., T cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta 1, TGF-beta 2, TGF-beta 3, TGF-beta 4, TGF-beta 5, thrombin, thymus Ck-1, thyroid stimulating hormone, Tie, TIMP, TIQ, tissue factor, TMEFF2, Tmpo, TMPRSS2, TNF, TNF-alpha, TNF-alpha/beta, TNF-beta 2, TNFc, TNF-RI, TNF-RII, TNFRSF10A (TRAIL RI Apo-2, DR4), TNFRSF10B (TRAIL R2 DR5, KILLER, TRICK-2A, TRICK-B), TNFRSF10C (TRAIL R3 DcRT, LIT, TRID), TNFRSF10D (TRAIL R4 DcR2, TRUNDD), TNFRSF1A (RANK ODF R, TRANCE R), TNFRSF1 TB (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH), TNFRSF25 (DR3 Apo-3, LARD, TR-3, TRAMP, WSL-1), TNFSF10 (TRAIL Apo-2ligand, TL2), TNFSFT (TRANCE/RANK ligand ODF, OPG ligand), TNFSFT2 (TWEAK Apo-3 ligand, DR3 ligand), TNFSFT3 (APRIL TALL2), TNFSF13B (BAFF BLYS, TALL1, THANK, TNFSF20), TNFSF4 (LIGHT HVEM ligand, LTg), TNFSF15 (TLA/VEGI), TNFSF8 (GITR ligand AITR ligand, TL6), TNFSFTA (TNF-α conectin, DIF, TNFSF2), TNFSFB (TNF-b LTa, TNFSF), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R, TRAIL-R2, TRANCE, transferrin receptor, TRF, Trk, TROP-2, TSG, TSLP, tumor-associated antigen CA125, tumor-associated antigen exhibiting Lewis Y-related carbohydrate, TWEAK, TXB2, Ung, uPAR, uPAR-1, urokinase, VCAM, VCAM-1, VECAD, VE-cadherin, VE-cadherin-2, VEFGR-1 (fit-1), VEGF, VEGFR, VEGFR-3 (flt-4), VEGI, VIM, viral antigen, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, As, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high-molecular-weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, SIP, and receptors for hormones and growth factors.

When an antibody, like a bispecific antibody, binds to a plurality of epitopes in an antigen molecule, an antigen that can form a complex together with the antibody may be any of the above examples of antigens or a combination thereof, in other words, a monomer or heteromultimer. Non-limiting examples of the heteromultimer include heterodimers such as IL-12 comprising IL-12p40 and IL-12p35; IL-23 comprising IL-12p40 and IL-23p19 (also referred to as IL-30B); IL-23 comprising EBI-3 and IL27p28; and IL-35 comprising IL-12p35 and EBI-3.

The above examples of antigens include also receptors. When the receptors are present in a biological fluid such as plasma in a soluble form, they can form a complex together with an antibody. Thus, the receptors listed above can be used as an antigen that can bind to an antibody to form an immune complex as long as the receptors are present in a biological fluid such as plasma in a soluble form. A non-limiting aspect of such a soluble receptor includes, for example, soluble IL-6R as described by Mullberg et al., (J. Immunol. (1994) 152 (10), 4958-4968) (e.g., the protein consisting of the amino acids from position 1 to 357 in the IL-6R polypeptide sequence set forth in SEQ ID NO: 1 described in WO 2013/081143).

The above examples of antigens include also soluble antigens. Fluids in which the antigens are present are not limited. The soluble antigens can be present in biological fluids, i.e., all fluids filling a vessel or a space between tissues or cells within a living body. In a non-limiting aspect, an antigen bound by an antibody can be present in an extracellular fluid. The extracellular fluid is a collective term invertebrates which refers to a plasma, an intercellular fluid, a lymphatic fluid, a tight connective tissue, a cerebrospinal fluid, a spinal fluid, a puncture fluid, components in bones and cartilages such as synovial fluids, an alveolar fluid (a bronchoalveolar lavage fluid), a peritoneal fluid, a pleural effusion, a pericardial fluid, a cyst fluid, or a transcellular fluid (fluids in various glandular lumens resulting from cellular active transport or secretory activity, and fluids in gastrointestinal tract lumens or other body cavities) such as aqueous humor (hydatoid).

When the molecule incorporated into cells via a cell surface receptor is an immune complex or an antibody, the antibody is preferably IgG, and the receptor may be an Fc receptor. The Fc receptor is preferably an FcγR or FcRn. FcγR is more preferably an FcγRII, and even more preferably FcγRIIB.

In the present invention, the "nucleic acid" refers to DNA, RNA, or analogs thereof, and may be a natural or synthesized nucleic acid. The analogs include an artificial nucleic acid such as PNA and LNA. The nucleic acid may be single or double stranded. The nucleic acid may be also modified. The modified nucleic acids include a nucleic acid chemically modified in an internucleoside linkage, base, and/or sugar, and a nucleic acid having a modified group at 5' and/or 3' end(s). Modifications in an internucleoside linkage include alteration of any of phosphodiester linkage, phosphorothioate linkage, phosphorodithioate linkage, methylphosphonate linkage, phosphoramidate linkage, non-phosphate bond, and methyl phosphonothioate linkage, or a combination thereof. Modifications in a base include alteration to 5-propynyluracil, 2-aminoadenine, or the like. Modifications in a sugar include alteration to 2'-fluororibose, 2'-O-methylribose, or the like.

The nucleic acid may be referred to as siRNA, antisense RNA, miRNA, shRNA, ribozyme, or aptamer depending on its function or application. Nucleic acids used in the present invention also include a CpG oligonucleotide which acts on Toll-like receptor 9 (TLR9) to activate natural immunity.

The nucleic acid may have any length sufficient to be incorporated into cells via Stabilin, for example, 4 to 100 bases in length, 10 to 50 bases in length, 10 to 40 bases in length, or 10 to 30 bases in length.

When the molecule incorporated into cells via a cell surface receptor is a nucleic acid, the receptor is preferably Stabilin.

In the present invention, Stabilin refers to a protein belonging to a family of transmembrane proteins known as a nucleic acid receptor. In mammals, Stabilin is known to have two homologs: Stabilin-1 and Stabilin-2. Stabilin in the present invention may be either of the two. In humans, Stabilin-1 (NCBI accession number: NP #055951.2) and Stabilin-2 (NCBI accession number: NP #060034.9) are known and are reportedly expressed in LSECs, spleen, adrenal-cortex, lymph node, and sinusoidal macrophages (Patent Literature 24).

When the molecule incorporated into cells via a cell surface receptor is an antibody that binds to a soluble antigen, the antibody is preferably IgG, and the receptor may be an Fc receptor. The Fc receptor is preferably an FcγR or FcRn. FcγR is more preferably an FcγRII, and even more preferably FcγRIIB.

When the molecule incorporated into cells via a cell surface receptor is an antibody that binds to a membrane-type receptor, examples of the receptor include IL-6R, IL-4R, IL-5R, IL-17R, EGFR, HER2, RANKL, PD-1, and PD-L1, and preferably IL-6R. RANKL and PD-L1 are also called membrane-type ligand. It is known that antibodies directed against RANKL and PD-L1 have also kinetics in the body similar to those of an antibody that binds to a membrane-type receptor. Thus, molecules classified into membrane-type ligands are also included in the "membrane-type receptor" in the present specification. In a preferred aspect, the molecule incorporated into cells via a cell surface receptor is an anti-IL-6R antibody, and the receptor is IL-6R. The anti-IL-6R antibody is more preferably a humanized anti-IL-6R antibody, and even more preferably tocilizumab.

The peptide compound is a compound formed by amino acids or amino acid analogs via amide bond or ester bond. The peptide compound has molecular shapes including a linear shape, a cyclic shape, and a cyclic shape having a linear part.

The number of amide bonds or ester bonds (the number/length of amino acids or amino acid analogs) is not particularly limited. When the peptide compound has a linear part, the peptide compound has preferably in total 30 or less residues in the cyclic and linear parts. More preferably, the total number of amino acids in the cyclic and linear parts is 13 or less. To acquire high metabolic stability, the total number of amino acids is more preferably 9 or more. In addition to the above description, the number of amino acids and amino acid analogs making up cyclic parts is preferably from 5 to 12. Moreover, in addition to the above description, the number of amino acids and amino acid analogs making up cyclic parts is preferably from 5 to 11, more preferably 7 to 11, and particularly 9 to 11 residues. The number of amino acids and amino acid analogs making up linear parts (the number of units) is preferably from 0 to 8, and more preferably 0 to 3. In the present application, unless expressly limited, it shall be understood that amino acids may comprise an amino acid analog.

In the present specification, the "amino acid" and "amino acid analog" making up a peptide compound may be referred to as "amino acid residue" and "amino acid analog residue", respectively.

The amino acid refers to an α, β, or γ amino acid. The amino acid is not limited to natural amino acids (wherein the natural amino acids in the present application refer to 20 amino acids comprised in proteins, specifically Gly, Ala, Ser, Thr, Val, Leu, Ile, Phe, Tyr, Trp, His, Glu, Asp, Gln, Asn, Cys, Met, Lys, Arg, and Pro) and may be a non-natural amino acid. The α-amino acid may be an L- or D-amino acid, or α,α-dialkylamino acid. Amino acid side chains are selected without particular limitation, and are optionally selected from, for example, an alkyl group, an alkenyl group, an alkynyl group, an aryl group, a heteroaryl group, an aralkyl group, and a cycloalkyl group, in addition to hydrogen atoms. Each of the amino acid side chains may have any substituent. The substituents are optionally selected from any functional group containing, for example, N, O, S, B, Si, or P atom (i.e., an alkyl, alkenyl, alkynyl, aryl, heteroaryl, aralkyl, or cycloalkyl group that may be substituted).

Each of the "amino acids" and "amino acid analogs" making up a peptide compound may comprise all isotopes of the atoms that make up the amino acids or amino acid analogs. Isotope-containing "amino acids" or "amino acid analogs" refer to those in which at least one atom making up the amino acids or amino acid analogs is substituted with an atom that has the same atomic number (proton number) but different mass number (the sum of the numbers of protons and neutrons). Examples of the isotopes comprised in the "amino acids" and "amino acid analogs" that make up the peptide compound of the present invention include a hydrogen atom, a carbon atom, a nitrogen atom, an oxygen atom, a phosphorus atom, a sulfur atom, a fluorine atom, and a chlorine atom, which include $^2$H and $^3$H; $^{13}$C and $^{14}$C; $^{15}$N; $^{17}$O and $^{18}$O; $^{31}$P and $^{32}$P; $^{35}$S; $^{18}$F; and $^{36}$Cl, respectively.

When detected with a fluorescent label kit Alexa FluorR 488 Protein Labeling Kit (Invitrogen), the peptide compounds have desirably an amino acid having an amino group. Such an amino acid includes lysine (Lys). An amino acid having a thiol group can be also labeled with a thiol-reactive fluorescent dye. Such an amino acid includes cysteine (Cys).

When the molecule incorporated into cells via a cell surface receptor is a peptide compound, the receptor is preferably PEPT1 or PEPT2.

Nanoparticles and microparticles are known to be used for formulations designed for drug delivery (Drug Delivery System, popularly called DDS). Examples of the nanoparticles and microparticles include, but are not limited to, liposomes, micelles, dendrimers, nanoemulsions, iron nanoparticles, gold nanoparticles, and PLGA particles (Organ Biology VOL. 24 NO. 12017, 54-60).

In a preferred embodiment, the molecules incorporated into cells via a cell surface receptor in the Measurement Method I of the present invention include a nanoparticle or microparticle bound to a molecule that specifically binds to a particular cell population. These nanoparticles and microparticles can be bound to, for example, an antigen-binding molecule directed against a surface antigen of the cell population. These nanoparticles and microparticles can be also bound to, for example, an antigen-binding molecule that binds to an Fc receptor. In an embodiment, the molecule incorporated into cells via a cell surface receptor in the Measurement Method I of the present invention may be a nanoparticle or microparticle bound to an antibody that binds to the receptor, and the receptor may be an Fc receptor or the membrane-type receptor.

It is known that LSECs express hyaluronic acid receptors (CD44, LYVE) and that hyaluronic acid administered to rats accumulates in LSECs (Cell Tissue Res. 1985; 242(3): 505-10; J Hepatol. 2017 January; 66(1): 212-227; J Biomater Sci Polym Ed. 2009; 20(1): 83-97). It is demonstrated in mouse experiments that a transgene can be delivered to LSECs using a liposome bound to hyaluronic acid (J Pharm Sci. 2013 September; 102(9): 3119-27). Thus, in an embodiment, the molecule incorporated into cells via a cell surface receptor in the Measurement Method I of the present invention may be a nanoparticle or microparticle bound to hyaluronic acid, and the receptor may be a hyaluronic acid receptor.

It is known that LSECs also express a mannose receptor and that lysosomal enzymes are recruited to LSECs (Hepatology. 2008 December; 48(6): 2007-15). Thus, in an embodiment, the molecule incorporated into cells via a cell surface receptor in the Measurement Method I of the present invention may be a nanoparticle or microparticle bound to a molecule that binds to a mannose receptor (e.g., glycoproteins, such as lysosomal enzymes), and the receptor may be a mannose receptor.

In the present invention, the "toxin" is not particularly limited as long as it can specifically deliver a cytotoxic agent, poison, or radioactive isotope to a particular cell population to damage the cell population. For example, a molecule that has a cytotoxic agent, poison, or radioactive isotope bound to a molecule that specifically binds to the cell population (e.g., an antigen-binding molecule directed against the cell surface antigen of the cell population) can be produced. Examples of the "molecule that specifically binds to a cell population" include the antibody, nucleic acid, and peptide compound described above. Such a molecule can be used to efficiently deliver a cytotoxic agent, poison, or radioactive isotope to the cell population. Consequently, the cell population can be specifically damaged.

Examples of the cytotoxic agent include maytansinoid (see, U.S. Pat. Nos. 5,208,020 and 5,416,064; and European Patent No. 0,425,235 B1); auristatins such as for example monomethyl auristatin drug moieties DE and DF (MMAE and MMAF) (see, U.S. Pat. Nos. 5,635,483; 5,780,588; and 7,498,298); dolastatins; calicheamicin or its derivative (see, U.S. Pat. Nos. 5,712,374; 5,714,586; 5,739,116; 5,767,285; 5,770,701; 5,770,710; 5,773,001; and 5,877,296; Hinman et al., Cancer Res. 53: 3336-3342 (1993); and Lode et al., Cancer Res. 58:2925-2928 (1998)); anthracyclines such as daunomycin and doxorubicin (see, Kratz et al., Current Med. Chem. 13:477-523 (2006); Jeffrey et al., Bioorganic & Med. Chem. Letters 16:358-362 (2006); Torgov et al., Bioconj. Chem. 16: 717-721 (2005); Nagy et al., Proc. Natl. Acad. Sci. USA 97: 829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; taxanes such as docetaxel, paclitaxel, larotaxel, tesetaxel, and ortataxel; trichothecenes; and CC1065.

Examples of the poison include, but are not limited to, the following enzymatically active poisons or fragments thereof: diphtheria A-chain, a non-binding active fragment of diphtheria poison, exotoxin A-chain (from *Pseudomonas aeruginosa*), ricin A-chain, abrin A-chain, modeccin A-chain, alpha-sarcin, tung tree (*Aleurites fordii*) protein, dianthin protein, pokeweed (*Phytolacca americana*) protein (PAPI, PAPII, and PAP-S), bitter melon (*Momordica charantia*) inhibitor, curcin, crocin, common soapwort (*Saponaria officinalis*) inhibitor, gelonin, mitogellin, restrictocin, fenomycin, enomycin, and trichothecene.

Examples of the radioactive isotope include $^{211}$At, $^{131}$I, $^{125}$I, $^{90}$Y, $^{186}$Re, $^{188}$Re, $^{153}$Sm, $^{212}$Bi, $^{32}$, $^{212}$Pb, and a radioisotope of Lu.

Viruses can be also used to damage a particular cell population. The Measurement Method I of the present invention can be used to measure the cellular uptake of, for example, the following viruses, or viral proteins or moieties thereof.

In the gene therapy, a transgene is introduced into host cells, resulting in therapeutic efficacy. Examples of the virus known to be used in the gene therapy include retroviruses, adenoviruses, adeno-associated viruses, herpes simplex viruses, lentiviruses, poxviruses, and Epstein-Barr virus (Adv Biomed Res. (2012) 1: 27. doi:10.4103/2277-9175.98152). A gene having a cytotoxic activity is incorporated into these viruses to generate a recombinant virus. The recombinant virus can be delivered to the cell population to damage the cell population.

It is reported that a drug directly encapsidated in a virus is utilized for drug delivery (Methods Mol Biol. 2011; 726:207-221). In this report, a nucleic acid (RNA and DNA) was encapsidated in red clover necrotic mosaic virus (RC-NMV) to generate a virus for drug delivery.

A part of a protein that makes up a virus can be also used for drug delivery. Examples include a part of a protein bound to other molecule, wherein the protein is used in virus entry into cells (Nanotheranostics. 2017; 1(4): 415-429).

For example, a partial peptide of HIV-1 tat protein is used as a cell membrane-permeable peptide. L2 peptide of human papillomavirus has an activity to destabilize cell membrane under an acidic condition. HBV envelope L protein interacts with an HBV receptor with a high affinity. A synthetic nanocarrier bound to a partial peptide of the L protein is specifically delivered to human liver cells.

It is also demonstrated using experimental animals that adenoviruses and hepatitis B viruses undergo clearance in LSECs (PLoS Pathog 2011; 7(9): e1002281, Hepatology. 2001; 34(4 Pt 1): 803-8).

The Measurement Method I of the present invention comprises the following steps (i) to (iii):
(i) adding a molecule incorporated into cells via a cell surface receptor to an organ-derived cell population to perform incubation,
(ii) sorting the organ-derived cell population based on the expression levels of CD31 and CD45, and
(iii) after steps (i) and (ii), measuring the amount of the molecule incorporated into the cell population.

As mentioned later, either step (i) or (ii) may be performed first, and step (iii) is performed after steps (i) and (ii).

The Measurement Method I of the present invention is directed to mammals. In one aspect, the mammals are primates, including for example human, monkey (such as cynomolgus monkey, marmoset, and rhesus macaque), and chimpanzee, preferably human or monkey.

The "organ" in step (i) includes organs within a living body harboring cell populations, and also includes blood and bone marrow. In one aspect, the organ is liver, mesenteric lymph node, blood, bone marrow, stomach, lung, or spleen, preferably liver.

The organ-derived cell population can be prepared using a method generally used in the art. The organ-derived cell population may be also a commercial product. For example, human hepatic nonparenchymal cells and monkey hepatic nonparenchymal cells can be obtained from Sekisui Xenotech, LLC and Ina Research Inc., respectively. The cell population may be suspended in a suitable medium (e.g., OptiThaw Kupffer Cell Thaw/Culture Media (Sekisui XenoTech) and HCM (LONZA)), buffer, or the like.

In one aspect, a cell population subject to the Measurement Method I of the present invention is a partially purified cell population. The partially purified cell population refers to a cell population that consists of cells dissociated from a tissue taken from an organ and has not been purified to obtain a cell population having the characteristic of interest. Elimination of excessive purification can keep cells fresh and can prevent alteration in cellular nature. For example, for solid organs, a tissue taken from the organs can be enzymatically processed to dissociate cells followed by removal of impurities with a gauze or similar materials and optional removal of unwanted cell populations using a technique such as centrifugation to obtain a partially purified cell population. An example of the partially purified cell population includes a nonparenchymal cell population prepared from the liver. The hepatic nonparenchymal cell population can be prepared by removing a tissue from the liver, enzymatically processing the tissue with collagenase to dissociate cells, filtering off impurities with a gauze, centrifuging the resulting cell population to remove the precipitated cell population as a hepatic parenchymal cell, and collecting cells contained in the supernatant (Organ Biology Vol. 16 No. 3 2009, 361-370).

In step (i), when the molecule incorporated into cells via a cell surface receptor is an immune complex, the immune complex prepared by previously mixing an antibody with an antigen may be added to the cell population, or the immune complex may be formed during incubation after adding an antibody and an antigen to the cell population.

The organ-derived cell population to which a molecule incorporated into cells via a cell surface receptor is added is incubated at a physiological temperature of the cell population for 10 seconds to 24 hours, for example 1 to 60 minutes. Those skilled in the art can appropriately define the incubation time within the range in which the uptake amount linearly increases, depending on the molecule or biological species and depending on increase therein. The physiological temperature may vary depending on the biological species to be used. For example, in humans, the physiological temperature ranges from 35 to 38° C., for example 36 to 37° C. In monkeys, the physiological temperature ranges from 35 to 38° C., for example 36 to 37° C. In a preferred aspect, the incubation is performed at 37° C. for 60 minutes in humans and is performed at 37° C. for 15 minutes in monkeys.

In step (ii), the organ-derived cell population is sorted based on the expression levels of CD31 and CD45.

In step (ii), the phrase "the organ-derived cell population is sorted based on the expression levels of CD31 and CD45" means that an organ-derived cell population expressing CD31 and CD45 is divided into smaller cell populations to select a cell population having the predetermined ranges of the expression levels of CD31 and CD45. The sorted cell population may be isolated or not from the original cell population.

When a cell population is isolated, examples of the techniques to be used include, but are not particularly limited to, a technique for fractionating cells in a flow cytometer. The techniques that can be used also include "panning" that is known to be a technique to separate cells by placing cell populations on a plate coated with an antibody that binds to a cell surface marker, and "immunomagnetic technique" using "immunomagnetic beads" on which an antibody directed against a cell surface marker is immobilized on beads (Non Patent Literature 15).

To measure the cellular uptake of molecules incorporated into cells via a cell surface receptor, the cell population expressing the receptor is used. If such cell population is sorted using the expression level of the receptor as an index, the uptake of the molecule is unlikely to be accurately measured. For example, when cells are stained with a labeled antibody that binds to the receptor followed by addition of the molecule to the stained cells, the uptake of the molecule may be affected because of competition between the antibody and the molecule. In contrast to this, in the present invention, the cell population that expresses the receptor can be identified by sorting an organ-derived cell population based on the expression levels of CD31 and CD45, and thus the present invention can measure the uptake of the molecule without affecting the uptake of the molecule.

In one aspect, the Measurement Method I of the present invention comprises step (ii) subsequent to step (i), and the organ-derived cell population incubated with the added molecule incorporated into cells via a cell surface receptor is sorted based on the expression levels of CD31 and CD45.

In another aspect, the Measurement Method I of the present invention comprises step (ii) prior to step (i), and the molecule incorporated into cells via a cell surface receptor is added to the organ-derived cell population sorted based on the expression levels of CD31 and CD45 to perform incubation. In this case, the cell population sorted in step (ii) is typically isolated from the original cell population.

In the present specification, the "CD31" refers to a molecule identified as the 31st molecule in CD (cluster of differentiation, cluster of designation, or classification determinant) classification according to a technique of classifying white blood cells based on their surface antigen (Histopathology. 1988 May; 12(5): 461-80.). CD31, also referred to as Platelet Endothelial Cell Adhesion Molecule-1 (PECAM-1), is a single-chain membrane glycoprotein with a molecular weight of 140 kDa and belongs to the immunoglobulin superfamily (Woodfin A., et al. PECAM-1: a multi-functional molecule in inflammation and vascular biology. Arterioscler Thromb Vasc Biol, 2007. 27 (12): 2514-23). Examples of the amino acid sequence of human CD31 include a sequence set forth in NCBI Reference Sequence: NP #000433.4. Examples of the amino acid sequence of monkey CD31 include a sequence set forth in GenBank: AFH32784.1. CD31 is expressed in hematopoietic progenitor cells in the bone marrow system, platelets, and endothelial cell junctions. CD31, which is known as an endothelial cell marker, is reported to be expressed in cytoplasm rather than on a cell surface of normal LSECs (Deleve, L. D., J Clin Invest. 2013 123(5):1861-6).

In the present specification, the "CD45" refers to a molecule identified as the 45th molecule in the CD classification (Penninger J M., et al. CD45: new jobs for an old acquaintance. Nat Immunol, 2001. 2 (5):389-96). CD45 molecule is a single-chain transmembrane protein with a molecular weight ranging from 180 to 235 kDa and has at least 5 isoforms. These isoforms are formed from a combination using alternative splicing of 3 exons (A, B, and C) on the gene sequence. The amino acid sequence that is common among all CD45 isoform structures and is present in the extracellular juxtamembrane region represents a leucocyte common antigen (LCA) which is a non-limiting CD45 antigen. All monoclonal antibodies belonging to the CD45 cluster can react to this common region and can recognize all CD45 isoforms. CD45, which is known as a hematopoietic cell marker, is reported to be also expressed in LSECs. It is reported that CD45 is expressed in periportal LSECs at a high level, is expressed in midlobular LSECs at a level lower than in periportal LSECs, and is not expressed in centrilobular LSECs (Deleve, L. D., J Clin Invest. 2013 123(5): 1861-6.). Examples of the amino acid sequence of human CD45 include a sequence set forth in NCBI Reference Sequence: NP #002829.3. Examples of the amino acid sequence of monkey CD45 include sequences set forth in NCBI Reference Sequence: XP #021532837.1, XP #021532838.1, and XP #021532839.1.

Methods for detecting a cell surface marker expressed in a cell population are broadly divided into (i) a method for detecting a messenger ribonucleic acid (mRNA) of a gene encoding a cell surface marker protein and (ii) a method for detecting a cell surface marker protein.

Examples of the method for detecting mRNA include northern hybridization, Reverse Transcriptase Polymerase Chain Reaction (RT-PCR), and DNA chip analysis. Details of these methods are described in publications (Molecular Cloning: A Laboratory Manual, Cold Spring Harbor Laboratory, 1989, or Current Protocols in Molecular Biology, John Wiley & Sons Inc., 2003).

Examples of the method for detecting proteins include Western blotting, immunohistochemical staining, flow cytometry, Enzyme-Linked ImmunoSorbent Assay (ELISA), surface plasmon resonance analysis, and protein array.

In step (ii), the expression levels of CD31 and CD45 may be measured using any of the methods described above. In a preferred aspect, the cell populations that express cell surface markers CD31 and CD45 is analyzed by flow cytometry, but may be measured using other techniques. Examples of the technique of separating or analyzing a cell population that expresses a particular cell surface marker include "panning" that is known to be a technique to separate cells by placing the cell population on a plate coated with an antibody that binds to the cell surface marker, and cell separation (immunomagnetic technique) using "immunomagnetic beads" on which an antibody directed against the cell surface marker is immobilized on beads. These techniques can be also used to separate and analyze a cell population expressing a particular cell surface marker (Non Patent Literature 15).

When an antibody is used for the measurement of the expression levels of CD31 and CD45, the labeled antibody can be used. The method for labeling an antibody is not limited to a particular method as long as two antibodies to be used for sorting a cell population can be differentiated. Any method generally used in the art may be utilized. Examples of the method for labeling an antibody include fluorescence labeling, biotin labeling of antibodies, peptide tag (such as His tag, FLAG tag, and HA tag) labeling, colloidal gold labeling, magnetic bead labeling, Radio Isotope (RI; radioactive isotope) labeling, and enzymatic labeling (such as with Horse Radish Peroxydase (HRP) or Alkaline Phosphatase (AP)). Examples of the fluorescence labels typically used include Rhodamin, VioBlue, DyLight 405, DY-405, Alexa Fluor 405, AMCA, AMCA-X, Pacific Blue, DY-415, Royal Blue, ATTO 425, Cy2, ATTO 465, DY-475XL, NorthemLights 493, DY-490, DyLight 488, Alexa Fluor 488, 5-FITC, 5-FAM, DY-495-X5, DY-495, Fluorescein, FITC, ATTO 488, HiLyte Flour 488, MFP488, ATTO 495, Oyster 500. Any combination of the labels may be used as long as the labels have different fluorescence excitation spectra.

The description that cells are "positive" or "negative" for a particular marker is generally used in the art, but an expression level is actually quantitative. Even if there are several orders of magnitude difference in the numbers of molecules on the surface of cells, the cells are still characterized as "positive". It is well known in the art that negative cells, more specifically cells having undetectable difference in the expression level from the control may also express markers at a low level. Analysis of the expression level permits detailed sorting among cell populations.

In a preferred aspect, the expression levels of CD31 and CD45 are measured with fluorescently labeled antibodies.

When fluorescence reagents are used, the staining intensity (i.e., the expression levels of CD31 and CD45) of cells can be monitored by flow cytometry in which a level of the fluorescent dye (proportional to the amount of a cell surface marker bound to a particular reagent, such as an antibody) is quantitatively detected by a laser. Flow cytometry, or FACS can be used for separation of cell populations based on other parameters such as binding strength to a particular reagent, cell size, and light scattering. The absolute level of staining may vary depending on particular fluorescent dyes and reagent preparation, but data can be normalized to the control.

To normalize a distribution to the control, individual cells are recorded as a data point having a particular staining intensity. These data points can be displayed on a logarithmic scale using any staining intensity as a measurement unit. By way of example, the most intensely stained cell in a sample has a staining intensity that is three orders of magnitude higher than the staining intensity in negative cells. Such display expressly shows that cells having the staining intensity of the highest order of magnitude are intensely stained and cells having the lowest staining intensity are negative. Positive cells that have a "low" staining intensity have a staining level that is higher than the staining level in the identical isotype control, but have a staining level that is not as high as that in the most intensely stained cell commonly observed in the cell population. The positive cells that have a low staining intensity may have a unique property different from negative cells and intensely stained positive cells in a sample.

In the present specification, the "one order of magnitude" difference roughly represents the same degree or a 10-fold difference; the "two orders of magnitude" difference roughly represents 10- to 100-fold difference; "three orders of magnitude" difference roughly represents 100- to 1000-fold difference; and the "four orders of magnitude" difference roughly represents 1000- to 10000-fold difference.

In a preferred aspect of the present invention, the organ-derived cell population is a human hepatic nonparenchymal cell population, and the $CD31^{high}$ $CD45^{low}$ cell population is sorted in step (ii).

In this aspect, the $CD31^{high}$ $CD45^{low}$ cell population means a cell population having a "high" staining intensity (expression level) of CD31 and a "low" expression level of CD45. For CD31, the "high" staining intensity refers to a staining intensity that is two to three orders of magnitude higher than the staining intensity in negative cells when the staining intensity in the most intensely stained cells is three orders of magnitude higher than the staining intensity in negative cells. The "low" staining intensity refers to a staining intensity that is one or more orders of magnitude higher than the staining intensity in negative cells and is less than two orders of magnitude higher than the staining intensity in negative cells.

For CD45, the "high" staining intensity refers to a staining intensity that is two to three orders of magnitude higher than the staining intensity in negative cells when the staining intensity in the most intensely stained cells is three orders of magnitude higher than the staining intensity in negative cells. The "low" staining intensity refers to a staining intensity that is one or more orders of magnitude higher than the staining intensity in negative cells and is less than two orders of magnitude higher than the staining intensity in negative cells.

Figure 8:
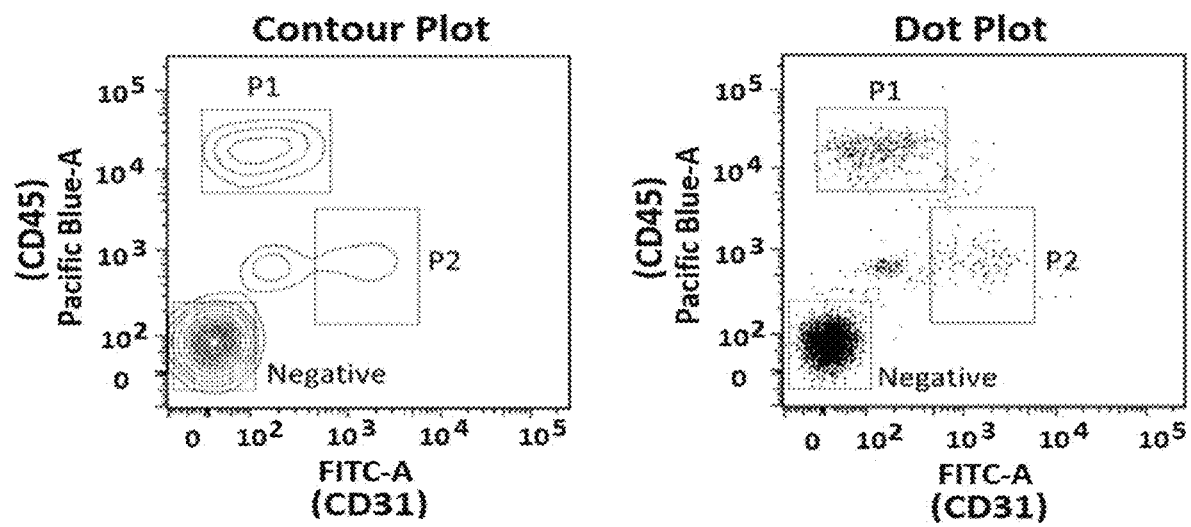

The negative cells are in the cell population having the lowest fluorescence intensity, for example, the cell population in the left lower area in FIG. 8.

For human hepatic nonparenchymal cell populations, when the expression of CD31 and CD45 is detected by flow cytometry, and the expression levels of CD31 and CD45 are plotted on the X-axis and Y-axis, respectively, two distinguishable cell populations (areas) from each other with a high cell density appear in addition to signals that may result from cells that do no express these molecules, autofluorescence, and non-specific fluorescence from debris. These two areas can be shown as an area that is enclosed by a contour line unconnected to contour lines in other areas in a contour plot based on the cell density. The $CD31^{high}$ $CD45^{low}$ cell population is one of the cell populations contained in the two areas and has a high expression level of CD31 and a low expression level of CD45 compared with the other cell population when these expression levels are compared at the highest cell density in each cell population.

The $CD31^{high}$ $CD45^{10}$ cell population is a cell population that has a fluorescence intensity of CD31 ranging from 400 to 7000 and a fluorescence intensity of CD45 ranging from 100 to 4000 in the detection of CD31 and CD45 expressions by flow cytometry when the mean fluorescence intensities of CD31 and CD45 in negative cells are about 7 and about 70, respectively, and the staining intensities of CD31 and CD45 in the most intensely stained cells are about 7000 and about 70000, respectively.

In a preferred aspect of the present invention, the organ-derived cell population is a human hepatic nonparenchymal cell population, and the cell population indicated by P2 in FIG. 8 is sorted in step (ii).

In a preferred aspect of the present invention, the organ-derived cell population is a monkey hepatic nonparenchymal cell population, and the $CD31^{intermediate}$ $CD45^{intermediate}$ cell population is sorted in step (ii).

In this aspect, the $CD31^{intermediate}$ $CD45^{intermediate}$ cell population means a cell population having an "intermediate" staining intensity (expression level) of CD31 and an "intermediate" expression level of CD45. For CD31, the "intermediate" staining intensity refers to a staining intensity that is the same degree as or one order of magnitude higher than the staining intensity in negative cells when the staining intensity in the most intensely stained cells is three orders of magnitude higher than the staining intensity in negative cells. For CD45, the "intermediate" staining intensity refers to a staining intensity that is one to two orders of magnitude higher than the staining intensity in negative cells when the staining intensity in the most intensely stained cells is two orders of magnitude higher than the staining intensity in negative cells.

Figure 2:
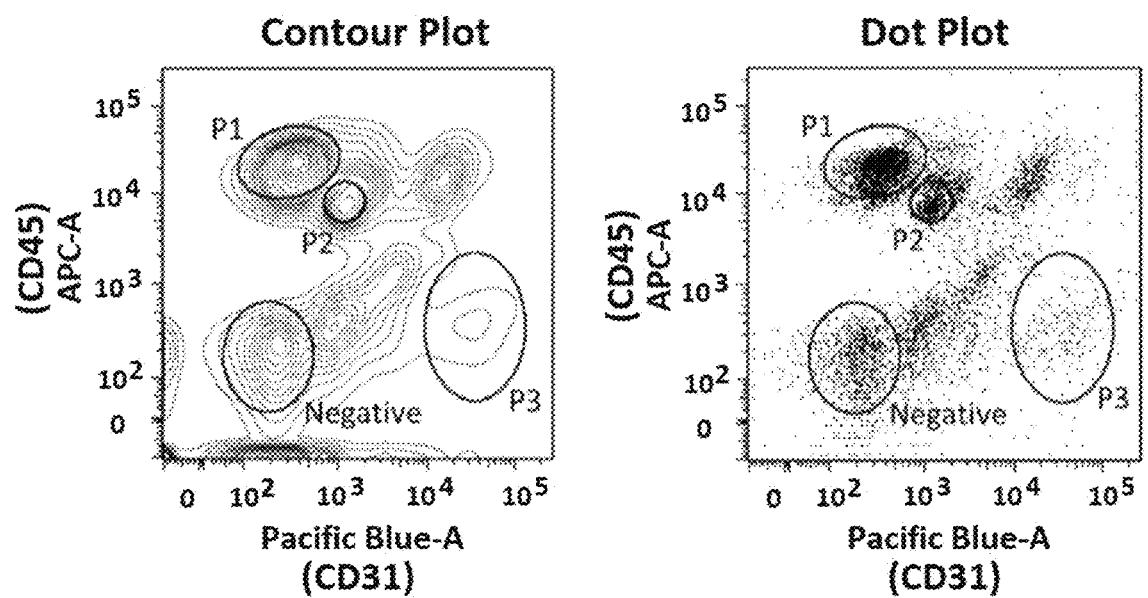
FIG. 2 is a scatter diagram plotting the fluorescence intensity of Pacific Blue against the expression intensity of APC in total cells in the scatter diagram shown in FIG. 1, in which monkey hepatic nonparenchymal cells were stained with Pacific Blue-labeled anti-CD31 antibody and APC-labeled anti-CD45 antibody before measuring respective fluorescence intensities in FACS. Signals detected are categorized into three cell populations: $CD31^{Low}$ $CD45^{High}$, $CD31^{Intermediate}$ $CD45^{Intermediate}$, and $CD31^{High}$ $CD45^{Low}$ cell populations (which represent P1, P2, and P3, respectively). Signals that may result from cells that do not express these cell markers, noise, or autofluorescence are detected in areas other than the three cell populations and are also detected in non-stained cells.

The negative cells are in the cell population having the lowest fluorescence intensity, for example, the cell population in the left lower area in FIG. 2.

For monkey hepatic nonparenchymal cell populations, when the expression of CD31 and CD45 is detected by flow cytometry, and the expression levels of CD31 and CD45 are plotted on the X-axis and Y-axis, respectively, three distinguishable cell populations (areas) from each other with a high cell density are observed in addition to signals that result from cells that do not express these molecules, autofluorescence, and non-specific fluorescence from debris. These three areas can be shown as an area that is enclosed by a contour line unconnected to contour lines of other areas in a contour plot based on the cell density. The $CD31^{intermediate}$ $CD45^{intermediate}$ cell population is one of the three cell populations and has the second highest expression levels of CD31 and CD45 when these expression levels are compared at the highest cell density in each cell population.

The $CD31^{intermediate}$ $CD45^{intermediate}$ cell population is a cell population that has a fluorescence intensity of CD31 ranging from 500 to 3000 and a fluorescence intensity of CD45 ranging from 4000 to 20000 in the detection of CD31 and CD45 expressions by flow cytometry when the mean fluorescence intensities of CD31 and CD45 in negative cells are each about 200 and the staining intensities of CD31 and CD45 in the most intensely stained cells are about 150000 and about 70000, respectively.

Alteration of the mean fluorescent intensity in negative cells that is used as a criterion will also result in variation of the fluorescence intensity range in the $CD31^{intermediate}$ $CD45^{intermediate}$ cell population. For example, the $CD31^{intermediate}$ $CD45^{intermediate}$ cell population may be a cell population that has a fluorescence intensity of CD31 ranging from 200 to 900 and a fluorescence intensity of CD45 ranging from 1500 to 8000 when the mean fluorescence intensities of CD31 and CD45 in negative cells are about 100 and about 20, respectively and the staining intensities of CD31 and CD45 in the most intensely stained cells are about 150000 and about 70000, respectively.

In a preferred aspect of the present invention, the organ-derived cell population is a monkey hepatic nonparenchymal cell population, and the cell population indicated by P2 in FIG. 2 is sorted in step (ii).

In step (iii), the uptake amount of a molecule incorporated into cells via a cell surface receptor is measured in the cell population that have undergone steps (i) and (ii).

The uptake amount of a molecule incorporated into cells via a cell surface receptor can be quantified by labeling the molecule and detecting the signal intensity of the label. Labels for proteins include those used for labeling of the antibody. Any labeling method typical in the art may be used.

Labeling methods for individual molecules are appropriately selected by those skilled in the art. Methods for labeling general compounds include labeling with stable isotopes. This labeling method is generally known as a labeling method used for body kinetic analysis of candidate compounds for pharmaceutical agents (Pharmacokinetics, vol. 8, No. 3, 1993, 99-109 [in Japanese]).

Labeling may be performed using a commercially available kit. Fluorescence labeling of proteins can be performed using a commercially available kit such as Alexa Fluor(R) 488 Protein Labeling Kit.

Labels for a molecule incorporated into cells via a cell surface receptor can be a label distinguishable from labels for CD31 and CD45.

In a preferred aspect, a molecule incorporated into cells via a cell surface receptor is labeled with a fluorescent label to measure the uptake amount of the molecule in a flow cytometer.

I-2. Composition for Uptake Assays of a Molecule Incorporated into Cells Via a Cell Surface Receptor The second aspect of the present invention relates to a composition for uptake assays of a molecule incorporated into cells via a cell surface receptor (hereinafter also referred to as Composition I of the present invention). The uptake assay of a molecule incorporated into cells via a cell surface receptor refers to a test in which a cellular uptake of the molecule is assessed. In a preferred aspect, the assay is performed using the Measurement Method I of the present invention.

The Composition I of the present invention comprises an isolated organ-derived cell population that expresses CD31 and CD45. In the present invention, the term "isolated" refers to a state separated from an organ. In one aspect, the cell population is a partially purified cell population.

The "organ" in the present invention includes organs within a living body harboring cell populations, and also includes blood and bone marrow. In one aspect, the organ is liver, mesenteric lymph node, blood, bone marrow, stomach, lung, or spleen, and preferably liver.

The cell population may be any cell population in which the expression of CD31 and CD45 can be detected using any method generally used in the art (e.g., a method for detecting a cell surface marker described in the section I-1 above).

In a preferred aspect, the organ-derived cell population comprised in the Composition I of the present invention is a human hepatic nonparenchymal $CD31^{high}CD45^{low}$ cell population. In this aspect, the Composition I of the present invention does not comprise $CD31^{low\ CD}45^{high}$ cell population.

In a more preferred aspect, the organ-derived cell population comprised in the Composition I of the present invention is a human hepatic nonparenchymal cell population which consists of the cell population indicated by P2 in FIG. 8. In this aspect, the Composition I of the present invention does not comprise the cell population indicated by P1 in FIG. 8.

In another preferred aspect, the organ-derived cell population is a monkey hepatic nonparenchymal CD31intermediate CD45intermediate cell population. In this aspect, the Composition I of the present invention does not comprise a $CD31^{low}\ CD45^{high}$ cell population and/or $CD31^{high}\ CD45^{low}$ cell population.

In a more preferred aspect, the organ-derived cell population is a monkey hepatic nonparenchymal cell population which consists of the cell population indicated by P2 in FIG. 2. In this aspect, the Composition I of the present invention does not comprise the cell populations indicated by P1 and P3 in FIG. 2.

These cell populations, which express FcγRIIB, are suitable for assessing an uptake of an immune complex or an antibody.

These cell populations, which express IL-6R, are also suitable for assessing an uptake of anti-IL-6R antibody.

The Composition I of the present invention may comprise a medium as well as a cell population. The medium can be appropriately selected according to the organ type and animal species. Examples of the medium for cell populations derived from human liver include OptiThaw Kupffer Cell Thaw/Culture Media (Sekisui XenoTech). Examples of the medium for cell populations derived from monkey liver include HCM (LONZA).

The Composition I of the present invention can be produced using a method comprising (i) preparing organ-derived cells from an organ removed from a living body, and (ii) sorting the cells based on the expression levels of CD31 and CD45.

Steps (i) and (ii) can be performed according to the description in the section I-1 above.

I-3. Method for Predicting In Vivo Elimination Clearance of a Molecule Incorporated into Cells Via a Cell Surface Receptor The third aspect of the present invention relates to a method for predicting in vivo elimination clearance of a molecule incorporated into cells via a cell surface receptor (hereinafter also referred to as Prediction Method I of the present invention).

The Prediction Method I of the present invention comprises the following steps:
(i) measuring a cellular uptake amount of the molecule incorporated into cells via a cell surface receptor using the measurement method of the present invention, and
(ii) predicting the in vivo elimination clearance of the molecule upon administration to a living body, based on the uptake amount measured in the step (i).

When the molecule incorporated into cells via a cell surface receptor is an immune complex, the method may comprise forming an immune complex from an antigen and an antibody before step (i). The forming step can be performed by mixing an antigen with an antibody. In step (i), the antibody and the antigen may be added to the cell population, resulting in formation of an immune complex during incubation.

Step (i) can be performed according to the description in the section I-1 above.

In step (ii), the in vivo elimination clearance is predicted from the uptake amounts measured in step (i) based on the correlation between the "in vitro uptake amount of the molecule" and the "in vivo elimination clearance of the molecule", which are previously calculated. The correlation is calculated for each of the molecules and biological species in a manner similar to an illustrative example in which monkey is used as described later.

The in vitro uptake amount of the test molecule is measured and calculated using the following method.

Monkey hepatic nonparenchymal cells are commercially available from, for example, Ina Research Inc.

A test molecule fluorescently labeled with Alexa488 for detection is added to monkey hepatic nonparenchymal cells to allow reaction at 37° C. for 15 minutes. Subsequently, antibodies that are directed against cell surface markers CD31 and CD45 are labeled with different fluorescent labels, respectively, are added to the reaction. The cell group positive for CD31 and CD45 is identified in flow cytometry, and the uptake amount of the test molecule is measured in the receptor-positive cell group. The fluorescence intensity detected by flow cytometry is converted into mass. A kit for normalizing a fluorescence intensity and mass, such as Quantum™ MESF (Bangs Laboratories), may be used.

In vivo elimination clearance (plasma clearance) of test molecules is calculated using non-compartment model analysis in which a test molecule is administered to a monkey (e.g., cynomolgus monkey), and the antibody concentration in plasma is measured until 56 days after administration.

The values of "in vitro uptake amount of the test molecule" are plotted against the "in vivo elimination clearance of the test molecule" for individual molecules. Thus, the correlation between the in vivo elimination clearance of the test molecule and the in vitro uptake amount of the test molecule can be calculated.

Binding activity assessment using Biacore or the like, which can evaluate affinity of test molecules to receptors thereof, is unable to predict in vivo kinetics of test molecules. In contrast to this, the Prediction Method I of the present invention can estimate in vivo behavior of test molecules from in vitro test results. The Prediction Method I of the present invention can be also applied to humans and can provide an increased accuracy of pharmacokinetics prediction in humans compared with conventional prediction methods based on tests in nonhuman animals.

I-4. Method of Predicting In Vivo Reduction Rate of Antigens in a Blood Upon Administration of an Antibody When the molecule incorporated into cells via a cell surface receptor is an immune complex, the fourth aspect of the present invention relates to a method for predicting in vivo reduction rate of antigens in a blood upon administration of an antibody (hereinafter also referred to as Prediction Method Ia of the present invention).

The Prediction Method Ia of the present invention comprises the following steps:
(i) forming an immune complex from an antigen and an antibody,
(ii) measuring a cellular uptake amount of the immune complex formed in the step (i) using the Measurement Method I of the present invention, and
(iii) predicting in vivo reduction rate of antigens in the blood upon administration of the antibody to a living body, based on the uptake amount measured in the step (ii).

Step (i) can be performed by mixing an antigen with an antibody. In step (ii), the antibody and the antigen may be added to the cell population, resulting in formation of an immune complex during incubation.

Step (ii) can be performed according to the description in the section I-1 above.

In step (iii), the uptake efficiency (clearance) of the immune complex is calculated from the uptake amounts measured in step (ii), and the in vivo reduction rate of antigens in a blood is predicted based on the correlation between the "in vitro uptake efficiency (clearance) of the immune complex" and the "in vivo reduction rate of the antigen in a blood", which are previously calculated. The correlation is calculated for each of the antigen and biological species in a manner similar to an illustrative example in which monkey is used as described later.

The in vitro uptake efficiency (clearance) of the immune complex is measured and calculated using the following method.

Monkey hepatic nonparenchymal cells are commercially available from, for example, Ina Research Inc.

Monkey myostatin fluorescently labeled with Alexa488 for detection and the unmodified anti-monkey myostatin antibody (SG1) or various modified anti-monkey myostatin antibodies are added to monkey hepatic nonparenchymal cells to allow reaction at 37° C. for 15 minutes. Subsequently, antibodies that are directed against cell surface markers CD31 and CD45 are labeled with different fluorescent labels, respectively, are added to the reaction. The cell group positive for CD31 and CD45 is identified in flow cytometry, and the uptake amount of monkey myostatin is measured in the FcγRIIB-positive cell group. The fluorescence intensity detected by flow cytometry is converted into mass. A kit for normalizing a fluorescence intensity and mass, such as Quantumn™ MESF (Bangs Laboratories), may be used. The calculated results are used to calculate in vitro uptake clearance according to the following equation.

In vitro uptake clearance (mL/day/2×10' cells)=[Uptake amount (pg/2×10' cells)]/[Reaction time (min)×Reaction concentration (pg/mL)]×60×24 wherein the reaction concentration is a concentration at the time of the reaction of an antigen, monkey myostatin with monkey hepatic nonparenchymal cells.

The in vivo antigen reduction rate is determined by administering various modified anti-monkey myostatin antibodies to monkey (e.g., cynomolgus monkey) and measuring monkey myostatin concentration 14 days after administration (this method is described in, for example, Example 21 of WO 2016/098357).

When the myostatin concentration in plasma upon administration of the unmodified anti-monkey myostatin antibody SG1 is defined as 1, the in vivo monkey myostatin reduction rate can be calculated from the myostatin concentration in plasma upon administration of each antibody according to the following equation.

In vivo reduction rate of monkey myostatin from plasma=(Myostatin concentration in plasma upon administration of SG1)/(Myostatin concentration in plasma upon administration of each antibody)

wherein the concentration in plasma is a concentration in plasma 14 days after antibody administration.

The value of "in vitro uptake clearance" calculated based on the "in vitro cellular uptake amount of monkey myostatin" is plotted against "in vivo reduction rate of monkey myostatin from plasma" for each antibody (FIG. 6). Thus, the correlation between the in vivo reduction rate of monkey myostatin in each plasma sample relative to SG1 and the in vitro amount of monkey myostatin incorporated into monkey hepatic nonparenchymal cells can be determined.

I-5. Method for Screening for a Molecule Incorporated into Cells Via a Cell Surface Receptor The fifth aspect of the present invention relates to a method for screening for a molecule incorporated into cells via a cell surface receptor (hereinafter also referred to as Screening Method I of the present invention).

The Screening Method I of the present invention comprises the following steps:

(i) providing two or more different molecules that bind to an identical receptor and are incorporated into cells via a cell surface receptor,
(ii) measuring a cellular uptake amount of each of the molecules provided in the step (i) using the Measurement Method I of the present invention, and
(iii) mutually comparing the cellular uptake amounts of the molecules measured in the step (ii) to select the molecule that has the highest uptake amount.

The two or more molecules in step (i) are molecules that have a binding activity to an identical receptor and are different from each other. The molecules incorporated into cells via a cell surface receptor are as described in the section I-1 above.

When the molecule incorporated into cells via a cell surface receptor is an immune complex, step (i) can be performed by mixing an antigen with an antibody. In step (ii), the antibody and the antigen may be added to the cell population, resulting in formation of an immune complex during incubation.

Step (ii) can be performed for each of the two or more molecules according to the description in the section I-1 above.

In step (iii), the molecule that has the highest cellular uptake amount is selected.

The selected molecule can be used for application purposes suited for its characteristic. For example, when the selected molecule is an immune complex, the antibody contained in the immune complex can be used as an antibody having the highest antigen clearance function (see, the section I-6 below).

When the selected molecules are DDS formulations such as a toxin, virus, or nanoparticle or microparticle, the molecules can be used to exert their drug efficacy by directly damaging cells within a living body corresponding to the cell population used for the screening method of the present invention. For example, a compound having a cytotoxic potential in a DDS formulation can be delivered to a cell population within a living body to damage the cell population.

I-6. Method for Screening for an Antibody Having an Antigen Clearance Function

When the molecule incorporated into cells via a cell surface receptor is an immune complex, the sixth aspect of the present invention relates to a method for screening for an antibody having an antigen clearance function (hereinafter also referred to as Screening Method Ia of the present invention).

The Screening Method Ia of the present invention comprises the following steps:
  (i) providing two or more different antibodies that bind to an identical antigen,
  (ii) providing an immune complex containing the antigen and each of the two or more antibodies provided in the step (i),
  (iii) measuring a cellular uptake amount of each of the immune complexes provided in the step (ii) using the Measurement Method I of the present invention, and
  (iv) mutually comparing the cellular uptake amounts of the immune complexes measured in the step (iii) to select the immune complex that has the highest uptake amount.

The two or more antibodies in step (i) are antibodies that have a binding activity to the identical antigen and have amino acid sequences different from each other. The antibody and antigen are as described in the section I-1 above.

Step (ii) can be performed by mixing an antigen with an antibody. In step (iii), the antibody and the antigen may be added to the cell population, resulting in formation of an immune complex during incubation.

Steps (ii) and (iii) can be performed for each of the two or more antibodies according to the description in the section I-1 above.

Selection of the immune complex that has the highest cellular uptake amount in step (iv) can result in selection of the antibody contained in the immune complex as an antibody having the highest antigen clearance function.

II. Cellular Uptake of a Nucleic Acid

II-1. Method for Measuring a Cellular Uptake Amount of a Nucleic Acid

The first aspect of the present invention relates to a method for measuring a cellular uptake amount of a nucleic acid (hereinafter also referred to as Measurement Method II of the present invention).

The "nucleic acid" is as described in the section I above.

The Measurement Method II of the present invention comprises the following steps (i) to (iii):
  (i) adding the nucleic acid to an organ-derived cell population to perform incubation,
  (ii) sorting the organ-derived cell population that expresses Stabilin, and
  (iii) after steps (i) and (ii), measuring the amount of the nucleic acid incorporated into the cell population.

As mentioned later, either step (i) or (ii) may be performed first, and step (iii) is performed after steps (i) and (ii).

The Measurement Method II of the present invention is directed to mammals. In one aspect, the mammals are primates, including for example human, monkey (such as cynomolgus monkey, marmoset, and rhesus macaque), and chimpanzee, preferably human or monkey.

The "organ" in step (i) includes organs within a living body harboring cell populations, and also includes blood and bone marrow. In one aspect, the organ is liver, mesenteric lymph node, blood, bone marrow, stomach, lung, or spleen, preferably liver.

The organ-derived cell population can be prepared using a method generally used in the art. The organ-derived cell population may be also a commercial product. For example, human hepatic nonparenchymal cells and monkey hepatic nonparenchymal cells can be obtained from Sekisui Xenotech, LLC and Ina Research Inc., respectively. The cell population may be suspended in a suitable medium (e.g., OptiThaw Kupffer Cell Thaw/Culture Media (Sekisui Xenotech) and HCM (LONZA)), buffer, or the like.

In one aspect, a cell population subject to the Measurement Method II of the present invention is a partially purified cell population. The partially purified cell population refers to a cell population that consists of cells dissociated from a tissue taken from an organ and has not been purified to obtain a cell population having the characteristic of interest. Elimination of excessive purification can keep cells fresh and can prevent alteration in cellular nature. For example, for solid organs, a tissue taken from the organs can be enzymatically processed to dissociate cells followed by removal of impurities with a gauze or similar materials and optional removal of unwanted cell populations using a technique such as centrifugation to obtain a partially purified cell population. An example of the partially purified cell population includes a nonparenchymal cell population prepared from the liver. The hepatic nonparenchymal cell population can be prepared by removing a tissue from the liver, enzymatically processing the tissue with collagenase to dissociate cells, filtering off impurities with a gauze, centrifuging the resulting cell population to remove the precipitated cell population as a hepatic parenchymal cell, and collecting cells contained in the supernatant (Organ Biology Vol. 16 No. 3 2009, 361-370).

The organ-derived cell population to which a nucleic acid is added in step (i) is incubated at a physiological temperature of the cell population for 10 seconds to 24 hours, for example 1 to 60 minutes. The physiological temperature in humans ranges from 35 to 38° C., for example 36 to 37° C. The physiological temperature in monkeys ranges from 35 to 38° C., for example 36 to 37° C. In a preferred aspect, the incubation is performed at 37° C. for 60 minutes in humans and is performed at 37° C. for 15 minutes in monkeys.

In step (ii), the organ-derived cell population expressing Stabilin is sorted.

Stabilin is as described in the section I above.

The cell population sorted in step (ii) may be isolated or not from the original cell population.

When a cell population is isolated, the techniques to be used are not particularly limited and include, for example, a technique for fractionating cells in a flow cytometer. The techniques also include "panning" that is known to be a technique to separate cells by placing cell populations on a plate coated with an antibody that binds to a cell surface marker, and "immunomagnetic technique" using "immunomagnetic beads" on which an antibody directed against a cell surface marker is immobilized on beads (Non Patent Literature 15).

In one aspect, the Measurement Method II of the present invention comprises step (ii) subsequent to step (i), and the organ-derived cell population incubated with the added nucleic acid is sorted for a cell population expressing Stabilin.

In another aspect, the Measurement Method II of the present invention comprises step (ii) prior to step (i), and a nucleic acid is added to the sorted organ-derived cell population expressing Stabilin to perform incubation. In this case, the cell population sorted in step (ii) is typically isolated from the original cell population.

In step (ii), any method typical in the art can be used to sort the organ-derived cell population expressing Stabilin. The expression of Stabilin can be detected using, for example, a method for detecting mRNA of the gene encoding Stabilin and a method for detecting Stabilin protein.

Examples of the method for detecting mRNA include Northern hybridization, Reverse Transcriptase Polymerase Chain Reaction (RT-PCR), and DNA chip analysis. Details of these methods are described in publications (Molecular Cloning: A Laboratory Manual, Cold Spring Harbor Laboratory, 1989, or Current Protocols in Molecular Biology, John Wiley & Sons Inc., 2003).

Examples of the method for detecting proteins include Western blotting, immunohistochemical staining, flow cytometry, Enzyme-Linked ImmunoSorbent Assay (ELISA), surface plasmon resonance analysis, and protein array.

In step (ii), the expression level of Stabilin may be measured using any of the methods described above. In a preferred aspect, the cell populations expressing Stabilin are analyzed by flow cytometry, but may be analyzed with other techniques. Examples of the technique of separating and analyzing a cell population that expresses a particular protein include "panning" that is known to be a technique to separate cells by placing the cell population on a plate coated with an antibody that binds to the protein, and cell separation (immunomagnetic technique) using "immunomagnetic beads" on which an antibody directed against the protein is immobilized on beads. These techniques can be also used to separate and analyze a cell population expressing a particular protein (Non Patent Literature 15).

In the present invention, when a cell population expressing Stabilin is sorted using the expression level of Stabilin as an index, uptake of a nucleic acid is unlikely to be accurately measured. For example, when cells are stained with a labeled anti-Stabilin antibody and a nucleic acid is added to the stained cells, the uptake of nucleic acid may be affected because of competition between the antibody and the nucleic acid.

Thus, in a preferred aspect of the present invention, the cell population expressing Stabilin is sorted without using the expression level of Stabilin as an index. For example, the organ-derived cell population can be sorted based on the expression levels of CD31 and CD45 to identify the cell population expressing Stabilin. In this aspect, the cell population sorted in step (ii) is a cell population expressing CD31 and CD45.

In the preferred aspect described above, in step (ii), the phrase "the organ-derived cell population is sorted based on the expression levels of CD31 and CD45" means that an organ-derived cell population expressing CD31 and CD45 is divided into smaller cell populations to select a cell population having the predetermined ranges of the expression levels of CD31 and CD45.

Measurement of the expression levels of CD31 and CD45 is as described in the section I-1 above.

When an antibody is used for the measurement of the expression levels of Stabilin, CD31, and CD45, the labeled antibody may be used. The method for labeling an antibody is not limited to a particular method as long as two antibodies to be used for sorting a cell population can be differentiated. Any method generally used in the art may be utilized. Examples of the method for labeling an antibody include fluorescence labeling, biotin labeling of antibodies, peptide tag (such as His tag, FLAG tag, and HA tag) labeling, colloidal gold labeling, magnetic bead labeling, Radio Isotope (RI; radioactive isotope) labeling, and enzymatic labeling (such as with Horse Radish Peroxydase (HRP) or Alkaline Phosphatase (AP)). Examples of the fluorescence labels typically used include Rhodamin, VioBlue, DyLight 405, DY-405, Alexa Fluor 405, AMCA, AMCA-X, Pacific Blue, DY-415, Royal Blue, ATTO 425, Cy2, ATTO 465, DY-475XL, NorthernLights 493, DY-490, DyLight 488, Alexa Fluor 488, 5-FITC, 5-FAM, DY-495-X5, DY-495, Fluorescein, FITC, ATTO 488, HiLyte Flour 488, MFP488, ATTO 495, Oyster 500. Any combination of the labels may be used as long as the labels have different fluorescence excitation spectra.

The description that cells are "positive" or "negative" for a particular marker is generally used in the art, but an expression level is actually quantitative. Even if there are several orders of magnitude difference in the numbers of molecules on the surface of cells, the cells are still characterized as "positive". It is well known in the art that negative cells, more specifically cells having undetectable difference in the expression level from the control may also express markers at a low level. Analysis of the expression level permits detailed sorting among cell populations.

In a preferred aspect, the expression levels of Stabilin, CD31, and CD45 are measured with fluorescently labeled antibodies.

When fluorescence reagents are used, the staining intensity (i.e., the expression levels of Stabilin, CD31, and CD45) of cells can be monitored by flow cytometry in which a level of the fluorescent dye (proportional to the amount of a cell surface marker bound to a particular reagent, such as an antibody) is quantitatively detected by a laser. Flow cytometry, or FACS can be used for separation of cell populations based on other parameters such as binding strength to a particular reagent, cell size, and light scattering. The absolute level of staining may vary depending on particular fluorescent dyes and reagent preparation, but data can be normalized to the control.

To normalize a distribution to the control, individual cells are recorded as a data point having a particular staining intensity. These data points can be displayed on a logarithmic scale using any staining intensity as a measurement unit. By way of example, the most intensely stained cell in a sample has a staining intensity that is three orders of magnitude higher than the staining intensity in negative cells. Such display expressly shows that cells having the staining intensity of the highest order of magnitude are intensely stained and cells having the lowest staining intensity are negative. Positive cells that have a "low" staining intensity have a staining level that is higher than the staining level in the identical isotype control, but have a staining level that is not as high as that in the most intensely stained cell commonly observed in the cell population. The positive cells that have a low staining intensity may have a unique property different from negative cells and intensely stained positive cells in a sample.

In the present specification, the "one order of magnitude" difference roughly represents the same degree or a 10-fold difference; the "two orders of magnitude" difference roughly represents 10- to 100-fold difference; "three orders of magnitude" difference roughly represents 100- to 1000-fold difference; and the "four orders of magnitude" difference roughly represents 1000- to 10000-fold difference.

In a preferred aspect of the present invention, the organ-derived cell population is a human hepatic nonparenchymal cell population, and the CD31$^{high}$ CD45$^{low}$ cell population or CD31$^{low}$ CD45$^{high}$ cell population is sorted in step (ii).

In this aspect, the CD31$^{high}$ CD45$^{low}$ cell population means a cell population having a "high" staining intensity (expression level) of CD31 and a "low" expression level of CD45. The CD31$^{low}$ CD45$^{high}$ cell population means a cell population having a "low" staining intensity (expression level) of CD31 and a "high" expression level of CD45. For CD31, the "high" staining intensity refers to a staining intensity that is two to three orders of magnitude higher than the staining intensity in negative cells when the staining intensity in the most intensely stained cells is three orders of magnitude higher than the staining intensity in negative cells. The "low" staining intensity refers to a staining intensity that is one or more orders of magnitude higher than the staining intensity in negative cells and is less than two orders of magnitude higher than the staining intensity in negative cells.

For CD45, the "high" staining intensity refers to a staining intensity that is two to three orders of magnitude higher than the staining intensity in negative cells when the staining intensity in the most intensely stained cells is three orders of magnitude higher than the staining intensity in negative cells. The "low" staining intensity refers to a staining intensity that is one or more orders of magnitude higher than the staining intensity in negative cells and is less than two orders of magnitude higher than the staining intensity in negative cells.

The negative cells represent the cell population having the lowest fluorescence intensity, for example, the cell population in the left lower area in FIG. 8.

For human hepatic nonparenchymal cell populations, when the expression of CD31 and CD45 is detected by flow cytometry, and the expression levels of CD31 and CD45 are plotted on the X-axis and Y-axis, respectively, two distinguishable cell populations (areas) from each other with a high cell density appear in addition to signals that may result from cells that do no express these molecules, autofluorescence, and non-specific fluorescence from debris. These two areas can be shown as an area that is enclosed by a contour line unconnected to contour lines in other areas in a contour plot based on the cell density. The CD31$^{high}$ CD45$^{low}$ cell population is one of the cell populations contained in the two areas and has a high expression level of CD31 and a low expression level of CD45 compared with the other cell population when these expression levels are compared at the highest cell density in each cell population. The CD31$^{low}$ CD45$^{high}$ cell population is the other of the cell populations contained in the two areas and has a low expression level of CD31 and a high expression level of CD45 compared with one cell population when these expression levels are compared at the highest cell density in each cell population.

The CD31$^{high}$ CD45$^{low}$ cell population is a cell population that has a fluorescence intensity of CD31 ranging from 400 to 7000 and a fluorescence intensity of CD45 ranging from 100 to 4000 in the detection of CD31 and CD45 expressions by flow cytometry when the mean fluorescence intensities of CD31 and CD45 in negative cells are about 7 and about 70, respectively, and the staining intensities of CD31 and CD45 in the most intensely stained cells are about 7000 and about 70000, respectively. The CD31$^{low}$ CD45$^{high}$ cell population is a cell population that has a fluorescence intensity of CD31 ranging from 30 to 1000 and a fluorescence intensity of CD45 ranging from 5000 to 70000 in the detection of CD31 and CD45 expressions by flow cytometry when the mean fluorescence intensities of CD31 and CD45 in negative cells are about 7 and about 70, respectively, and the staining intensities of CD31 and CD45 in the most intensely stained cells are about 7000 and about 70000, respectively.

In a more preferred aspect of the present invention, the organ-derived cell population is a human hepatic nonparenchymal cell population, and the cell population indicated by P1 or P2 in FIG. 8 is sorted in step (ii).

In a preferred aspect of the present invention, the organ-derived cell population is a monkey hepatic nonparenchymal cell population, and the CD31$^{low}$ CD45$^{high}$ cell population, CD31$^{intermediate}$ CD45$^{intermediate}$ cell population, or CD31$^{high}$ CD45$^{low}$ cell population is sorted in step (ii).

In this aspect, the CD31$^{low}$ CD45$^{high}$ cell population means a cell population having a "low" staining intensity (expression level) of CD31 and a "high" expression level of CD45. The CD31$^{intermediate}$ CD45$^{intermediate}$ cell population means a cell population having an "intermediate" staining intensity (expression level) of CD31 and an "intermediate" expression level of CD45. The CD31$^{high}$ CD45$^{low}$ cell population means a cell population having a "high" staining intensity (expression level) of CD31 and a "low" expression level of CD45.

For CD31, the "intermediate" staining intensity refers to a staining intensity that is the same degree as or one order of magnitude higher than the staining intensity in negative cells when the staining intensity in the most intensely stained cells is three orders of magnitude higher than the staining intensity in negative cells. The "high" staining intensity refers to a staining intensity that is one to three orders of magnitude higher than the staining intensity in negative cells. The "low" staining intensity refers to a staining intensity that is the same degree as or one order of magnitude higher than the staining intensity in negative cells.

For CD45, the "intermediate" staining intensity refers to a staining intensity that is one to two orders of magnitude higher than the staining intensity in negative cells when the staining intensity in the most intensely stained cells is two orders of magnitude higher than the staining intensity in negative cells. The "high" staining intensity refers to a staining intensity that is one to two orders of magnitude higher than the staining intensity in negative cells. The "low" staining intensity refers to a staining intensity that is the same degree as or one order of magnitude higher than the staining intensity in negative cells.

The negative cells represent the cell population having the lowest fluorescence intensity, for example, the cell population in the left lower area in FIG. 2.

In FIG. 2, P1 and P2 represent the CD31$^{low}$ CD45$^{high}$ cell population and CD31$^{intermediate}$ CD45$^{intermediate}$ cell population, respectively. As shown in FIG. 2, P1 and P2 are distinguishable from each other due to the relationship in which the fluorescence intensity of CD31 in P2 is higher than that in P1 and the fluorescence intensity of CD45 in P2 is lower than that in P.

For monkey hepatic nonparenchymal cell populations, when the expression of CD31 and CD45 is detected by flow cytometry, and the expression levels of CD31 and CD45 are plotted on the X-axis and Y-axis, respectively, three distinguishable cell populations (areas) from each other with a high cell density appear in addition to signals that may result from cells that do not express these molecules, autofluorescence, and non-specific fluorescence from debris. These three areas can be shown as an area that is enclosed by a contour line unconnected to contour lines in other areas in a contour plot based on the cell density. The $CD31^{low}$ $CD45^{high}$ cell population is one of the cell populations in the three areas and has the lowest expression level of CD31 and the highest expression level of CD45 when these expression levels are compared at the highest cell density in each cell population. The $CD31^{intermediate}$ $CD45^{intermediate}$ cell population is one of the cell populations in the three areas and has the second highest expression levels of CD31 and CD45 when these expression levels are compared at the highest cell density in each cell population. The $CD31^{high}$ $CD45^{low}$ cell population is one of the cell populations in the three areas and has the highest expression level of CD31 and the lowest expression level of CD45 when these expression levels are compared at the highest cell density in each cell population.

The $CD31^{low}$ $CD45^{high}$ cell population is a cell population that has a fluorescence intensity of CD31 ranging from 50 to 1500 and a fluorescence intensity of CD45 ranging from 8000 to 70000 in the detection of CD31 and CD45 expressions by flow cytometry when the mean fluorescence intensities of CD31 and CD45 in negative cells are each about 200, and the staining intensities of CD31 and CD45 in the most intensely stained cells are about 150000 and about 70000, respectively.

The $CD31^{intermediate}$ $CD45^{intermediate}$ cell population is a cell population that has a fluorescence intensity of CD31 ranging from 500 to 3000 and a fluorescence intensity of CD45 ranging from 4000 to 20000 in the detection of CD31 and CD45 expressions by flow cytometry when the mean fluorescence intensities of CD31 and CD45 in negative cells are each about 200, and the staining intensities of CD31 and CD45 in the most intensely stained cells are about 150000 and about 70000, respectively.

The $CD31^{high}$ $CD45^{low}$ cell population is a cell population that has a fluorescence intensity of CD31 ranging from 9000 to 150000 and a fluorescence intensity of CD45 ranging from 50 to 3000 in the detection of CD31 and CD45 expressions by flow cytometry when the mean fluorescence intensities of CD31 and CD45 in negative cells are each about 200, and the staining intensities of CD31 and CD45 in the most intensely stained cells are about 150000 and about 70000, respectively.

Alteration of the mean fluorescence intensity in negative cells that is used as a criterion will also result in variation of the fluorescence intensity range.

In a more preferred aspect of the present invention, the organ-derived cell population is a monkey hepatic nonparenchymal cell population, and the cell population indicated by any of P1, P2, and P3 in FIG. 2 is sorted in step (ii).

In step (iii), the uptake amount of the nucleic acid is measured in the cell population that have undergone steps (i) and (ii).

The uptake amount of the nucleic acid can be quantified by labeling the nucleic acid and detecting the signal intensity of the label. Such labels include those used for labeling of the antibody. Any method typical in the art may be used for the method for labeling a nucleic acid. Labels for nucleic acids can be a label distinguishable from labels for Stabilin, CD31, and CD45.

In a preferred aspect, a nucleic acid is labeled with a fluorescent label to measure the uptake amount of the nucleic acid in a flow cytometer.

II-2. Composition for an Uptake Assay of a Nucleic Acid

The second aspect of the present invention relates to a composition for an uptake assay of a nucleic acid (hereinafter also referred to as Composition II of the present invention). The nucleic acid uptake assay refers to a test in which a cellular uptake of a nucleic acid is assessed. In a preferred aspect, the assay is performed using the Measurement Method II of the present invention.

The Composition II of the present invention comprises an isolated organ-derived cell population expressing Stabilin. In the present invention, the term "isolated" refers to a state separated from an organ. In one aspect, the cell population is a partially purified cell population.

The "organ" in the present invention includes organs within a living body harboring cell populations, and also includes blood and bone marrow. In one aspect, the organ is liver, mesenteric lymph node, blood, bone marrow, stomach, lung, or spleen, and preferably liver.

The cell population may be any cell population in which the expression of Stabilin can be detected using a method generally used in the art (e.g., a method for detecting Stabilin described in the section II-1 above).

In one aspect, the organ-derived cell population is sorted based on the expression levels of CD31 and CD45 to identify the cell population expressing Stabilin.

In a preferred aspect, the organ-derived cell population comprised in the Composition II of the present invention is a human hepatic nonparenchymal cell population, and is a $CD31^{high}$ $CD45^{low}$ cell population or $CD31^{low}$ $CD45^{high}$ cell population. In a more preferred aspect, the organ-derived cell population comprised in the Composition II of the present invention is a human hepatic nonparenchymal cell population which consists of the cell population indicated by P1 or P2 in FIG. 8.

In another preferred aspect, the organ-derived cell population comprised in the Composition II of the present invention is a monkey hepatic nonparenchymal cell population, and is a $CD31^{low}$ $CD45^{high}$ cell population, $CD31^{intermediate}$ $CD45^{intermediate}$ cell population, or $CD31^{high}$ $CD45^{low}$ cell population. In a more preferred aspect, the organ-derived cell population comprised in the Composition II of the present invention is a monkey hepatic nonparenchymal cell population which consists of a cell population indicated by any of P1, P2, and P3 in FIG. 2.

These cell populations, which express Stabilin, are suitable for assessing uptake of a nucleic acid.

The Composition II of the present invention may comprise a medium as well as a cell population. The medium can be appropriately selected according to the organ type and animal species. Examples of the medium for cell populations derived from human liver include OptiThaw Kupffer Cell Thaw/Culture Media (Sekisui XenoTech). Examples of the medium for cell populations derived from monkey liver include HCM (LONZA).

The Composition II of the present invention can be produced using a method comprising (i) preparing organ-derived cells from an organ removed from a living body, and (ii) sorting the organ-derived cell population expressing Stabilin.

Steps (i) and (ii) can be performed according to the description in the section II-1 above.

II-3. Method for Screening for a Nucleic Acid

The third aspect of the present invention relates to a method for screening for an antibody having an antigen clearance function (hereinafter also referred to as Screening Method II of the present invention).

The Screening Method II of the present invention comprises the following steps:
(i) providing two or more nucleic acids that have an identical nucleotide sequence and each have a different chemical modification,
(ii) measuring a cellular uptake amount of each of the two or more nucleic acids provided in the step (i) using the Measurement Method II of the present invention, and
(iii) mutually comparing the cellular uptake amounts of the nucleic acids measured in the step (ii) to select the nucleic acid that has the desired uptake amount.

The two or more nucleic acids in step (i) that have an identical nucleotide sequence and each have a different chemical modification are each a modified form as described in the section II-1 above.

Step (ii) can be performed for each of the two or more nucleic acids according to the description in the section II-1 above.

The selected nucleic acids that have the desired cellular uptake amount in step (iii) can be used for application purposes (such as nucleic acid-based pharmaceutical products) suited for their characteristics.

All prior technical literatures cited herein are incorporated herein by reference.

The present invention will be described in more detail in the Examples.

EXAMPLES

Example 1 Preparation of Monkey Hepatic Nonparenchymal Cells

Monkey hepatic nonparenchymal cells obtained using the method as described later were purchased (from Ina Research Inc.) and used for quantification of the expression level of FcγRIIB and assessment of binding and uptake of an antibody-antigen complex to cells.

Specifically, 330 unit/kg of heparin sodium (Mochida Pharmaceutical Co., Ltd.) was intravenously administered to a cynomolgus monkey (*Macaca fascicularis*). The cynomolgus monkey was then killed via exsanguination under anesthesia with thiopental sodium (Mitsubishi Tanabe Pharma Corporation). Subsequently, laparotomy was performed to remove a whole lobe of the liver which was stored in cold William's E Medium (Thermo Fisher Scientific).

The liver was dissected into individual lobes into which Hanks-HEPES buffer containing glycol ether diaminetetraacetic acid (EGTA) was perfused for 6 to 10 minutes to remove blood. Additionally, 0.05% collagenase solution (Sigma Aldrich) was perfused for 6 to 8 minutes. The resulting liver was transferred to a culture dish to disperse liver cells which were then filtered with a gauze.

This cell suspension was centrifuged at 50×g at 4° C. for one minute to precipitate parenchymal cells. The supernatant was collected and centrifuged again. The supernatant was collected followed by centrifugation at 1000×g to precipitate nonparenchymal cells. The supernatant was discarded, and HBSS (+)(GIBCO) was added to the precipitate and suspended. Then, 39% OptiPrep (Alere Technologies) was layered over the suspension. This was centrifuged at 400×g at 4° C. for 15 minutes to collect the supernatant which was centrifuged at 3000 rpm at 4° C. for 5 minutes.

HCM (LONZA) was added to the precipitate and suspended. This suspension was defined as monkey hepatic nonparenchymal cells.

Example 2 Labeling of Anti-Monkey FcγRIIB Antibody and Monkey Myostatin with Alexa488

Each protein was labeled with Alexa488 using Alexa flour 488 labeling kit (Thermo Fisher Scientific) according to its accompanying protocol. The concentration of each protein and labeling efficiency of the fluorescent substance were determined by measuring absorbance in Nanodrop (Thermo Fisher Scientific) and performing calculation according to the equation described in the accompanying protocol.

Example 3 Identification of FcγRIIB-High Expression Cells in Monkey Hepatic Nonparenchymal Cells Pacific blue-labeled anti-CD31 antibody (BioLegend), APC-labeled anti-CD45 antibody (Miltenyi), and Alexa488-labeled anti-monkey FcγRIIB antibody (Sino Biological) were added to $2\times10^5$ monkey hepatic nonparenchymal cells to obtain a volume of 100 μL. The mixture was left to react under an ice cold condition for 30 minutes. The mixture was then centrifuged at 3000 rpm at 4° C. for 5 minutes to discard the supernatant. The precipitate was washed with PBS(−) and resuspended in PBS(−) with 2% FBS. The fluorescence of this cell solution was measured in FACS Canto II (Becton, Dickinson and Company) to create the forward-scattered light (FSC) vs side-scattered light (SSC) dot plot (FIG. 1). All cells on the FSC vs SSC dot plot were further subjected to Pacific blue (CD31) and APC (CD45) dot plotting (FIG. 2).

Hepatic nonparenchymal cells, which are a mixture of various cell populations such as vascular endothelial cells, Kupffer cells, and stellate cells, were allowed to be separated into three populations using two cell markers CD31 and CD45 also known as human LSEC cell markers. Each of the observed three cell populations was defined as P1 ($CD31^{Low}$ $CD45^{High}$), P2 ($CD31^{intermediate}$ $CD45^{intermediate}$), or P3 ($CD31^{High}$ $CD45^{Low}$) Dots observed in areas other than the three cell populations were eliminated from the analysis because the dots may result from autofluorescence from cells that do not express these markers and non-specific fluorescence from debris. Expression of monkey FcγRIIB was assessed by detecting the fluorescence intensity of Alexa488 (FITC filter detection) in these cell populations.

Figure 3:
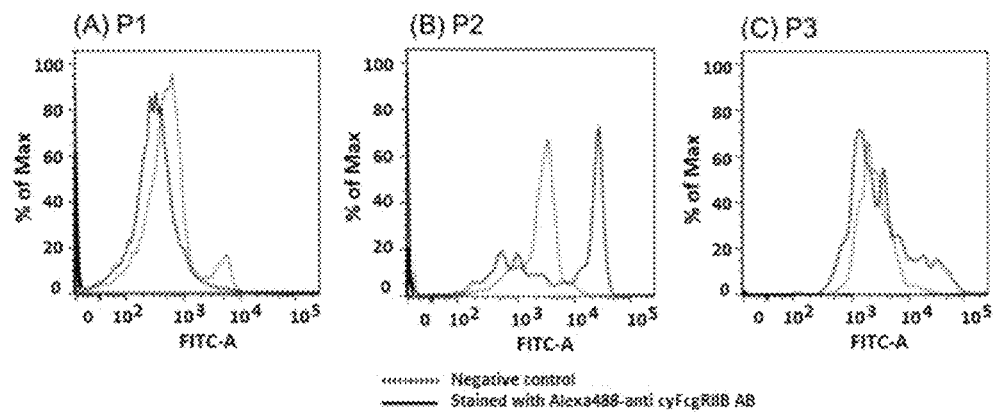
FIG. 3 is a histogram showing the fluorescence intensity of Alexa488 in each of P1 to P3 cell populations indicated in FIG. 2, in which monkey hepatic nonparenchymal cells are stained with Pacific Blue-labeled anti-CD31 antibody, APC-labeled anti-CD45 antibody, and Alexa488-labeled anti-monkey FcγRIIB antibody to measure respective fluorescence intensities in FACS. The black broken line shows the fluorescence signal from cells stained with Alexa488-labeled negative control antibody. The black solid line shows the fluorescence signal from cells stained with Alexa488-labeled anti-monkey FcγRIIB antibody.

Expression of monkey FcγRIIB was assessed in these cell populations. As shown in FIG. 3, the peak shift was not observed in P1 and P3 stained with anti-monkey FcγRIIB antibody relative to the negative control antibody labeled with Alexa488 (FIG. 3A, FIG. 3C) while an obvious peak shift to higher intensity was observed in P2 stained with anti-monkey FcγRIIB antibody. The results revealed that FcγRIIB was expressed only in P2.

It is difficult to identify FcγRIIB expressing cells without separation with the cell markers because the ratio of the FcγRIIB expressing cells to total cells is very low. However, identification of FcγRIIB expressing cells was allowed by staining cell markers CD31 and CD45 on the total cells and separating the total cells into individual cell populations.

This method does not use anti-FcγRIIB antibody for gating cell populations, and thus can quantify the expression level of FcγRIIB in a cell population of interest. The expression of monkey FcγRIIB was quantified using Quantum™ MESF (Bangs Laboratories) according to its accompanying protocol, and an expression of $1.8 \times 10^4$ molecules per cell was determined.

Example 4 Assessment of the Cellular Uptake of Antibody-Antigen Complexes in P2 Cell Population Comprised in Monkey Hepatic Nonparenchymal Cells (4-1) Characteristics of Fc of the Antibodies Used for Uptake Assessment of Antibody-Antigen Complexes Fc-containing anti-myostatin antibodies SG1, SG141, SG143 (also denoted as FS154), and SG145 (also denoted as FS156) described in WO 2016/117346 A1 (Patent Literature 4) and WO 2016/098357 A1 (Patent Literature 5) were used.

When the affinity of SG1 to monkey FcγRIIB is defined as 1.0, SG143 exhibits a 5 to 10-fold increased binding activity, and SG145 exhibits an about 1 to 2-fold increased binding activity (WO 2016/117346 A1). SG141, which is an Fc-containing antibody designed to have an increased pI and thus be positively charged, exhibits a binding capability that is 1.64-fold higher than the binding capability of SG1 in a binding test of immune complexes to monkey FcγRIIB using Biacore (WO 2016/098357 A1).

(4-2) Assessment of the Cellular Uptake of Antibody-Antigen Complexes

Alexa488-labeled monkey myostatin and each of the antibodies described above were added at final concentrations of 0.3 μg/mL and 0 to 40 g/mL, respectively to 50 μL of a cell solution containing $2 \times 10^5$ cells to obtain 100 μL of the reaction solution. This solution was left to react while stirring at 37° C. for 15 minutes. The solution was then ice-cooled, and cold PBS with 2% FBS was added to wash the cells. The cell solution was then centrifuged (at 3000 rpm for 5 min) to discard a liquid. The cells were stained with an anti-CD31 antibody and an anti-CD45 antibody. After washing, the fluorescence intensity of Alexa488 in P1, P2, and P3 was measured in FACS Canto II.

Figure 4:
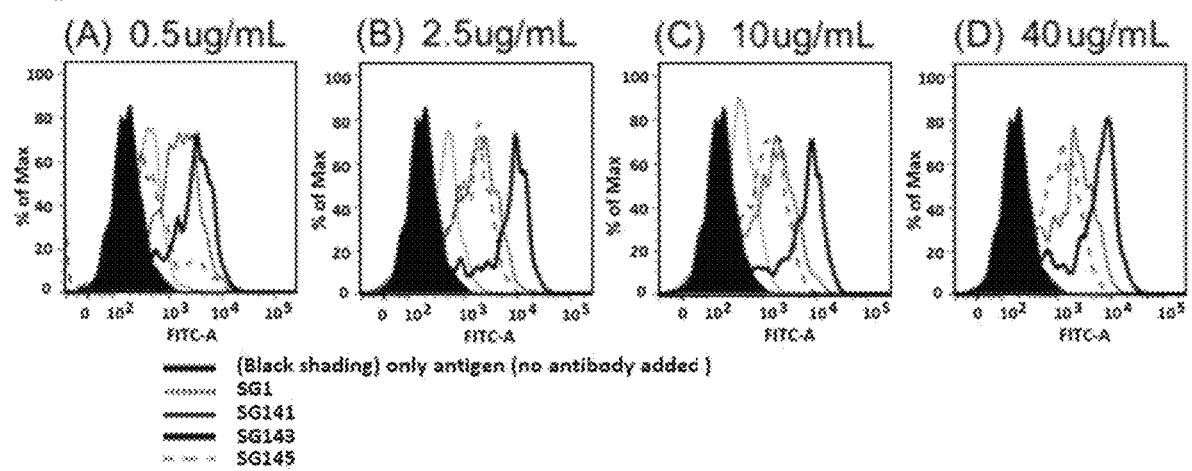
FIG. 4 is a histogram showing the fluorescence intensity of Alexa488-labeled monkey myostatin in P2, in which the antibody described in Example 4 was mixed with Alexa488-labeled monkey myostatin to form an antibody-antigen complex which was added to a cell solution to cause uptake before identifying P2 cell population from cells stained with Pacific Blue-labeled anti-CD31 antibody and APC-labeled anti-CD45 antibody in a scatter diagram as shown in FIG. 1 and FIG. 2. The black shading is a histogram when no antibody (only Alexa488-labeled monkey myostatin) was added. The black short broken line is a histogram when the mixture of Alexa488-labeled latent monkey myostatin and SG1 was added. The black long broken line is a histogram when the mixture of Alexa488-labeled latent monkey myostatin and SG145 was added. The black solid line is a histogram when the mixture of Alexa488-labeled latent monkey myostatin and SG141 was added. The black thick line is a histogram when the mixture of Alexa488-labeled latent monkey myostatin and SG143 was added. Each antibody was added at a concentration of 0.5 (A), 2.5 (B), 10 (C), or 40 (D) g/mL, respectively.

The results demonstrated that in P1 and P3, the fluorescence peak shift of Alexa488-labeled myostatin in the presence of the antibodies was not greater than that in the absence of the antibodies. On the other hand, in P2, the fluorescence peak of Alexa488-labeled myostatin was shifted to higher intensity at any antibody concentration in the order of the absence of antibody, SG1, SG145, SG141, and SG143 (FIG. 4). Thus, it is indicated that the antibody-antigen complex binds to FcγRIIB on a cell surface, and are then incorporated into cells according to individual Fc characteristics.

(4-3) Quantification of Antigen Uptake

The fluorescence intensity of fluorescently labeled standard beads was measured using Quantum™ MSF (Bangs Laboratories) according to its accompanying protocol. The geometric mean fluorescence intensity of each standard was used to create a calibration curve according to the accompanying protocol. The amount of monkey myostatin incorporated in the presence of each antibody at each concentration was calculated from the geometric mean fluorescence intensities in samples for monkey myostatin uptake.

Figure 5:
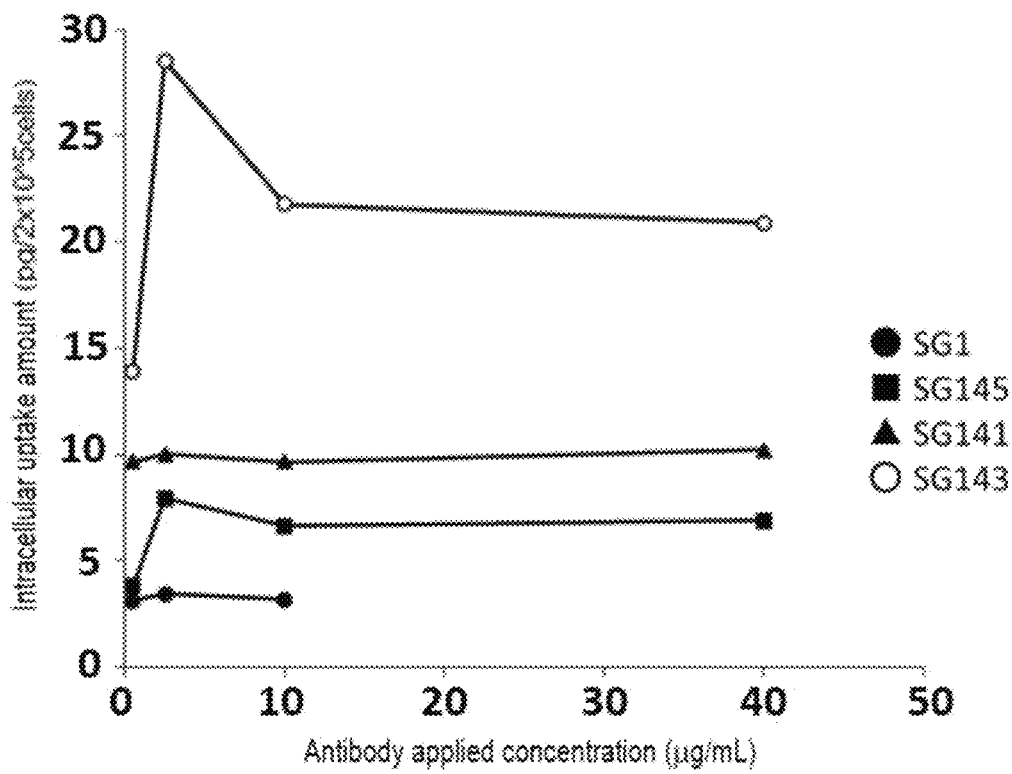
FIG. 5 shows the cellular uptake amounts determined from the histograms shown in FIG. 4 against the amount of the antibody added. The black circle, black triangle, white circle, and black square show SG1, SG141, SG143, and SG145, respectively.

The results are shown in FIG. 5. At all of the concentrations assessed, the uptake amount in the presence of SG143 was the highest, followed by SG141, SG145, and SGT in this order. The uptake amount in the presence of each antibody at an antibody-applied concentration of 0.5 μg/mL was the same degree as or higher than that at higher antibody-applied concentrations.

Example 5 Correlation Between In Vitro Uptake of Monkey Myostatin into Monkey Hepatic Nonparenchymal Cells and In Vivo Antigen Reduction Rate (5-1) Assessment of In Vivo Antigen Reduction Rate in Monkey When SG, SG141, SG143, or SG145, which is an antibody directed against monkey myostatin, is administered to a monkey, monkey myostatin and the antibody form an immune complex. It is believed that the immune complex is incorporated into cells highly expressing FcγRIIB and eliminated from the blood. The blood concentration of monkey myostatin was measured using the published method (WO 2016/098357 A1) 14 days after antibody administration to calculate the reduction rate upon administration of each antibody by defining the myostatin concentration in SG administration as 1. A specific method is as follows.

Accumulation of endogenous myostatin was assessed in vivo by administering an anti-latent myostatin antibody to 2 to 4 years old *Macaca fascicularis* (cynomolgus monkey) (Shin Nippon Biomedical Laboratories Ltd., Japan) from Cambodia. The antibody was administered to the cephalic antebrachial vein at a dosage level of 30 mg/kg with a disposable syringe, an extension tube, an indwelling needle, and an infusion pump. The administration was performed for 30 minutes per animal. Blood was taken either at pre-administration, at 5 minutes, 7 hours, and 1, 2, 3, 7, 14, 21, 28, 35, 42, 49, and 56 days after administration completion, or at 5 minutes, 2, 4, and 7 hours, and 1, 2, 3, 7, 14, 21, 28, 35, 42, 49, and 56 days after administration completion. Blood was taken from femoral vein with a heparin sodium-containing syringe. The blood was immediately cooled on ice and centrifuged at 1700×g at 4° C. for 10 minutes to obtain plasma. The plasma sample was stored in an ultra-deep freezer (acceptable range: −70° C. or lower) until measurement. Myostatin concentration in the plasma sample was measured with electrochemical luminescence (ECL).

Figure 6:
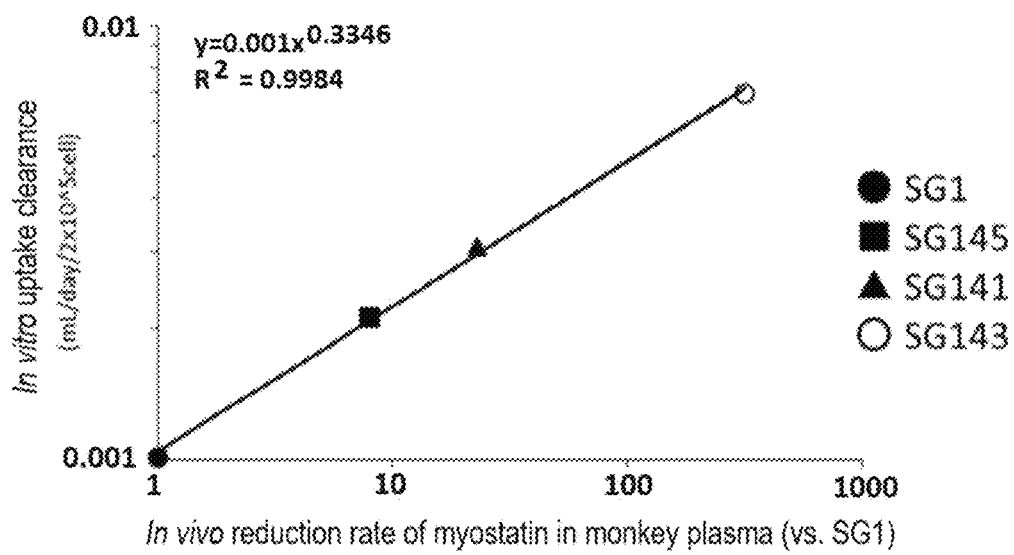
FIG. 6 is a plot of the cellular uptake amount of myostatin into monkey hepatic nonparenchymal cells against in vivo reduction rate of monkey myostatin in monkey in each sample and shows correlation between the cellular uptake amount and the reduction rate. The reduction rate of myostatin in monkey plasma was shown as the reduction rate of myostatin of each sample determined by measuring the concent

(5-2) Correlation Between In Vivo Monkey Myostatin Reduction Rate and In Vitro Cellular Uptake Clearance The value of uptake clearance converted from the in vitro cellular uptake amount of monkey myostatin described above was plotted for each antibody against the in vivo reduction rate of monkey myostatin from plasma (FIG. 6). The results revealed a positive correlation between the in vivo reduction rate of monkey myostatin in each plasma sample relative to SG1 and the in vitro uptake amount of monkey myostatin in monkey hepatic nonparenchymal cells. SG143, which was the most intracellularly incorporated antibody, allowed myostatin in plasma to be decreased in vivo, while SG1 had the lowest cellular uptake amount and the lowest reduction rate from plasma. The ranking of cellular uptake amount among antibodies intimately correlated with the myostatin reduction rate in plasma. When antibodies that have a different mechanism to increase the myostatin reduction rate, such as an Fc-containing antibody with an increased affinity to FcγRIIB and an antibody having a positively charged Fc, are even used, the ranking of cellular uptake amount also reflected the results of in vivo reduction rate.

The results demonstrate that the cellular uptake assessment system in monkey hepatic nonparenchymal cells of the present invention can predict the in vivo antigen reduction rate in monkey by employing various antibodies that have a different mechanism to increase the myostatin reduction rate from monkey plasma, such as an Fc-containing antibody with an increased affinity to FcγRIIB and an Fc-containing antibody having a modified isoelectric point (pI).

Example 6 Preparation of Human Hepatic Nonparenchymal Cells

Human hepatic nonparenchymal cells were purchased from Sekisui Xenotech, LLC. The preparation procedure was as follows. Human liver was perfused with a collagenase solution to digest the tissue. Filtration through filters was then performed, and the cell suspension was diluted with DMEM. The diluted cell suspension was centrifuged at 100×g for 5 minutes to precipitate parenchymal cells and collect the supernatant. The supernatant was further centrifuged at 350×g for 10 minutes to precipitate nonparenchymal cells. The supernatant was then discarded, and the precipitate was resuspended in OptiThaw Kupffer Cell Thaw/Culture Media (Sekisui XenoTech).

Example 7 Labeling of Anti-Human FcγRIIB Antibody and Human Myostatin with Alexa647 or Alexa488

Each protein was labeled with Alexa647 or Alexa488 using Alexa flour 647 labeling kit (Thermo Fisher Scientific) or Alexa flour 488 labeling kit (Thermo Fisher Scientific) according to their accompanying protocols. The concentration of each protein and labeling efficiency of fluorescent substances were determined by measuring absorbance in Nanodrop (Thermo Fisher Scientific) and performing calculation according to the equation described in the accompanying protocols.

Figure 7:
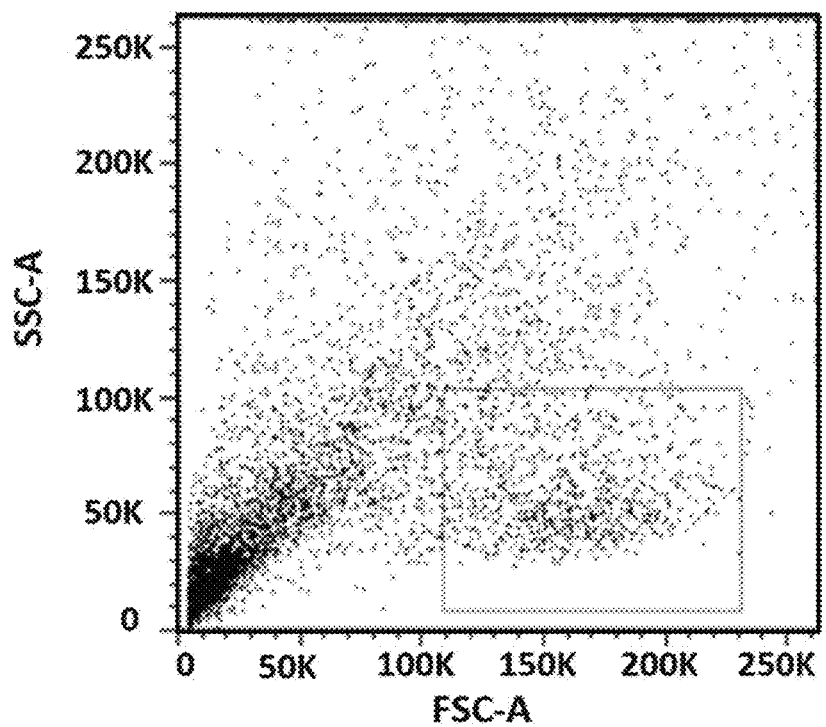

Example 8 Identification of FcγRIIB-High Expression Cells in Human Hepatic Nonparenchymal Cells FITC-labeled anti-CD31 antibody (Miltenyi), VioBlue-labeled anti-CD45 antibody (Miltenyi), anti-human FcγRIIB human IgG antibody (Clone 2B6), and Alexa647-labeled anti-human antibody (Southern Biotech) were added to $5 \times 10^5$ human hepatic nonparenchymal cells to obtain a volume of 100 µL. The mixture was left to react under an ice cold condition for 60 minutes. The mixture was then centrifuged at 600×g at 4° C. for 3 minutes to discard the supernatant. The precipitate was washed with PBS(−) and resuspended in PBS(−) with 2% FBS. The fluorescence of this cell solution was measured in FACS Canto II (Becton, Dickinson and Company) to create the forward-scattered light (FSC) vs side-scattered light (SSC) dot plot (FIG. 7). Cells in the area surrounded by the rectangle were further subjected to FITC (CD31; FITC filter detection) and VioBlue (CD45; Pacific Blue filter detection) dot plotting (FIG. 8).

Hepatic nonparenchymal cells, which are a mixture of various cell populations such as vascular endothelial cells, Kupffer cells, and stellate cells, were allowed to be separated into two populations using two cell markers CD31 and CD45 known as human LSEC cell markers. Each of the observed two cell populations was defined as P1 (CD31LowCD45High) or P2 (CD31HighCD45Low). Dots observed in areas other than the two cell populations were eliminated from the analysis because the dots may result from cells that do not express these markers, autofluorescence, or non-specific fluorescence from debris.

Figure 9:
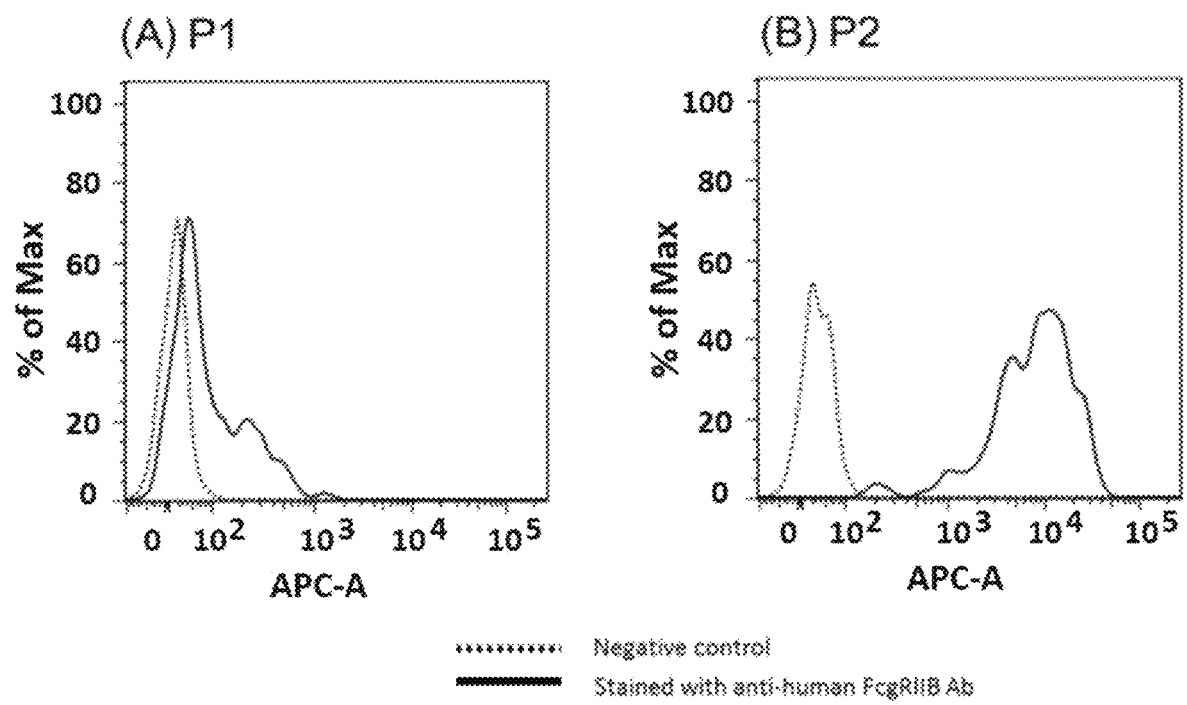

Expression of human FcγRIIB was assessed in these cell populations. As shown in FIG. 9, no peak shift due to addition of anti-human FcγRIIB antibody was observed in P1 as with the negative control antibody (FIG. 9A) while an obvious peak shift to higher intensity due to anti-human FcγRIIB antibody was observed in P2. The results revealed that FcγRIIB was expressed only in P2 (FIG. 9B). It is difficult to identify FcγRIIB expressing cells without gating these cells with cell markers because the ratio of the FcγRIIB expressing cells to total cells is very low. However, identification of FcγRIIB expressing cells is allowed by staining cell markers CD31 and CD45 on the total cells and separating the total cells into individual cell populations as in this technique.

Additionally, this method does not use anti-FcγRIIB antibody for gating cell populations, and thus can quantify the expression level of FcγRIIB in a cell population of interest. The expression of human FcγRIIB was quantified using Quantumn™ MESF (Bangs Laboratories) according to its accompanying protocol, and an expression of $2.0 \times 10^5$ molecules per cell was determined.

Example 9 Assessment of the Cellular Uptake of Antibody-Antigen Complex in P2 Cell Population Comprised in Human Hepatic Nonparenchymal Cells (9-1) Characteristics of Fc of the Antibody Used for Incorporation Assessment of the Antibody-Antigen Complex Anti-myostatin antibody TT91 described in WO 2016/098357 A1 was used.

When the affinity of SG1 to human FcγRIIB is defined as 1.0, TT91 exhibits 14.7-fold increased binding activity (WO 2016/098357 A1).

(9-2) Assessment of the Cellular Uptake of Immune Complexes

Alexa488-labeled human myostatin and each antibody were added at final concentrations of 0.3 µg/mL and 0.1, 1, 10, or 100 µg/mL, respectively to 50 µL of cell solution containing $5 \times 10^5$ human hepatic nonparenchymal cells to obtain 100 µL of reaction solution. This solution was left to react while stirring at 37° C. for 60 minutes. After reaction, the solution was then ice-cooled, and cold PBS with 2% FBS was added to wash the cells. The cell solution was then centrifuged (at 600×g for 3 min) to discard a liquid. The cells were stained with an anti-CD31 antibody and an anti-CD45 antibody. After washing, the fluorescence intensity of Alexa488 in P2 was measured in FACS Canto II.

Figure 10:
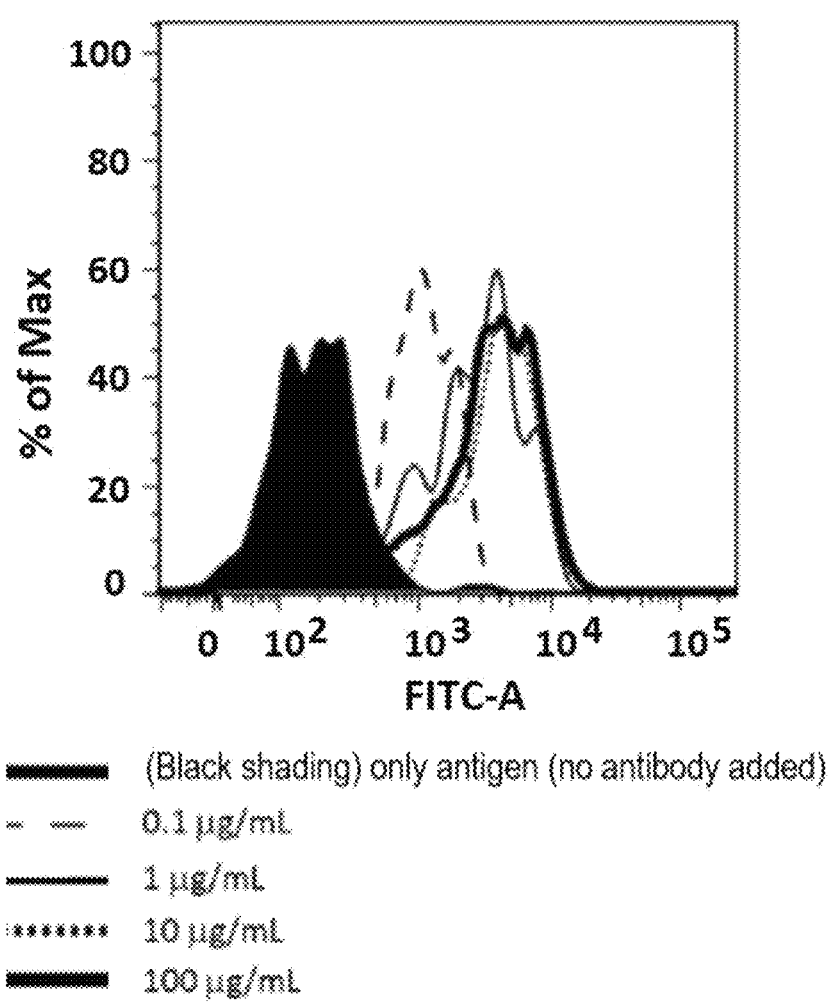

The results indicated that the fluorescence peak of Alexa488-labeled myostatin was shifted to higher intensity in the order of the absence of antibody, 0.1, 1, and 10 µg/mL TT91 antibody (FIG. 10), and that the antibody-antigen complex binds to FcγRIIB on a cell surface and is incorporated into cells in an antibody concentration-dependent manner. The peak shift to higher intensity which was also observed at an antibody concentration of 100 µg/mL was similar to that at 10 g/mL.

Example 10 Quantification of Antigen Uptake

The fluorescence intensity of fluorescently labeled standard beads was measured using Quantum™ MSF (Bangs Laboratories) according to its accompanying protocol. The geometric mean fluorescence intensity of each standard was used to create a calibration curve according to the accompanying protocol. The amount of human myostatin incorporated in the presence of each antibody at each concentration was calculated from the geometric mean fluorescence intensities in samples for human myostatin uptake.

Figure 11:
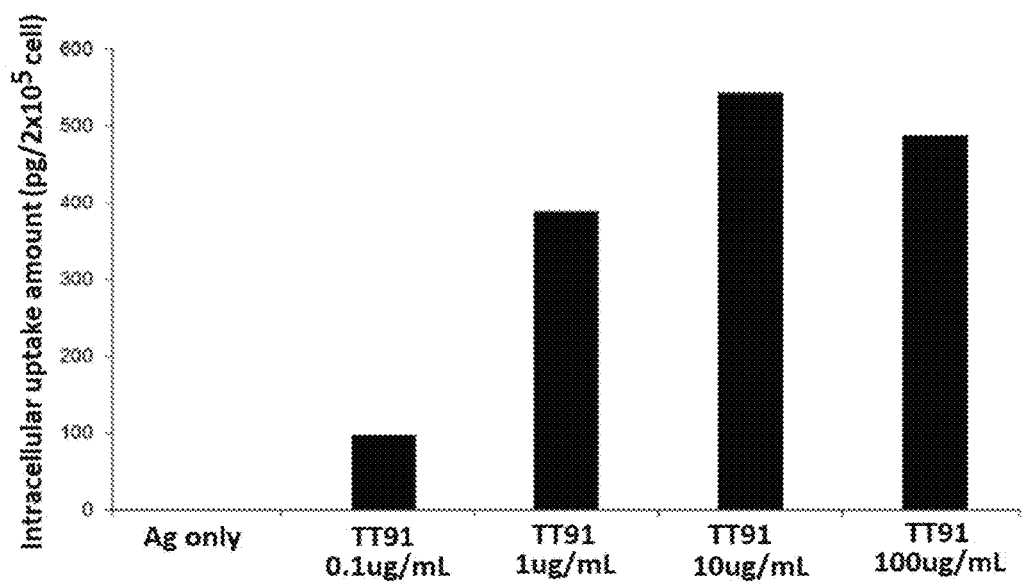

The results are shown in FIG. 11. The uptake amounts increased in an antibody concentration-dependent manner in the antibody applied groups as compared with the antibody non-applied group, and reach a plateau at 10 g/mL. This is probably because the ratio of TT91 antibody bound to Alexa488-labeled human myostatin increases with increased in antibody concentration, and thus the myostatin-bound antibody bound to cells, resulting in uptake. On the other hand, the uptake amount at 100 μg/mL was lower than that at 10 g/mL probably because the antibody unbound to human myostatin increased in the higher concentration, and the unbound antibody bound to FcγRIIB to be incorporated, leading to apparent decrease in the uptake amount of human myostatin-bound TT91.

Example 11 Uptake of a Nucleic Acid in Monkey Hepatic Nonparenchymal Cells

As for the monkey species, cynomolgus monkey (*Macaca fascicularis*) was used. The FITC-labeled oligodeoxynucleotide nucleic acid as described in Non Patent Literature 25 (J Hepatol., 2006. 44(5):939-46) was purchased from Hokkaido System Science Co., Ltd. and used as a test substance. The sequence is 5'-FITC-T*C*C*-A*TG-ACG-TTC-CTGA*T*G*-C*T-3'. The asterisk (*) indicates a phosphorothionucleotide.

(11-1) Assessment of the Expression of Stabilin 1 and Stabilin 2 in Monkey Hepatic Nonparenchymal Cells Pacific blue-labeled anti-CD31 antibody (BioLegend), APC-labeled anti-CD45 antibody (Miltenyi), and Alexa488-labeled anti-Stabilin 1 or anti-Stabilin 2 antibody (Thermo Fisher Scientific) were added to $2\times10^5$ monkey hepatic nonparenchymal cells to obtain a volume of 100 μL. The mixture was left to react under an ice cold condition for 30 minutes. The mixture was then centrifuged at 3000 rpm at 4° C. for 5 minutes to discard the supernatant. The precipitate was washed with PBS(-) and resuspended in PBS(-) with 2% FBS. The fluorescence of this cell solution was measured in FACS Canto II (Becton, Dickinson and Company) to create the forward-scattered light (FSC) vs side-scattered light (SSC) dot plot. All cells on the FSC vs SSC dot plot were further subjected to Pacific blue (CD31) and APC (CD45) dot plotting.

Figure 12:
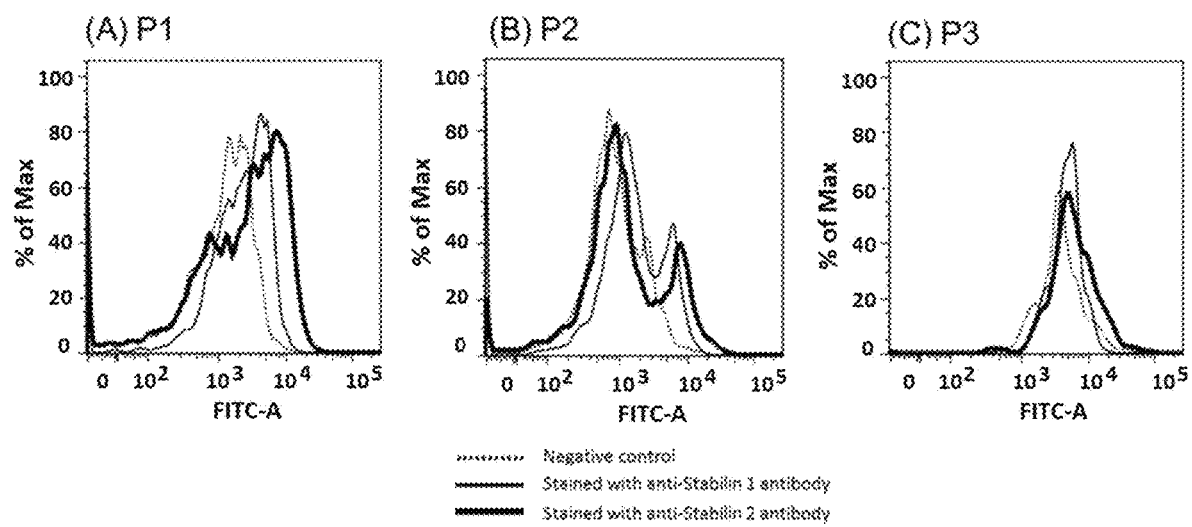

Each of the observed three cell populations was defined as P1 ($CD31^{Low}CD45^{High}$), P2 ($CD31^{intermediate}CD45^{intermediate}$), or P3 ($CD31^{High}CD45^{Low}$). Plots observed in areas other than the three cell populations were eliminated from the analysis because the dots may result from cells that do not express these markers, autofluorescence, and non-specific fluorescence from debris. Expression of Stabilin 1 and Stabilin 2 was assessed by detecting the fluorescence intensity of Alexa488 (FITC filter detection) in the three cell populations. As shown in FIG. 12, the peak shift to higher fluorescence intensity due to addition of anti-Stabilin 1 antibody or anti-Stabilin 2 antibody was observed in all of P1 to P3 cell populations in varying degrees relative to the Alexa488-labeled negative control antibody (FIGS. 12A to C).

(11-2) Assessment of the Cellular Uptake of Nucleic Acid in Monkey Hepatic Nonparenchymal Cells The FITC-labeled nucleic acid was added at final concentrations of 0 to 40 μg/mL to 50 μL of cell solution containing $2\times10^5$ cells to obtain 100 μL of reaction solution. This solution was left to react while stirring at 37° C. for 30 minutes. The solution was then ice-cooled, and cold PBS with 2% FBS was added to wash the cells. The cell solution was then centrifuged (at 3000 rpm for 5 min) to discard a liquid. The cells were stained with an anti-CD31 antibody and an anti-CD45 antibody. After washing, the fluorescence intensity of FITC in P1, P2, and P3 was measured in FACS Canto II.

The results demonstrated that in all of P1 to P3 cell populations, the fluorescence peak was observed at a high intensity in any of nucleic acid concentrations with addition of the nucleic acid, as compared with the condition of no addition of the nucleic acid. Particularly, the peak shift was observed in P2 and P3 in an applied concentration-dependent manner.

Figure 13:
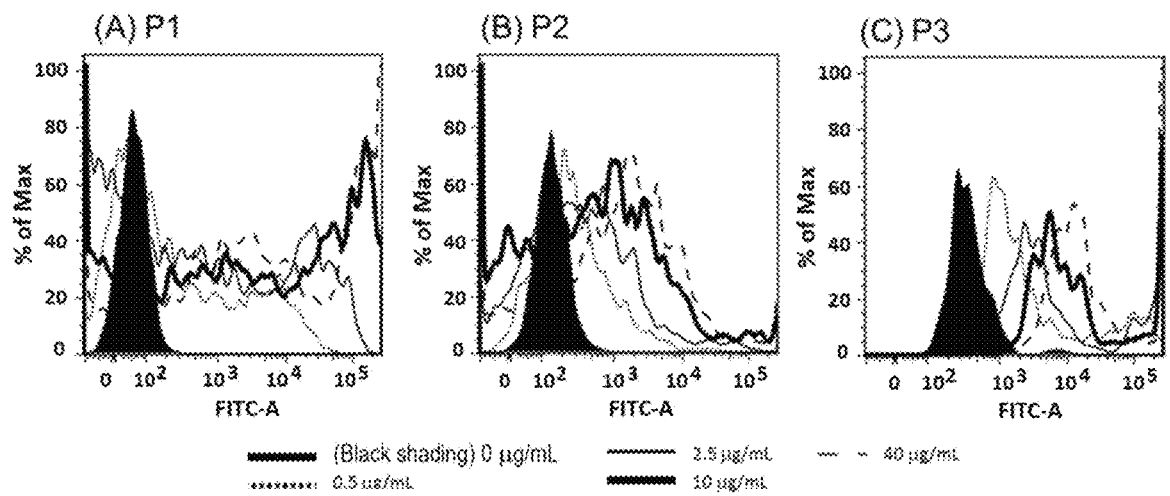
Figure 14:
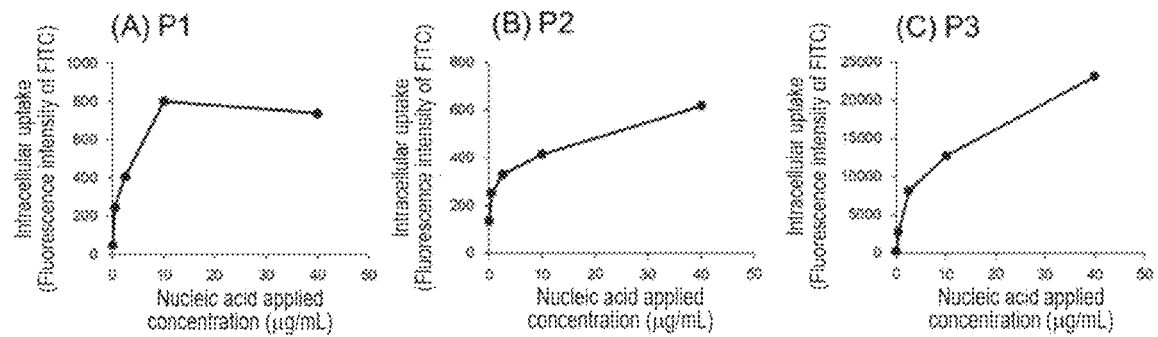
FIG. 14 shows the cellular uptake representing the mean fluorescence intensity in the histogram shown in FIG. 13 against the amount of the antibody added to each cell population.

(11-3) Correlation Between the Applied Concentration of Nucleic Acids and the Uptake Amount of Nucleic Acid The applied concentration-dependent cellular uptake was assessed by plotting the applied concentration of the nucleic acid against the mean fluorescence intensity of the peak shown in FIG. 13. The results demonstrated that the applied concentration-dependent increase in FITC fluorescence intensity was observed in all of P1 to P3 cell populations, and the fluorescence intensity reaches saturation at a high concentration. This saturation may indicate that the nucleic acid is incorporated via a particular receptor.

Example 12 Assessment of the Cellular Uptake of Antibodies in P2 Cell Population in Monkey Hepatic Nonparenchymal Cells (12-1) Characteristics of Fc of Antibodies Used for Uptake Assessment Fc-containing anti-myostatin antibodies SG1, SG141, SG143 (also denoted as FS154), and SG1081 described in WO 2016/117346 A1 (Patent Literature 4) and WO 2016/098357 A1 (Patent Literature 5) were used.

Anti-myostatin antibodies, SG1, SG141, SG143 (also denoted as FS154), and SG1081, containing Fc described in WO 2016/117346 A1 (Patent Literature 4) and WO 2016/098357 A1 (Patent Literature 5) were used.

When the affinity of SG1 to monkey FcγRIIB is defined as 1.0, SG143 exhibits a 5 to 10-fold increased affinity (WO 2016/117346 A1). SG141, which is an Fc-containing antibody designed to have an increased pI and thus be positively charged at a neutral pH, exhibits a binding capability that is 1.64-fold higher than the binding capability of SG1 in a binding test of immune complexes to monkey FcγRIIB using Biacore (WO 2016/098357 A1). SG1081 has a5 to 10-fold increased affinity to monkey FcγRIIB compared with SG1 (WO 2016/117346 A1).

(12-2) Assessment of the Cellular Uptake of Antibodies

Each of Alexa488-labeled antibodies was added at final concentrations of 10 to 200 μg/mL to 50 μL of cell solution containing $2\times10^5$ monkey hepatic nonparenchymal cells prepared as in Example 1 to obtain 100 μL of reaction solution. This solution was left to react while stirring at 37° C. for 15 minutes. The solution was then ice-cooled, and a hepatocyte culture medium with 10 mM citrate (pH4.5, LONZA) was added to wash the cells. The cell solution was then centrifuged (at 3000 rpm for 3 min) to discard a liquid. The resulting cells were stained with an anti-CD31 antibody and an anti-CD45 antibody. After washing, the fluorescence intensity of Alexa488 in P1, P2, and P3 was measured in FACS Canto II.

Figure 15:
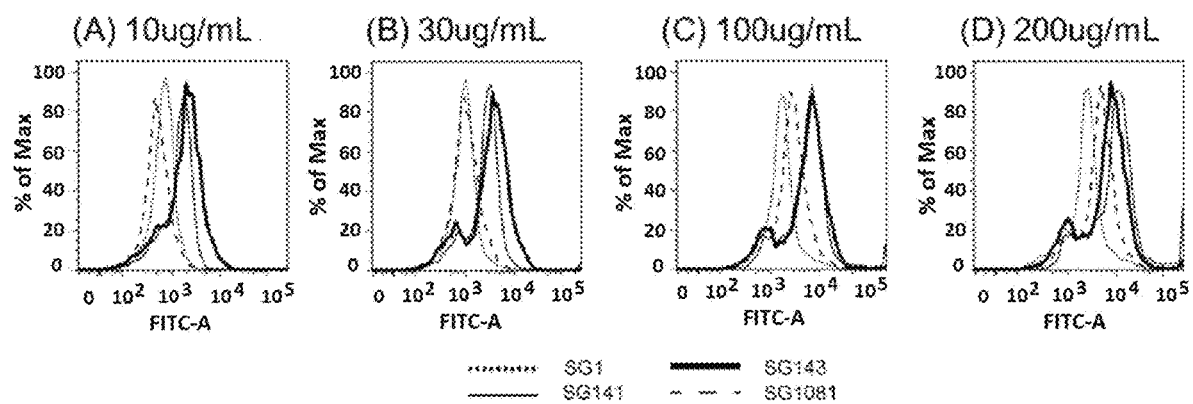
FIG. 15 is a histogram showing the fluorescence intensity of Alexa488-labeled antibody in P2, in which the Alexa488-labeled antibody described in Example XXX was added to a cell solution to cause uptake before identifying P2 cell population from cells stained with Pacific Blue-labeled anti-CD31 antibody and APC-labeled anti-CD45 antibody in a scatter diagram as shown in FIG. 1 and FIG. 2. The black short broken line, black long broken line, black solid line, and black thick line are histograms of Alexa488 when SG, SG1081, SG141, and SG143 were added, respectively. Each antibody was added at a concentration of 10 (A), 30 (B), 100 (C), or 200 (D) g/mL, respectively.

The results revealed that the fluorescence peaks of SG1, SG141, SG143, and SG1081 were observed in P2 cell population at any antibody concentration, and the fluorescence peaks were shifted to higher intensity as the antibody applied concentration increased (FIG. 15). The fluorescence intensities of SG141, SG143, and SG1081 were higher than that of SG1. Thus, it is indicated that the antibodies bind to FcγRIIB on a cell surface and are incorporated into cells according to individual Fc characteristics.

(12-3) Quantification of Antibody Uptake

The fluorescence intensity of fluorescently labeled standard beads was measured using Quantum™ MSF (Bangs Laboratories) according to its accompanying protocol. The geometric mean fluorescence intensity of each standard was used to create a calibration curve according to the accompanying protocol. The amount of the antibodies incorporated in the presence of each antibody at each concentration was calculated from the geometric mean fluorescence intensities in samples for the antibody uptake.

Figure 16:
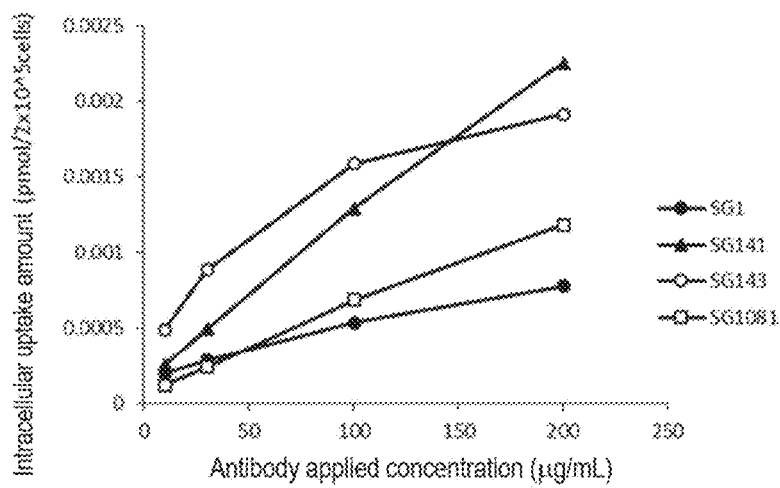
FIG. 16 shows the cellular uptake amount determined from the histograms shown in FIG. 15 against the amount of the antibody added. The black circle, black triangle, white circle, and black square show SG, SG141, SG143, and SG1081, respectively.

The results are shown in FIG. 16. At 10 μg/mL, the uptake amounts of SG1, SG1081, and SG141 were similar, and the uptake amount of SG143 was greater than these amounts. At 30 μg/mL, the uptake amounts of SG1 and SG1081 were similar, and then the uptake amount increased in the order of SG141 and SG143. At 100 μg/mL, the uptake amount of SG1 was the smallest, followed by SG1081, SG141, and SG143 in this order. At 200 μg/mL, the uptake amount of SG1 was the smallest, followed by SG1081, SG143, and SG141 in this order.

Additionally, the correlation between in vivo plasma clearance of each antibody in monkey and the cellular uptake amount of each antibody in this Example was examined. Clearance of antibodies in monkey plasma was measured using the following method. SG1, SG141, and SG143 were each administered at 30 mg/kg to 2 to 4 years old *Macaca fascicularis* (cynomolgus monkey)(Shin Nippon Biomedical Laboratories Ltd., Japan) from Cambodia, while SG1081 was administered at 2 mg/kg. Blood was taken successively until 56 days after administration and centrifuged to obtain plasma. Antibody concentration in plasma was measured with electrochemical luminescence (ECL). Plasma clearance was calculated using non-compartment model analysis. The cellular uptake amount in monkey hepatic nonparenchymal cells was determined from the fluorescence intensity of Alexa488-labeled antibody added at 200 μg/mL and was used for plotting.

Figure 17:
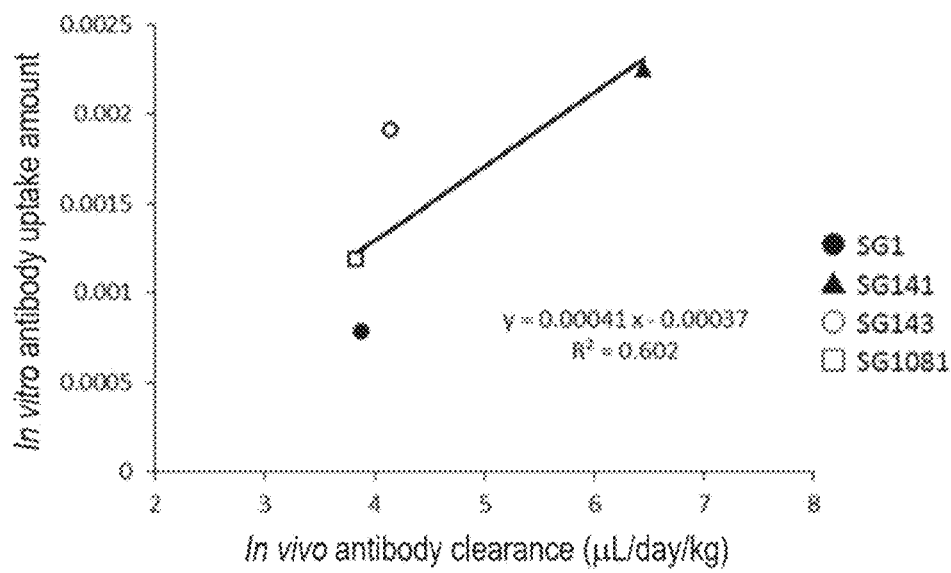
FIG. 17 is a plot of the in vivo elimination clearance of antibody from plasma in monkey and the in vitro cellular uptake amount of Alexa488-labeled antibody and shows correlation between the elimination clearance and the uptake amount. The antibody clearance in monkey plasma (plasma clearance) was calculated using non-compartment model analysis by administering SG1 (black circle), SG141 (black square), SG143 (black triangle), or SG1081 (white circle) to monkey and measuring the antibody concentration in plasma until 56 days after administration. The cellular uptake amount in monkey hepatic nonparenchymal cells used for the plot was determined from the fluorescence intensity of Alexa488-labeled antibody added at 200 μg/mL.

As shown in FIG. 17, correlation between the in vivo plasma clearance of antibody and the in vitro cellular uptake of antibody was observed ($R^2=0.602$).

Example 13 Validation of IL-6R Expression in FcγRIIB-High Expression Cells in Monkey Hepatic Nonparenchymal Cells At first, 50 μL of a cell solution containing $2\times10^5$ monkey hepatic nonparenchymal cells prepared as in Example 1 was prepared. An antibody solution containing Alexa488-labeled tocilizumab (humanized anti-IL-6R antibody) or Alexa488-labeled hIgG as a negative control at a final concentration of 3 g/mL was also prepared. An antibody solution containing Alexa488-labeled tocilizumab and non-labeled tocilizumab at a final concentration of 1 mg/mL which is excess relative to the labeled antibody was prepared to ensure specific binding. Fc Receptor Blocking Solution (Human TruStain FcX, Biolegend) was added to the cell solution and antibody solutions at 20×dilution for FcγR blocking. The cell solution and antibody solutions thus prepared were mixed to obtain 100 μL of reaction solution. The reaction solutions were left to react at 4° C. for 120 minutes. Cold PBS with 2% FBS was then added. The cells were washed by repeating centrifugation (at 3000 rpm for 3 min) and supernatant removal. The resulting cells were then stained with an anti-CD31 antibody and an anti-CD45 antibody. After washing, the fluorescence intensity of Alexa488 was measured in FACS Canto II.

Figure 18:
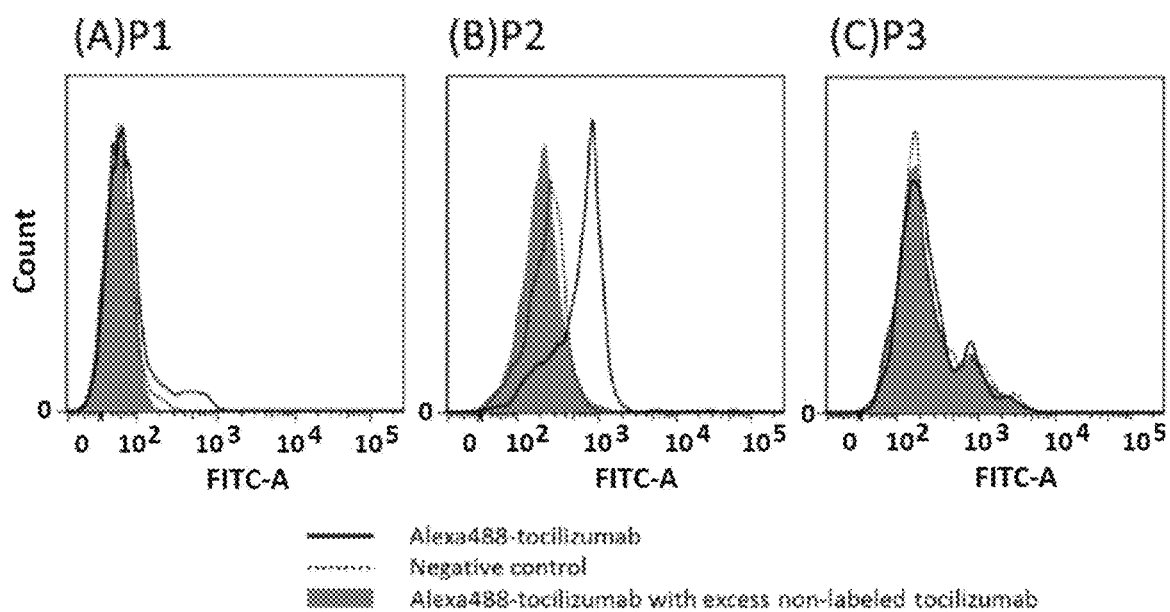
FIG. 18 (A) to (C) are histograms of the fluorescence intensity of Alexa488 in cell populations located in P1 to P3 identified from a scatter diagram similar to FIG. 2, in which monkey hepatic nonparenchymal cells were stained with Pacific Blue-labeled anti-CD31 antibody, APC-labeled anti-CD45 antibody, and Alexa488-labeled tocilizumab before measuring respective fluorescence intensities in FACS. The black broken line, black solid line, and gray shading show the result of reaction using Alexa488-labeled negative control antibody, Alexa488-labeled tocilizumab, and the solution containing Alexa488-labeled tocilizumab with an excess of non-labeled tocilizumab, respectively.

As in Example 3, the cell populations were assessed by plotting the expression levels of CD45 and CD31 on the Y-axis and X-axis, respectively to classify the cell populations based on the expression level pattern. FcγRIIB expression in P1 to P3 cell populations was detected as in Example 3, and the high expression of FcγRIIB was observed in P2 before IL-6R expression was assessed. The results demonstrated that as shown in FIG. 18, the obvious peak shift to higher intensity was observed in P2 stained with Alexa488-labeled tocilizumab, relative to the negative control. An excess of non-labeled tocilizumab inhibited the peak shift. Therefore, it is revealed that IL-6R was expressed in P2.

Example 14 Assessment of Tocilizumab Uptake in P2 Cell Population in Monkey Hepatic Nonparenchymal Cells 50 μL of a cell solution containing $2\times10^5$ monkey hepatic nonparenchymal cells prepared as in Example 1 and an antibody solution containing Alexa488-labeled tocilizumab at a final concentration of 3 g/mL were prepared. An antibody solution containing Alexa488-labeled tocilizumab and non-labeled tocilizumab at a final concentration of 1 mg/mL which is excess relative to the labeled antibody was prepared to ensure specific binding. Fc Receptor Blocking Solution (Human TruStain FcX, Biolegend) was added to the cell solution and antibody solutions at 20× dilution for FcγR blocking. The cell solution and antibody solutions thus prepared were mixed to obtain 100 μL of reaction solution. These solutions were left to react while stirring at 37° C. for 2, 5, 10, 15, or 30 minutes. The solutions were then ice-cooled, and a hepatocyte culture medium with 10 mM citrate (pH3.0, LONZA) was added to remove antibodies bound to cell surfaces by repeating centrifugation (at 3000 rpm for 3 min) and supernatant removal. Cold PBS with 2% FBS was then added to wash the cells. The cell solution was then centrifuged (at 3000 rpm for 5 min) to discard a liquid. The resulting cells were stained with an anti-CD31 antibody and an anti-CD45 antibody. After washing, the fluorescence intensity of Alexa488 in P2 was measured in FACS Canto II.

Figure 19:
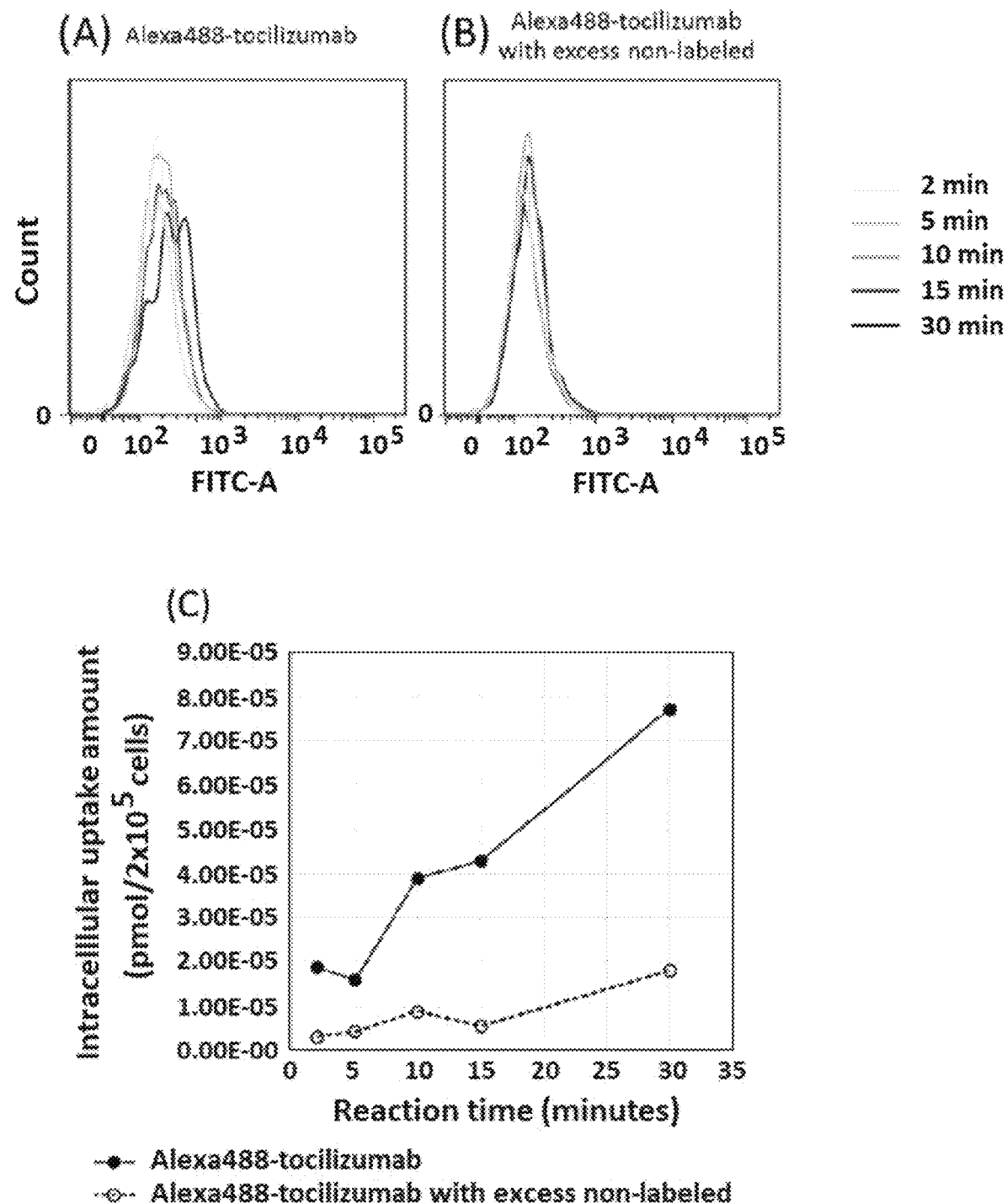
FIG. 19(A) is a histogram showing the fluorescence intensity of Alexa488-labeled tocilizumab in P2 cell population identified from a scatter diagram similar to FIG. 2, in which Alexa488-labeled tocilizumab was added at 3 g/mL to a cell solution to be incorporated into the cells at 37° C. for 2, 5, 10, 15, or 30 minutes and then the cells were stained with Pacific Blue-labeled anti-CD31 antibody and APC-labeled anti-CD45 antibody.
FIG. 19(B) shows the results obtained by adding 1 mg/mL, which is an excess amount, non-labeled tocilizumab to 3 g/mL Alexa488-labeled tocilizumab to perform reaction as in (A). The histograms with different shades ranging from light gray to black show the results of uptake for 2 to 30 minutes, respectively.
FIG. 19(C) is a plot of the uptake time on the X-axis against the uptake amounts on the Y-axis determined from the histograms shown in (A) and (B).

The results demonstrated that in P2, the fluorescence peak of Alexa488-labeled tocilizumab was shifted to higher intensity depending on the reaction time (FIG. 19A). An excess of non-labeled tocilizumab inhibited the peak shift (FIG. 19B). Therefore, it is indicated that tocilizumab specifically binds to IL-6R on a cell surface and is incorporated into cells in a time-dependent manner.

The cellular uptake amount of tocilizumab was further quantified. The fluorescence intensity of fluorescently labeled standard beads was measured using Quantum™ MESF (Bangs Laboratories) according to its accompanying protocol. The geometric mean fluorescence intensity of each standard was used to create a calibration curve according to the accompanying protocol. The uptake amount of Alexa488-labeled tocilizumab in each reaction time was calculated from the geometric mean fluorescence intensities in samples for Alexa488-labeled tocilizumab uptake. The results are shown in FIG. 19C. The uptake amount almost linearly increased with time, and the uptake rate was calculated to be $2.19\times10^{-6}$ pmol/min/$2\times10^5$ cells.

INDUSTRIAL APPLICABILITY

The present invention can predict in vivo kinetics of candidate molecules for development of pharmaceutical agents in human and monkey in an in vitro test. The present invention can predict an antigen clearance function from blood of candidate antibodies for development of pharmaceutical agents in human and monkey in an in vitro test.

SEQUENCE LISTING FREE TEXT

SEQ ID NO: 1: Synthetic oligonucleotide

The invention claimed is:

1. A method for measuring a cellular uptake amount of a molecule, comprising the steps of:
   (i) adding the molecule to an organ-derived cell population to perform incubation, wherein the molecule is incorporated into cells via a cell surface receptor,
   (ii) sorting the organ-derived cell population based on expression levels of CD31 and CD45 to produce a cell population expressing CD31 and CD45, and
   (iii) after steps (i) and (ii), measuring the amount of the molecule incorporated into the cell population,
   wherein the method comprises step (ii) subsequent to step (i), and the organ-derived cell population incubated with the added molecule is sorted based on the expression levels of CD31 and CD45,
   wherein the organ-derived cell population is a human hepatic nonparenchymal cell population, and
   wherein a $CD31^{high}$ $CD45^{low}$ cell population is sorted in step (ii).

2. The method according to claim 1, wherein the molecule is an immune complex or an antibody, and the receptor is an Fc receptor.

3. The method according to claim 1, wherein the molecule is an anti-IL-6R antibody, and the receptor is IL-6R.

4. The method according to claim 1, wherein the molecule is a nucleic acid, and the receptor is Stabilin.

5. A composition for an uptake assay of a molecule, wherein the composition comprises an organ-derived $CD31^{high}$ $CD45^{low}$ human hepatic nonparenchymal cell population and the molecule is incorporated into cells via a cell surface receptor on the cell population.

6. The composition according to claim 5, wherein the assay is performed using the method according to claim 1.

7. The composition according to claim 5, wherein the cell population is a partially purified cell population.

8. A method for producing the composition according to claim 5, comprising the steps of:
   (i) preparing organ-derived cells from an organ removed from a living body, and
   (ii) sorting the organ-derived cells based on expression levels of CD31 and CD45.

9. The method according to claim 1, wherein the molecule is an immune complex.

10. The method according to claim 1, wherein the molecule is an antibody.

11. The method according to claim 1, wherein the receptor is an Fc receptor.

12. The method according to claim 1, wherein the receptor is IL-6R.

13. The method according to claim 1, wherein the receptor is Stabilin.

* * * * *

```
                        SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic oligodeoxynucleotide

<400> SEQUENCE: 1
tccatgacgt tcctgatgct                                                  20
```